(12) United States Patent
Brodnick

(10) Patent No.: US 9,078,575 B2
(45) Date of Patent: *Jul. 14, 2015

(54) HEARTBEAT CATEGORIZATION

(71) Applicant: APN Health, LLC, Pewaukee, WI (US)

(72) Inventor: Donald Brodnick, Cedarburg, WI (US)

(73) Assignee: APN Health, LLC, Pewaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/219,826

(22) Filed: Mar. 19, 2014

(65) Prior Publication Data

US 2015/0119737 A1    Apr. 30, 2015

Related U.S. Application Data

(63) Continuation-in-part of application No. 14/067,561, filed on Oct. 30, 2013.

(51) Int. Cl.
*A61B 5/04* (2006.01)
*A61B 5/0456* (2006.01)
*A61B 5/0452* (2006.01)

(52) U.S. Cl.
CPC ......... *A61B 5/04014* (2013.01); *A61B 5/04011* (2013.01); *A61B 5/0456* (2013.01); *A61B 5/04525* (2013.01)

(58) Field of Classification Search
CPC ............. A61B 5/04011; A61B 5/0456; A61B 5/04525
See application file for complete search history.

(56) References Cited

U.S. PATENT DOCUMENTS 3,939,824 A * 2/1976 Arneson et al. ............... 600/485
4,240,442 A   12/1980 Andresen et al.
4,374,382 A    2/1983 Markowitz
(Continued)

FOREIGN PATENT DOCUMENTS

EP    1745740 A1    1/2007
EP    2047794 A1    4/2009
(Continued)

OTHER PUBLICATIONS

Pan et al. A Real-Time QRS Detection Algorithm. IEEEE Transactions on Biochemical Engineering. vol. BME-32, No. 3, Mar. 1985. <http://mirel.xmu.edu.cn/mirel/public/Teaching/QRSdetection.pdf>.

(Continued)

*Primary Examiner* — George Evanisko
(74) *Attorney, Agent, or Firm* — Jansson Munger McKinley and Shape Ltd.

(57) ABSTRACT

An automatic method for categorizing heartbeats using two or more selected ECG signals, the method comprising, when a heartbeat has been detected, the steps of: (a) determining a signal velocity for each selected signal at a categorization fiducial time $t_C$ within the detected heartbeat; (b) forming a vector $F(t_C)$ having as its components the velocities of each of the selected signals at time $t_C$; (c) determining the angle between the vector $F(t_C)$ and a previously-stored template vector; (d) comparing the angle with a threshold angle; and (e) if the angle is less than the threshold angle, categorizing the heartbeat as similar to a heartbeat which corresponds to the template vector.

56 Claims, 31 Drawing Sheets

(56) References Cited

U.S. PATENT DOCUMENTS

| | | |
|---|---|---|
| 4,583,553 A | 4/1986 | Shah et al. |
| 5,117,824 A | 6/1992 | Keimel et al. |
| 5,365,426 A | 11/1994 | Siegel et al. |
| 5,462,060 A | 10/1995 | Jacobson et al. |
| 5,526,813 A | 6/1996 | Yoshida |
| 5,560,367 A | 10/1996 | Haardt et al. |
| 5,560,368 A | 10/1996 | Berger |
| 5,701,907 A | 12/1997 | Klammer |
| 6,236,883 B1 | 5/2001 | Ciaccio et al. |
| 6,526,313 B2 | 2/2003 | Sweeney et al. |
| 6,556,860 B1 | 4/2003 | Groenewegen |
| 6,702,752 B2 | 3/2004 | Dekker |
| 6,937,888 B2 | 8/2005 | Kohler et al. |
| 7,364,550 B1 | 4/2008 | Turcott |
| 7,561,912 B2 | 7/2009 | Schatz et al. |
| 7,610,084 B2 | 10/2009 | Sweeney et al. |
| 7,792,571 B2 | 9/2010 | Sweeney et al. |
| 7,890,170 B2 | 2/2011 | Ettori et al. |
| 8,041,417 B2 | 10/2011 | Jonckheere et al. |
| 8,064,995 B1 | 11/2011 | Dupelle et al. |
| 8,137,269 B2 | 3/2012 | Sheikhzadeh-Nadjar et al. |
| 8,150,503 B2 | 4/2012 | Schatz et al. |
| 2002/0133085 A1 | 9/2002 | Kohler et al. |
| 2002/0138013 A1 | 9/2002 | Guerrero et al. |
| 2003/0216654 A1 | 11/2003 | Xu et al. |
| 2004/0015090 A1 | 1/2004 | Sweeney et al. |
| 2004/0059203 A1 | 3/2004 | Guerrero et al. |
| 2004/0186388 A1 | 9/2004 | Gerasimov |
| 2005/0245973 A1 | 11/2005 | Sherman |
| 2007/0161916 A1 | 7/2007 | Zantos et al. |
| 2008/0109041 A1 | 5/2008 | de Voir |
| 2009/0099468 A1 | 4/2009 | Thiagalingam et al. |
| 2010/0041975 A1 | 2/2010 | Chen et al. |
| 2010/0305645 A1 | 12/2010 | Sweeney et al. |
| 2011/0071375 A1 | 3/2011 | Baker, Jr. et al. |
| 2011/0137153 A1 | 6/2011 | Govari et al. |
| 2011/0172729 A1 | 7/2011 | Sweeney et al. |
| 2011/0282226 A1 | 11/2011 | Benser et al. |
| 2011/0288605 A1 | 11/2011 | Kaib et al. |
| 2012/0035488 A1 | 2/2012 | MacAdam et al. |
| 2012/0101398 A1 | 4/2012 | Ramanathan et al. |
| 2012/0123279 A1 | 5/2012 | Brueser et al. |
| 2012/0130263 A1 | 5/2012 | Pretorius et al. |
| 2012/0179055 A1 | 7/2012 | Tamil et al. |
| 2012/0184864 A1 | 7/2012 | Harlev et al. |
| 2012/0197151 A1 | 8/2012 | Schatz et al. |
| 2013/0006131 A1 | 1/2013 | Narayan et al. |
| 2013/0030314 A1 | 1/2013 | Keel et al. |
| 2013/0066221 A1 | 3/2013 | Ryu et al. |
| 2013/0109945 A1 | 5/2013 | Harlev et al. |
| 2013/0245477 A1 | 9/2013 | Brodnick et al. |

FOREIGN PATENT DOCUMENTS

| | | |
|---|---|---|
| WO | 9619939 A1 | 7/1996 |
| WO | 2005002669 A2 | 1/2005 |
| WO | 2011088043 A1 | 7/2011 |
| WO | 2012056342 A2 | 5/2012 |

OTHER PUBLICATIONS

Friesen G.M. et al. "A Comparison of the Noise Sensitivity of None QRS Detection Alogrithyms," IEEE Transactions on Biomedical Engineering, IEEE Inc. New York, US, Bd. 37, Nr. 1, 1990, Seiten 85-98.

Mancia, G., et al., Alerting Reaction and Rise in Blood Pressure During Measurement by Physician and Nurse; Hypertension, vol. 9, No. 2, Feb. 1987; pp. 209-215; downloaded from the Internet on Feb. 28, 2014; URL: http://hyper.ahajournals.org.

Torres-Pereira, L., et al. "A Non-invasive Telemetric Heart Rate Monitoring System based on Phonocadiography" Proceedings of the IEEE International Symposium on Industrial Electronics, Jul. 7-11, 1997, Guimaraes, Portugal; vol. 3, pp. 856-859.

Selvaraj, N., et al. "Assessment of heart rate variability derived from finger-tip photoplethysmography as compared to electrocardiography" Journal of Medical Engineering & Technology, vol. 32, No. 6, Nov./Dec. 2008, pp. 479-484.

Peters, C. H. et al. "Beat-to-beat detection of fetal heart rate: Doppler ultrasound cardiotocography compared to direct ECG cardiotocography in time and frequency domain" Physiological Measurement, vol. 25, pp. 585-593; Institute of Physics Publishing, 2004.

Jezewski, J. et al. "Comparison of Doppler Ultrasound and Direct Electrocardiography Acquisition Techniques for Quantification of Fetal Heart Rate Variability" IEEE Transactions on Biomedical Engineering, vol. 53, No. 5, May 2006; pp. 855-864.

Mack, D. C. et al. "Development and Preliminary Validation of Heart Rate and Breathing Rate Detection Using a Passive, Ballistocardiography-Based Sleep Monitoring System" IEEE Transactions on Information Technology in Biomedicine, vol. 13, No. 1, Jan. 2009; pp. 111-120.

Alihanka, J. et al. "A new method for long-term monitoring of the ballistocardiogram, heart rate, and respiration" American Physiological Society, 1981, R384-R392.

Godinez M., et al.: "On-line fetal heart rate monitor by Phonocardiography" Proceedings of the 25th Annual International Conference of the IEEE, Cancun, Mexico, Sep. 17-21, 2003, pp. 3141-3144.

De Boer, R. W. et al. "Relationships between short-term blood-pressure fluctuations and heart-rate variability in resting subjects I: a spectral analysis approach" Medical & Biological Engineering & Computing, Jul. 1985, vol. 23, pp. 352-358.

* cited by examiner

LEGEND $x_p(t)$ = analog ECG channel signals (N channels)
$i$ = time index of digital signal streams
$x_p(t_i)$ = digital ECG channel signals
$f_p(t_i)$ = intermediate digital ECG channel signals
$|x|$ = ABS(x) = absolute value of x
$g_p(t_i)$ = filtered ECG channel signals = $|f_p(t_i)|$
$G(t_i)$ = sum of all $g_p(t_i)$ = velocity sum
$k$ = number of time samples in a boxcar sum
$T$ = threshold (initial value in example = 1000)
$G_{max}$ = maximum value of summed signal $G(t_i)$
    during the most recent $t_m$-second period
    ($t_m$-second time periods are consecutive,
    not moving-window periods)
$t_m$ = preset time period of timer$_m$*
$t_R$ = refractory period (timer$_R$**)
$t_L$ = detection failure time limit (timer$_R$)
$F(t_D)$ = vector having components $f_p(t_D)$,
    at time of heartbeat detection $t_i = t_D$
$SVM_D$ = squared vector magnitude (dot product
    of $F(t_D)$ with itself: $[F(t_D) \cdot F(t_D)]$
$Q$ = number of possible templates
$q$ = index of heartbeat-category template vectors
$F_q$ = heartbeat-category template vector q
$SVM_q$ = squared vector magnitude (dot product
    of $F_q$ with itself: $[F_q \cdot F_q]$
$DP_q$ = dot product of F(tD) with template
    vector q: $[F(t_D) \cdot F_q]$
$SCDA_q$ = signed squared cosine difference angle
$SC_M$ = maximum value of $SCDA_q$
$SC_L$ = limit value of $SCDA_q$ defining template
    categories (threshold angle = $\theta_L$)
$q_E$ = index of empty template vector slot
$q_M$ = index of template vector with $SC_M$
$C_q$ = count of heartbeats matching template
    vector $F_q$
$F_E = F_q$ at $q = q_E$; $F_M = F_q$ at $q = q_M$
$SVM_E = SVM_q$ at $q = q_E$; $SVM_M = SVM_q$ at $q = q_M$
$C_E = C_q$ at $q = q_E$; $C_M = C_q$ at $q = q_M$ \* timer$_m$ is a countdown timer
\*\* refractory timer$_R$ is an elapsed-time timer sampling rate $f_s$ = 1,000sps ($\Delta t$ = 1msec); N = 3;
k = 20; $t_m$ = 2sec; $t_R$ = 120msec: $t_L$ = 5sec

FIG. 4

Instantaneous signal velocity $f_1(t_i)$ vs. time $t_i$

Instantaneous signal velocity $f_2(t_i)$ vs. time $t_i$

Instantaneous signal velocity $f_3(t_i)$ vs. time $t_i$

Absolute velocity $g_1(t_i)$ vs. time $t_i$

Absolute velocity $g_2(t_i)$ vs. time $t_i$

Absolute velocity $g_3(t_i)$ vs. time $t_i$

Absolute velocity sum G(t$_i$) vs. time t$_i$

G$_{max}$ vs. time t$_i$

Threshold T vs. time t$_i$

Refractory timer (timer$_R$) vs. time t$_i$

FIG. 10A

| | $t_D$ | $f_1(t_D)$ | $f_2(t_D)$ | $f_3(t_D)$ | $SVM_D$ |
|---|---|---|---|---|---|
| Heartbeat #1 | 0.066 | 186 | -13 | 813 | 695734 |
| Heartbeat #2 | 0.954 | 201 | 38 | 813 | 702814 |
| Heartbeat #3 | 1.980 | 204 | 30 | 820 | 714916 |
| Heartbeat #4 | 3.054 | 208 | 11 | 822 | 719069 |
| Heartbeat #5 | 4.165 | 239 | 26 | 789 | 680318 |
| Heartbeat #6 | 4.593 | -559 | -100 | -384 | 469937 |
| Heartbeat #7 | 5.708 | 223 | 2 | 852 | 775637 |
| | | | | | |
| Template 8 | | -551 | -246 | -124 | 379493 |
| Template 7 | | 186 | -13 | 813 | 695734 |
| Template 6 | | -559 | -100 | -384 | 469937 |

FIG. 10B

| | $DP_8$ | $SCDA_8$ | $\theta_8$ (°) | $DP_7$ | $SCDA_7$ | $\theta_7$ (°) | $DP_6$ | $SCDA_6$ | $\theta_6$ (°) | category |
|---|---|---|---|---|---|---|---|---|---|---|
| Heartbeat #1 | -200100 | -0.1517 | 112.92 | | | | | | | new 7 |
| Heartbeat #2 | -220911 | -0.1830 | 115.33 | 697861 | 0.9960 | 3.63 | | | | 7 |
| Heartbeat #3 | -221464 | -0.1808 | 115.16 | 704214 | 0.9970 | 3.12 | | | | 7 |
| Heartbeat #4 | -219242 | -0.1761 | 114.82 | 706831 | 0.9987 | 2.10 | | | | 7 |
| Heartbeat #5 | -235921 | -0.2156 | 117.67 | 685573 | 0.9930 | 4.80 | | | | 7 |
| Heartbeat #6 | 380225 | 0.8107 | 25.79 | -414866 | -0.5264 | 136.51 | -452025 | -0.5606 | 138.48 | new 6 |
| Heartbeat #7 | -229013 | -0.1782 | 114.97 | 734128 | 0.9987 | 2.05 | | | | 7 |

ECG signal $x_1(t_i)$ vs. time $t_i$

ECG signal $x_2(t_i)$ vs. time $t_i$

ECG signal $x_3(t_i)$ vs. time $t_i$

Absolute velocity sum $G(t_i)$ vs. time $t_i$

FIG. 17A

| | $t_D$ | $f_1(t_D)$ | $f_2(t_D)$ | $f_3(t_D)$ | $f_1(t_{D+20})$ | $f_2(t_{D+20})$ | $f_3(t_{D+20})$ | $SVM_D$ |
|---|---|---|---|---|---|---|---|---|
| Heartbeat #1 | 0.066 | 186 | -13 | 813 | 73 | -251 | -394 | 919300 |
| Heartbeat #2 | 0.954 | 201 | 38 | 813 | 147 | -216 | -349 | 892880 |
| Heartbeat #3 | 1.980 | 204 | 30 | 820 | 79 | -190 | -365 | 890482 |
| Heartbeat #4 | 3.054 | 208 | 11 | 822 | 79 | -280 | -261 | 871831 |
| Heartbeat #5 | 4.165 | 239 | 26 | 789 | -77 | -188 | -321 | 824632 |
| Heartbeat #6 | 4.593 | -559 | -100 | -384 | -360 | -227 | -457 | 859915 |
| Heartbeat #7 | 5.708 | 223 | 2 | 852 | -132 | -157 | -507 | 1074759 |
| | | | | | | | | |
| Template 8 | | -551 | -246 | -124 | -125 | -213 | -129 | 457128 |
| Template 7 | | 186 | -13 | 813 | 73 | -251 | -394 | 919300 |
| Template 6 | | 239 | 26 | 789 | -77 | -188 | -321 | 824632 |
| Template 6 | | -559 | -100 | -384 | -360 | -227 | -457 | 859915 |

FIG. 17B

| | $DP_8$ | $SCDA_8$ | $\theta_8(°)$ | $DP_7$ | $SCDA_7$ | $\theta_7(°)$ | $DP_6$ | $SCDA_6$ | $\theta_6(°)$ | $DP_5$ | $SCDA_5$ | $\theta_5(°)$ | category |
|---|---|---|---|---|---|---|---|---|---|---|---|---|---|
| Heartbeat #1 | -104936 | -0.026 | 99.32 | | | | | | | | | | new 7 |
| Heartbeat #2 | -148257 | -0.054 | 103.42 | 900314 | 0.988 | 6.42 | | | | | | | 7 |
| Heartbeat #3 | -143784 | -0.051 | 103.02 | 901481 | 0.993 | 4.89 | | | | | | | 7 |
| Heartbeat #4 | -135808 | -0.046 | 102.42 | 885712 | 0.979 | 8.37 | | | | | | | 7 |
| Heartbeat #5 | -144843 | -0.056 | 103.65 | 853614 | 0.961 | 11.36 | | | | | | | new 6 |
| Heartbeat #6 | 532529 | 0.721 | 31.86 | -204111 | -0.053 | 103.27 | -222084 | -0.070 | 105.29 | | | | new 5 |
| Heartbeat #7 | -113669 | -0.026 | 99.33 | 963657 | 0.940 | 14.19 | 928004 | 0.972 | 9.69 | -137167 | -0.020 | 98.20 | 6 |

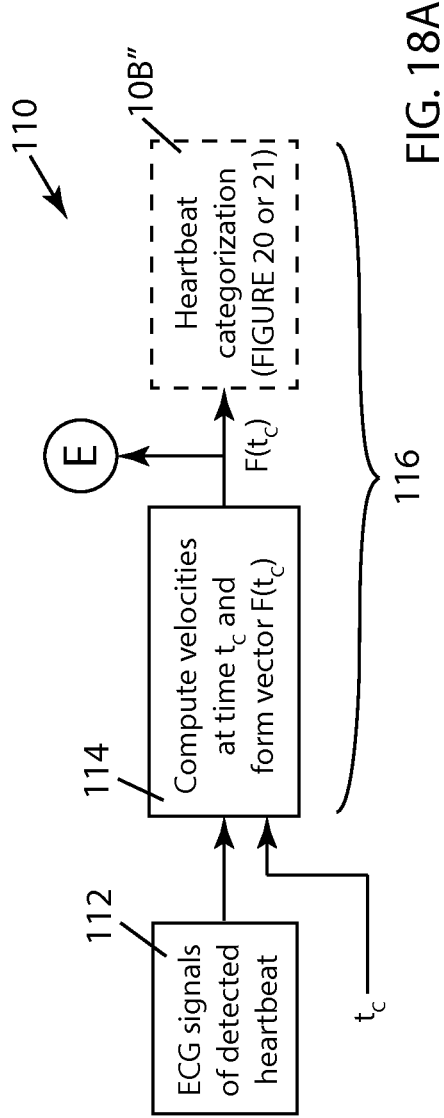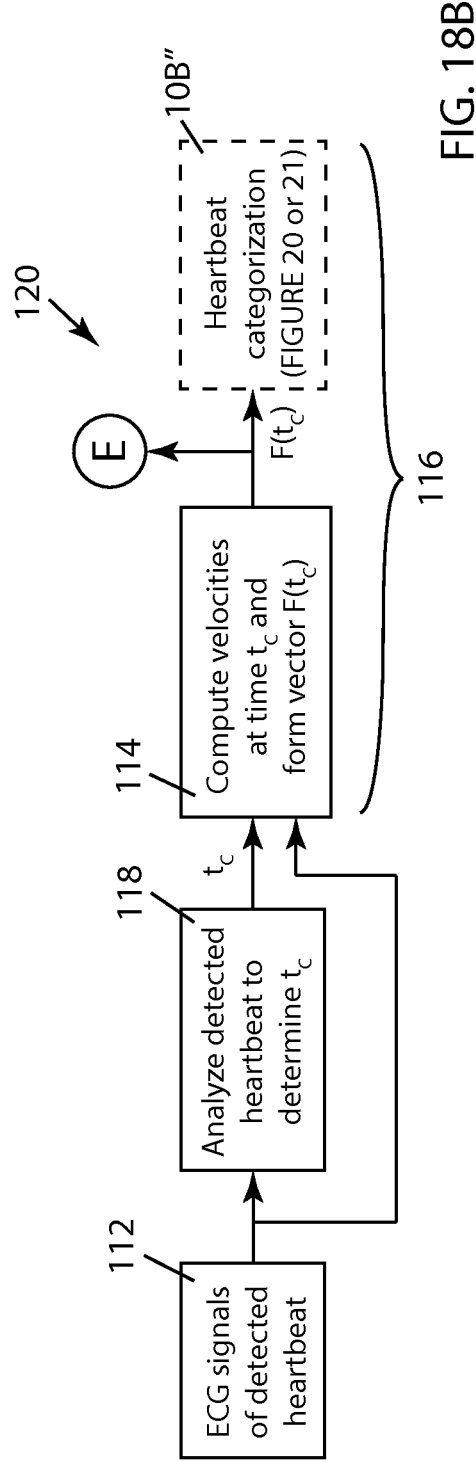

HEARTBEAT CATEGORIZATION

RELATED APPLICATIONS

This application is a continuation-in-part of application Ser. No. 14/067,561 filed on Oct. 30, 2013.

FIELD OF THE INVENTION

This invention is related generally to the field of electrophysiology, and more particularly to technology for accurate measurement of parameters within ECG electrical signals such as heart rates and the nature of individual heartbeats.

BACKGROUND OF THE INVENTION

The invention disclosed herein involves the processing of multiple channels of electrical signals which are produced by the heart. These channel signals primarily include the ECG signals from body-surface electrodes although signals from electrodes within the body, i.e., intracardiac signals from within vessels and chambers of the heart and epicardial signals from the outer surface of the heart may also be among the cardiac signals processed. Throughout this document, the term "ECG signal" is used to refer to all of these types of channel signals since the inventive method is primarily intended to be used with body-surface electrodes. Such use of terminology is not intended to be limiting to the scope of the invention.

Numerous methods for signal processing of heartbeats are known. Among these are methods disclosed in the following patent applications: PCT International Patent Application No. PCT/US 12/54265 filed on Sep. 7, 2012 and entitled "R-Wave Detection Method;" U.S. patent application Ser. No. 13/842,994 filed on Mar. 15, 2013 and entitled "Multi-Channel Cardiac Measurements;" U.S. patent application Ser. No. 13/888,070 filed on May 5, 2013 and entitled "Multi-Channel Cardiac Measurements;" and U.S. patent application Ser. No. 13/922,953 filed on Jun. 20, 2013 and entitled "Multi-Channel Cardiac Measurements." Each of these applications are in whole or in part invented by the inventor of the present invention and are commonly owned by APN Health, LLC of Pewaukee, Wis. None of these applications combine signals of multiple cardiac channels in the heartbeat detection process prior to performing a threshold comparison. None of these inventions includes steps which categorize the detected heartbeats into categories having similar heartbeat morphologies or shapes.

Other current technology which involves heartbeat detection and categorization relates to systems for post-processing of ECG signals captured by a Holter monitor. These systems typically involve the processing of ECG signals using values of such signals at more than one point in time within an individual heartbeat. In contrast, the present invention depends on measurements at a single instant in time in order to detect and categorize heartbeats, allowing this inventive system to detect heartbeats very early in the time period of the heartbeat and to operate essentially in real time.

Categorizing heartbeats into groups having similar morphologies in essentially real time enables a cardiologist to very quickly identify the frequency of occurrence of various ectopic heartbeats, particularly for patients undergoing interventional procedures to alleviate the causes of such heartbeats. Among the ectopic heartbeats which are of importance are: premature ventricular contractions (PVC); premature atrial contractions (PAC); various types of bundle branch blocks; ventricular escape beats; junctional escape beats; fusion beats; and paced beats.

PVC and PAC heartbeats (also known by several other names) are among the most common ectopic heartbeats and when they occur as individual beats rather than in a series of repetitive beats, are not considered to be clinically significant. Such individual beats commonly occur in healthy young and elderly patients without heart disease. However, when ectopic beats recur on a much more regular basis, interventional treatment or procedures may be undertaken to alleviate such cardiac abnormalities. The present invention is an important advance in the technology of cardiac diagnosis and treatment by providing a rapid and reliable method for heartbeat detection and categorization.

OBJECTS OF THE INVENTION

It is an object of the inventive automatic method of heartbeat categorization to provide a reliable method for categorization of heartbeats.

Another object of the inventive method is to provide an automatic method by which heartbeats can be categorized into predefined classes of heartbeats.

Another object of the inventive method is to provide an automatic method by which heartbeats can be categorized into a set of adaptively-defined classes of heartbeats based on a patient's specific heartbeats.

Another object of the inventive method is to provide an automatic method by which premature ventricular contractions can be identified, characterized, and counted.

Still another object of the inventive method is to provide an automatic method of heartbeat categorization which displays useful heartbeat characterization information to a cardiologist.

Yet another object of this invention is to provide a method of heartbeat categorization which is applicable to post-processing of data recorded by a Holter monitor.

An additional object of this invention is to provide a method of heartbeat categorization which can be utilized with a variety of heartbeat detection methods.

These and other objects of the invention will be apparent from the following descriptions and from the drawings.

SUMMARY OF THE INVENTION

The invention is an automatic method for categorizing heartbeats using two or more selected ECG signals. The method comprises, when a heartbeat has been detected, (a) determining a signal velocity for each selected signal at a categorization fiducial time $t_C$ within the detected heartbeat, (b) forming a vector $F(t_C)$ having as its components the velocities of each of the selected signals at time $t_C$, (c) determining the angle between the vector $F(t_C)$ and a previously-stored template vector, (d) comparing the angle with a threshold angle, and (e) if the angle is less than the threshold angle, categorizing the heartbeat as similar to a heartbeat which corresponds to the template vector.

In highly-preferred embodiments of the inventive method for categorizing heartbeats, angle determination and comparison include the steps of (i) computing a squared vector magnitude $SVM_C$ as the dot product of $F(t_C)$ with itself, (ii) computing the dot product $DP_q$ of $F(t_C)$ with a template vector $F_q$, (iii) computing a squared vector magnitude $SVM_q$ as the dot product of $F_q$ with itself, (iv) computing a signed squared cosine difference angle $SCDA_q$ as $$SCDA_q = \mathrm{sgn}(DP_q)*DP_q*DP_q/(SVM_C*SVM_q),$$

and (v) comparing $SCDA_q$ with a squared cosine threshold $SC_L$. Some of these embodiments further include comparing the vector $F(t_C)$ with a plurality of template vectors to determine if the vector $F(t_C)$ is within the threshold angle of any of the plurality of template vectors.

In some embodiments, if the angle between the vector $F(t_C)$ and more than one of the plurality of template vectors is less than the threshold angle, the heartbeat is categorized as similar to a heartbeat which corresponds to the template vector having the smallest angle between itself and the vector $F(t_C)$. Also in some embodiments, if the angle between the vector $F(t_C)$ and each of the plurality of template vectors is greater than or equal to the threshold angle, a template vector having $F_q = F(t_C)$ is added to the plurality of template vectors.

In some preferred embodiments, the patient is in a non-sedated state and the inventive method further includes the step of providing interventional treatment to the patient in a sedated state based on heartbeats categorized while the patient was in the non-sedated state.

In some embodiments of the inventive automatic heartbeat categorization method, each of the template vectors has a threshold angle associated therewith, and not all such vectors have the same threshold angle associated therewith.

In some embodiments, at least a portion of the plurality of template vectors are preset template vectors, and in some of these embodiments, each of the plurality of template vectors is a preset template vector.

In some preferred embodiments, the method further includes a slot-plurality of template vector slots, and the slot-plurality is greater than or equal to the plurality of template vectors. Each template vector is stored in a corresponding template vector slot, and if the vector $F(t_C)$ is not within the threshold angle of any of the plurality of template vectors and an empty template vector slot is available, a new template vector $F_q = F(t_C)$ is added to the plurality of template vectors. In some of these embodiments, if no empty template vector slot is available, one of the template vectors is replaced with a new template vector $F_q = F(t_C)$.

Some highly-preferred embodiments of the inventive automatic heartbeat categorization method include storing the categorized heartbeat, and some of these embodiments further include displaying information descriptive of one or more stored heartbeats.

In certain highly-preferred embodiments, determining the velocity of each of the selected signals includes digitizing each of the selected signals and filtering each of the digitized signals to generate the velocity for each selected signal.

In certain highly-preferred embodiments, three ECG signals are selected, and the signals form a quasi-orthogonal set.

In some other embodiments of the inventive automatic heartbeat categorization method, the ECG signals further include one or more ECG signals in addition to the selected ECG signals, and the method includes storing one or more of the additional ECG signals. Some of these embodiments include displaying information descriptive of a detected heartbeat.

Certain other embodiments of the inventive automatic heartbeat categorization method, when a heartbeat has been detected, include the steps of (i) forming a vector $F(t_C)$ having as its components the velocities of each of the selected signals at time $t_C$ and the velocities of each of the selected signals at time $t_C + \delta$, (ii) determining the angle between the vector $F(t_C)$ and a previously-stored template vector, (iii) comparing the angle with a threshold angle, and (iv) if the angle is less than the threshold angle, categorizing the heartbeat as similar to a heartbeat which corresponds to the template vector.

Certain embodiments of the inventive automatic heartbeat categorization method of claim 1 further include the steps of (i) storing the selected signals, (ii) determining a velocity for each of the selected signals, (iii) summing the absolute values of each signal velocity to generate an absolute velocity sum $G(t)$, (iv) finding the maximum peak of the sum and the time thereof within the detected heartbeat, and (v) setting time $t_C$ as the time before and nearest to the time of the peak when the sum is substantially equal to a preset fraction of the peak.

Certain other embodiments further include the steps of (i) storing the selected signals, (ii) determining a velocity for each of the selected signals, (iii) summing the absolute values of each signal velocity to generate an absolute velocity sum $G(t)$, and (iv) setting $t_C$ equal to the time at which $G(t)$ becomes greater than a threshold T.

Additional embodiments further include storing the selected signals and determining $t_C$ as a preset time after the start of the detected heartbeat. Some such embodiments include (i) determining a velocity for each of the selected signals, (ii) summing the absolute values of each signal velocity to generate an absolute velocity sum $G(t)$, and (iii) determining the start of the detected heartbeat as the time at which $G(t)$ rises above a heartbeat-pending threshold $T_p$ and remains above $T_p$ until $G(t)$ rises above a heartbeat-confirming threshold $T_c$. In some of these embodiments, the detected heartbeat is within a cardiac cycle and the method further includes the step of computing the median of $G(t)$ within the cardiac cycle, heartbeat-pending threshold $T_p$ being a multiple of the median of $G(t)$ across the cardiac cycle; in some, the multiple of the median of $G(t)$ within the cardiac cycle is between 2 and 5; and in some, the heartbeat-confirming threshold $T_c$ is between 30% and 60% of the expected peak of the detected heartbeat.

In certain embodiments, the inventive automatic heartbeat categorization method further includes the steps of (a) storing the selected signals, (b) determining a velocity for each of the selected signals, (c) summing the absolute values of each signal velocity to generate an absolute velocity sum $G(t)$, (d) cross-correlating $G(t)$ with a predetermined shape function, and (e) deriving time $t_C$ from the cross-correlation. In some of these embodiments, time $t_C$ is set at the time the cross-correlation becomes greater than a correlation threshold. The correlation threshold may be between about 25% and 35% of the peak value of the cross-correlation, and in some embodiments this threshold may be about 30% of the peak value of the cross-correlation.

In other of these embodiments, time $t_C$ is set at a preset correlation time interval before the time of maximum cross-correlation. In some embodiments, the predetermined shape function is a triangle, and in some embodiments, the predetermined shape function is a parabola. The width of the shape function may be between 90 and 150 milliseconds, and in some embodiments, the width is about 120 milliseconds.

In certain other embodiments, categorization fiducial time $t_C$ is derived from an output signal of a heartbeat detector selected from the group consisting of motion ultrasound, audio, optical detection of blood flow, pressure measurement, and ballistocardiography.

In certain embodiments, categorization fiducial time $t_C$ is derived from an intracardiac signal from an electrode placed adjacent to the origin of the heartbeat of interest. In some of these embodiments, time $t_C$ is set at a preset time interval before the activation time in an intracardiac signal.

The present invention is a method which is conveniently illustrated using block diagrams or flow charts to describe the various steps of the inventive method and the embodiments thereof. As used herein, the terms "step", "flow chart element", "process element" or other similar terms may be used to describe the various individual parts of the block diagrams or flow charts. Used as such, there is no intended difference in the meaning of these terms. When an embodiment is illustrated in more than one figure, the term "process portion" and "process" are used herein interchangeably. Specific reference numbering makes such interchangeable usage unambiguous.

The term "velocity" as used herein refers to the rate of change of a signal with respect to time.

The term "within a threshold angle" as used herein refers to an angle being compared with a threshold angle as being less than the threshold angle.

The term "quasi-orthogonal" as used herein refers to the property of a set of ECG signals such that each signal in the set is approximately independent of the other signals in the set. (In an orthogonal set, each signal in the set is fully independent of the other signals in the set.) Graphically, each signal in a two- or three-dimensional quasi-orthogonal set of ECG signals is approximately 90° from the other ECG signals in the set.

The term "categorization fiducial time" as used herein refers to the time at which the velocities of selected ECG signals are evaluated as inputs to the inventive automatic heartbeat categorization method.

The term "origin of a heartbeat" as used herein refers to the region of muscle cells which trigger the depolarization which results in a heartbeat.

BRIEF DESCRIPTION OF THE DRAWINGS

FIG. 4 is a legend for the various terms used in the block diagrams or flow charts of FIGS. 1-3.

FIG. 10A is a table of detection times of the detected heartbeats during the time period of FIGS. 6A-6C and values of computed velocity and squared vector magnitude of the velocity vector $F(t_D)=\{f_1(t_D), \ldots, f_n(t_D)\}$ generated in the embodiment of FIGS. 1-4 for the selected signals in FIGS. 6A-6C. FIG. 10A also includes three template vectors and their squared vector magnitudes as generated within the example.

FIG. 10B is a table illustrating the computations made during the operation of the inventive method for the time period shown in FIGS. 6A-6C.

FIG. 17A is a table (similar to that of FIG. 10A) which shows detection times of the detected heartbeats during the time period of FIGS. 6A-6C and values of computed velocity and squared vector magnitude of the velocity vector $F(t_D) =\{f_1(t_D), \ldots, f_N(t_D)\}$ generated in the alternative embodiment of FIGS. 15 and 2-4 for the selected signals in FIGS. 6A-6C. FIG. 17A also includes four template vectors and their squared vector magnitudes as generated within this example.

FIG. 17B is a table (similar to that of FIG. 10B) illustrating the computations made during the operation of the alternative embodiment of FIG. 17A of the inventive method for the time period shown in FIGS. 6A-6C.

FIG. 18A is a high-level schematic block diagram of the inventive method for heartbeat categorization of a detected heartbeat, illustrating that the inventive method utilizes a vector $F(t_C)$ for heartbeat categorization where $t_C$ is a categorization fiducial time at which the vector $F(t_C)$ is evaluated.

FIG. 18B is a high-level schematic block diagram which is a modification to FIG. 18A, illustrating the addition of determining categorization fiducial time $t_C$ by analyzing a detected heartbeat prior to heartbeat categorization.

DETAILED DESCRIPTION OF PREFERRED EMBODIMENTS

Figure 1:
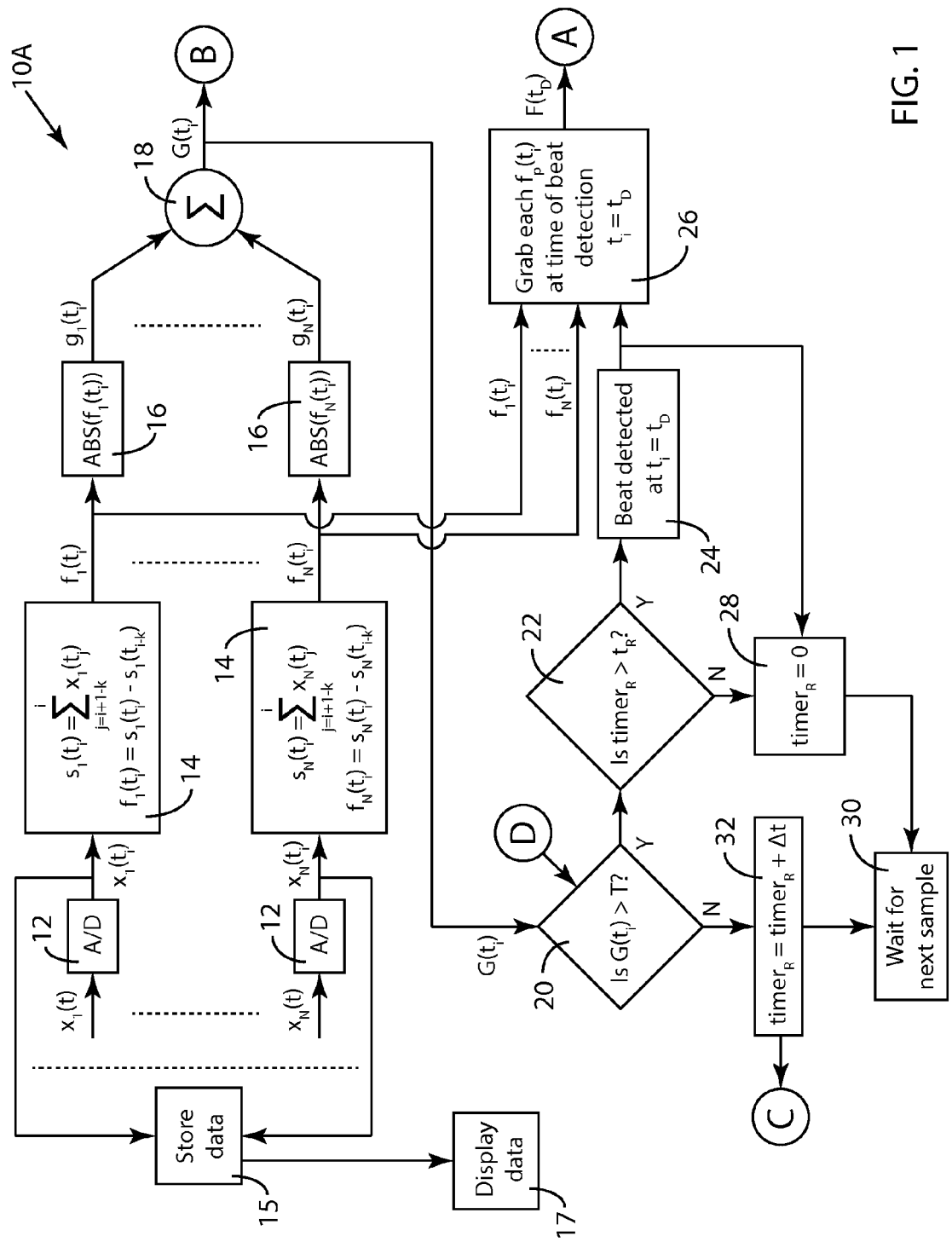
FIG. 1 is a schematic block diagram of a portion of one embodiment of the inventive method for detecting and categorizing heartbeats using two or more ECG signals. The block diagram of FIG. 1 primarily illustrates the portion of such embodiment which filters the ECG signals and detects heartbeats.
Figure 2:
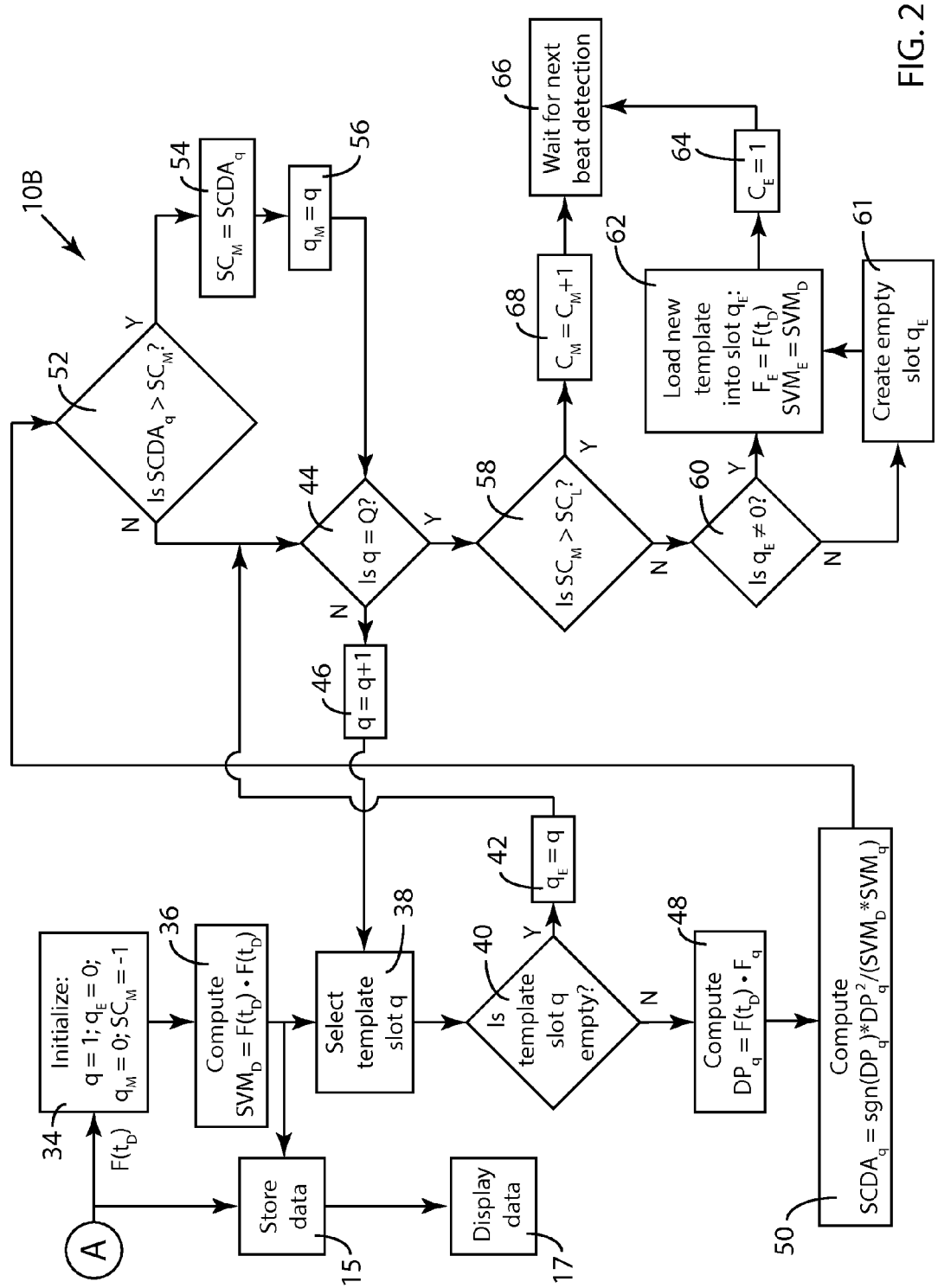
FIG. 2 is a schematic block diagram of another portion of the embodiment partially illustrated in FIG. 1. The block diagram of FIG. 2 primarily illustrates the portion of such embodiment which categorizes the detected heartbeats. This embodiment includes steps to add new templates for comparison with the vector representing a detected heartbeat when the heartbeat is not found to be similar to any of the heartbeats represented by template vectors at the time of heartbeat detection.
Figure 3:
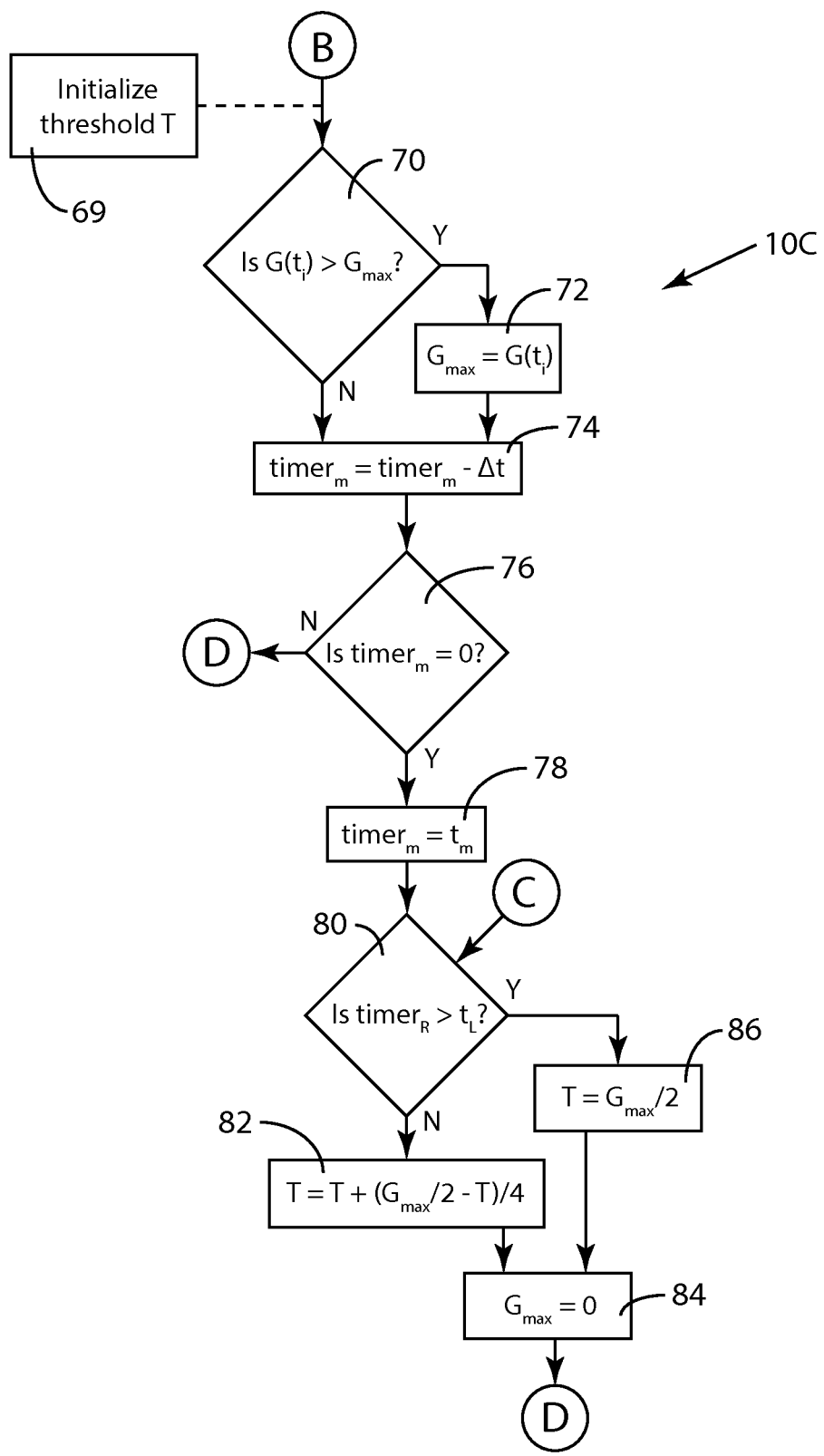
FIG. 3 is a schematic block diagram of yet another portion of the embodiment partially illustrated in FIGS. 1 and 2. The block diagram of FIG. 3 primarily illustrates the portion of such embodiment which sets threshold T used in the embodiment of the inventive method to compare with the sum of the absolute velocities of the plurality of ECG signals, as illustrated in FIG. 1.

FIGS. 1-4 illustrate one embodiment of the inventive method for heartbeat detection using two or more ECG signals. FIGS. 1-3 are schematic block diagram representations of the method. FIG. 4 shows a legend 10E for the various terms used in the embodiment of FIGS. 1-3, giving definitions for the various signals, terms in the equations and preset parameters. The legend also includes a set of typical values for preset parameters which are used within the embodiment.

The block diagram of FIG. 1 is a flow chart of steps illustrating the process portion 10A of this embodiment which filters the ECG signals and detects heartbeats. In FIG. 1, each signal in a set of selected ECG signals $[x_1(t), \ldots, x_N(t)]$ is digitized in analog-to-digital converters (A/D) 12 to form a set of digitized ECG signals $[x_1(t_i), \ldots, x_N(t_i)]$. In this embodiment, A/D converters 12 sample the ECG signals $[x_1(t), \ldots, x_N(t)]$ at a rate of 1,000 sps. For example, $x_1(t_i)$ is the sampled value of $x_1(t)$ at $t=t_i$. The number N of selected ECG signals is 2 or more. Later in the description of this embodiment, the value of N will be 3 for purposes of illustration. Again, N=3 is not intended to be limiting to the scope of the inventive method. (When referring herein to an individual but non-specific signal among sets of N signals, the subscript p may be used.)

Each digitized signal $x_p(t_i)$ in the set of digitized ECG signals $[x_1(t_i), \ldots, x_N(t_i)]$ is filtered in one of N flow chart elements 14 to generate a velocity $f_p(t_i)$ of $x_p(t_i)$ at each sampling time value $t_i$. In this embodiment, filters 14 are first-difference filters, and specifically, boxcar filters with a boxcar width k of 20 samples. As the equations in flow chart elements 14 indicate, velocity $f_p(t_i)$ of $x_p(t_i)$ is the difference between two sums of samples $(s_p(t_i)-s_p(t_{i-k}))$, the first sum $s_p(t_i)$ being the sum of the sampled value $x_p(t_i)$ and the previous 19 sampled values of $x_p(t)$, and the second sum $s_p(t_{i-k})$ being the sum of the 20 sampled values of $x_p(t)$ immediately prior to the samples of the first sum. Since filter 14 is a boxcar filter, it produces some smoothing in the filtered velocity signal $f_p(t_i)$. The wider the boxcars are, the more high frequencies are removed during the filtering process 14. And, the value of velocity $f_p(t_i)$ lags behind the actual time $t_i$, but such lag has no detrimental effect on heartbeat detection and categorization being processed.

In general, the selected ECG signals may be filtered in a variety of ways to generate values for the velocities $[f_1(t), f_N(t)]$ of the selected ECG signals $[x_1(t), x_N(t)]$. For example, a more general expression for digital filters includes a set of coefficients multiplying the individual time samples in the summations of flow chart elements 14, such that for ECG signal $x_1(t_i)$, $s_1(t_i)=\Sigma(a_j * x_1(t_{i-j}))$ for j=0 to k−1, where the values of $a_j$ are a set coefficients. Each sample in the summation is weighted by a coefficient $a_j$. For the boxcar filter example in the embodiment of FIG. 1, all of the $a_j$ are equal to 1. The particular boxcar filter example is not intended to limit the scope of the filter structure in the present invention; other filters made be used to generate the velocities.

The value of boxcar width k=20 is not intended to be limiting; other boxcar widths may be used. For k=20 and a sampling rate of 1,000 sps, the first difference boxcar filter has null points at 0 Hz and integer multiples of 50 Hz. Thus, such a filter has a peak at 19 Hz. With a null at 0 Hz, the filters remove amplifier offsets and low-frequency artifacts. The null at 50 Hz reduces higher-frequency noise.

Each velocity signal $f_p(t_i)$ is further filtered in flow chart element 16 which generates the absolute value $g_p(t_i)$ of $f_p(t_i)$. Then, all N absolute value velocities $[g_1(t_i), \ldots, g_N(t_i)]$ are summed in flow chart element 18 to generate a absolute velocity sum $G(t_i)$ at each sampled instant in time $t_i$.

Velocity sum $G(t_i)$ is an input into a flow chart decision element 20 in which $G(t_i)$ is compared with a threshold T. The value of threshold T is adaptively determined in this embodiment of the inventive method and has a value of about one-half of an expected maximum value of sum $G(t_i)$. More detail of this embodiment of the adaptive determination of threshold T is shown in FIG. 3 and will be described later in this document.

In flow chart element 20, if $G(t_i)$ is greater than threshold T, process 10A proceeds to a flow chart decision element 22, and if $G(t_i)$ is not greater than threshold T, process 10A proceeds to a flow chart element 32 in which a refractory timer (timer$_R$) is incremented by the sampling period $\Delta t$, and process 10A proceeds to flow chart element 30 to wait for the next sampling cycle. In this embodiment, $\Delta t$ is 1 msec since the sampling rate is 1,000 sps.

In decision element 22, if timer$_R$ is greater than a preset refractory period $t_R$, then a heartbeat has been detected at time $t_i = t_D$ as indicated in flow chart element 24, at which point process 10A proceeds to flow chart element 26. After time of detection $t_D$ is set to time $t_i$ in flow chart element 26, timer$_R$ is set to 0 in flow chart element 28 and process 10A proceeds to flow chart element 30 to wait for the next sampling time. In decision element 22, if timer$_R$ is not greater than $t_R$, then timer$_R$ is set to 0 in element 28 and process 10A waits for the next sampling time in element 30.

In flow chart element 26, a vector $F(t_D)$ is formed from each of the velocities $f_p(t_D)$ such that vector $F(t_D) = \{f_1(t_D), \ldots, f_N(t_D)\}$. (As used herein, vector quantities are indicated by the use of curly brackets as in the definition of $F(t_D)$ above. The square bracket notation as used early herein, such as the set of digitized ECG signals $[x_1(t_i), \ldots, x_N(t_i)]$, indicates a series of quantities not operated on as a vector.)

Flow chart element 15 in FIG. 1 illustrates that the N digitized selected ECG signals $[x_1(t_i), \ldots, x_N(t_i)]$ are stored within the inventive method. Flow chart element 17 illustrates that the stored data may be displayed to a user during or after the operation of the inventive method. Flow chart elements 15 and 17 also appear in FIGS. 2 and 12 to indicate that data other than as indicated in FIG. 1 may also be stored and displayed within the inventive method. Other data not specifically shown in these figures may also be stored and/or displayed as desired since the inventive method is implemented within a digital computer which easily stores data for later use. Certain interim values can of course be recomputed but for purposes of speed, storing for later use may be preferred. The indications of specific data stored are not intended to be limiting within the scope of the present invention.

FIG. 1 shows four circled letters A through D. These points within the flow chart of FIG. 1 indicate points in process 10A of the embodiment which proceed to similarly-labeled points within either FIG. 2 or FIG. 3. These points of process continuity will be discussed later in the detailed description.

FIG. 2 is a schematic block diagram of another portion of the embodiment partially illustrated in FIG. 1. It is a flow chart of steps illustrating the process portion 10B of the embodiment which categorizes the detected heartbeats.

Referring to FIG. 2, point A indicates that this process portion 10B of the embodiment of the inventive process proceeds from point A of FIG. 1, at which point a heartbeat has been detected at time $t_D$ and vector $F(t_D)$ of velocities has been formed. Heartbeat detection time $t_D$ occurs during the initial portion of a heartbeat, and $F(t_D)$ is a vector quantity which characterizes the detected heartbeat in the remaining steps of the inventive method for the detection of heartbeats.

During the heartbeat categorization portion 10B of this embodiment, the method stores template heartbeats, corresponding template vectors and other related information at least for comparing with a detected heartbeat which has been detected in process portion 10A. Such template vectors are described as being stored in template vector slots (slots), and there are assumed in this embodiment to be Q such slots. The slots are identified as having an index q from 1 to Q. When a heartbeat is categorized as being similar to the template associated with slot q, a heartbeat count $C_q$ is incremented by 1 such that the number of heartbeats in each category is counted.

In FIG. 2, four variables are initialized in flow chart element 34 at the beginning of the categorization of each detected heartbeat. These four variable initializations are: $q=1$; $q_E=0$; $q_M=0$; and $SC_M=-1$. Template index q is set to a starting slot (slot 1), and an empty slot index $q_E$ (indicating that slot $q_E$ is available for a new template vector) is set to point to no slot ($q_E=0$). A slot index $q_M$ is the index of the slot containing the template vector associated with the computed quantity $SC_M$ which is itself set to −1 in the initialization steps of flowchart element 34. At the time of initialization 34, no slot is associated with a value of $SC_M$ ($q_M=0$). (The term $SC_M$ will be defined later in this detailed description of FIG. 2.)

In flow chart element 36, a value for $SVM_D$ is computed as the dot product of vector $F(t_D)$ with itself: $SVM_D = F(t_D) \cdot F(t_D)$. $SVM_D$ is herein called the squared vector magnitude of vector $F(t_D)$. The dot product of two vectors X and Y is equal to the product of the magnitude of the each vector times the cosine of the angle $\theta$ between the vectors: $X \cdot Y = |X| * |Y| * \cos \theta$. Thus, the dot product of a vector with itself is the square of the magnitude of that vector, or the squared vector magnitude (SVM). This quantity and other similar quantities are used later in the steps of the inventive method.

In flow chart element 38, a template vector slot having an index value of q is selected for comparison. For each detected heartbeat, the initial value of index q is 1, but as will be seen, method step 38 will "operate" Q times during the categorization of the detected heartbeat represented by vector $F(t_D)$. Flow chart decision element 40 determines if slot q contains a template vector $F_q$. If slot q does not contain a vector (a "Yes" decision in element 40), empty-slot index $q_E$ is set to q in flow chart element 42, and slot index q checked against Q in flow chart decision element 44 to see if any slots remain to be compared with vector $F(t_D)$. If the current value q of the slot index is less than the total number of slots Q, slot index q is incremented in flow chart element 46, and process 10B returns to flow chart element 38 to continue heartbeat categorization. (A "Yes" decision in flow chart element 44 will be discussed later in this detailed description of FIG. 2.)

At flow chart element 40, when a template is found in slot q, template vector $F_q$ and previously-computed $SVM_q$ (computed in element 36 during a previous heartbeat categorization cycle) are available for the comparison of the heartbeat at time $t_D$. Process 10B then proceeds with such comparison by computing a dot product $DP_q = F(t_D) \cdot F_q$ and a quantity $SCDA_q$ in flow chart elements 48 and 50, respectively. $SCDA_q$ is herein called the signed squared cosine difference angle between template vector $F_q$ and vector $F(t_D)$ associated with the detected heartbeat. In flow chart element 50, the computed terms $DP_q$, $SVM_q$ and $SVM_D$ are used to compute $SCDA_q$:

$$SCDA_q = \text{sgn}(DP_q) * DPq * DP_q / (SVM_D * SVM_q)$$

where the * symbol indicates multiplication. Thus, the magnitude of the quantity $SCDA_q$ is the square of the cosine of the angle $\theta_q$ between vector $F(t_D)$ and vector $F_q$, and the sign of $SCDA_q$ is the sign of the cosine of the angle $\theta_q$. As can be seen from the above expression for $SCDA_q$, $SCDA_q$ is indicative of how closely aligned vector $F(t_D)$ is with template vector $F_q$ or how small the angle between the two vectors is. In this embodiment, the quantity $SCDA_q$ is being used as a computational convenience to find the angle $\theta_q$ without the need for computing square roots and inverse cosines of quantities. Of course, any other algebraic formulations may be used to determine the relative alignment of vectors $F(t_D)$ and $F_q$.

The categorization of a heartbeat is based on the relative alignment of vector $F(t_D)$ with template vectors $F_q$. If two vectors are fully aligned, the angle $\theta_q$ between the two vectors is 0° and cosine of $\theta_q$ is 1. If angle $\theta_q$ is within a preset threshold angle $\theta_L$, the detected heartbeat associated with vector $F(t_D)$ is categorized as being similar to the heartbeat associated with template vector $F_q$. In the embodiment of FIG. 2, the comparison of angle $\theta_q$ with a preset threshold angle $\theta_L$ is done by comparing $SCDA_q$ with a limit value $SC_L$ which defines the magnitude of angle $\theta_q$ such that $F(t_D)$ is in the region of template vector $F_q$. For example, if a preset threshold angle $\theta_L$ of 25° is being used as such a threshold angle, $SC_L = \cos^2(25°$ or $SC_L \approx 0.8214$.

In the embodiment of FIG. 2, the value of $SC_L$ is the same for each template vector. In other embodiments, the values of $SC_L$ associated with each of the template vectors may differ depending on the features of the various heartbeats associated with the template vectors.

In flow chart elements 52 through 58, categorization process 10B determines for each detected heartbeat (1) what the maximum value of $SCDA_q$ is and (2) whether or not vector $F(t_D)$ is within the threshold angle $\theta_L$ of the template for which $SCDA_q$ is maximum. Process 10B proceeds to flow chart decision element 52 in which the computed value of $SCDA_q$ is compared with the value of the quantity $SC_M$. $SC_M$ is the maximum value of $SCDA_q$ for all values of q for which values of $SCDA_q$ have been computed during the categorization of a detected heartbeat. The highest possible value of $SCDA_q$ is, of course, 1 which indicates that $F(t_D)$ and $F_q$ are precisely aligned with each other (angle $\theta_q = 0°$), and the lowest possible value for $SCDA_q$ is −1 indicating that $F(t_D)$ and $F_q$ are pointing in precisely opposite directions (angle $\theta_q =$) 180°. During initialization at step 34, $SC_M$ was set to −1 so that all larger values of $SCDA_q$ are found as the sequential operations of categorization process 10B proceed.

If in decision element 52 $SCDA_q$ is found to be greater than $SC_M$, $SC_M$ is given the current $SCDA_q$ in flow chart element 54, and $q_M$, the index of the template vector which corresponds to $SC_M$, is given the value of the current index q in flow chart element 56. Process 10B then proceeds to flow chart decision element 44 in which current index q is compared with the total number of template slots Q. If in decision element 52 $SCDA_q$ is found not to be greater than $SC_M$, process 10B also proceeds to flow chart decision element 44.

In flow chart decision element 44 as described above, slot index q is checked against Q to see if any slots remain to be compared with vector $F(t_D)$. If q is not equal to Q, then the value of index q is incremented by 1 in flow chart element 46, and categorization process 10B loops back to flow chart element 38 to begin comparison of vector $F(t_D)$ with another template vector $F_q$. If q=Q in flow chart decision element 44 (i.e., the last template vector has been compared to $F(t_D)$ and $SC_M$ and $q_M$ have been identified for $F(t_D)$), process 10B proceeds to determine whether vector $F(t_D)$ is within preset threshold angle $\theta_L$ of template vector $F_M$ ($F_M$ is $F_q$ for q=$q_M$). This determination is done by comparing $SC_M$ with $SC_L$ (as described above) in flow chart element 58. If $SC_M$ is greater than $SC_L$, then vector $F(t_D)$ is within threshold angle $\theta_L$ of template vector $F_M$, and the count $C_M$ ($C_M$ is $C_q$ for q=$q_M$) of heartbeats in the category defined by $F_M$ is increased by 1 in flow chart element 68.

However, if $SC_M$ is not greater than $SC_L$, then process 10B has found that there is no template vector $F_q$ to which $F(t_D)$ is similar, and in this embodiment, $F(t_D)$ is then set as a new template vector if there is an empty template slot $q_E$ still available. Flow chart element 60 determines if a template slot is available ($q_E \neq 0$). If an empty template slot is available, vector $F(t_D)$ is set as template vector $F_E$ ($F_E$ is $F_q$ for q=$q_E$) as shown in flow chart element 62, and this new template category is given a count $C_E$ of 1 ($C_E$ is $C_q$ for q=$q_E$) in flow chart element 64. After either counting vector $F(t_D)$ in an existing template category (flow chart element 68) or in a newly-created template category (flow chart elements 62 and 64), heartbeat categorization process 10B proceeds to flow chart element 66 in which process 10B waits for the next heartbeat to be detected in process 10A.

If in flow chart decision element 60 no empty template slot is found, an empty template slot is created in flow chart element 61 and categorization process 10B continues to flow chart element 62. The example of FIGS. 6A-13F described in detail below is shown using a value of Q (the maximum number of heartbeat categories or templates) of 8. In general, however, the value of Q may be much larger than 8. Since modern computers operate at very high speeds and have essentially unlimited memory, the delay in performing numerous comparisons in categorization process 10B is insignificant, and setting Q to be quite large has little effect on operation of the method and avoids losing information about heartbeats caused by storing only a limited number of templates.

In the event that Q is not set high enough (an "N" result in flow chart decision element 60) for a patient being monitored and a heartbeat is encountered which requires that a new template be formed, flow chart element 61 may include steps which discard the template corresponding to the category which has the lowest number of counts and which has the longest period of time since the category has increased its count. Several other strategies are possible for the creation of a new empty slot $q_E$ in flow chart element 61 to deal with such a situation, but as mentioned above, setting Q to be large enough to avoid encountering needing to discard a template is a simple approach.

Factors which affect the number of template vectors (heartbeat categories) which may be used are, among other factors, the length of time for which a patient is to be monitored, the amount of patient movement during monitoring, the use of different patient postures during monitoring, and the noise environment affecting the ECG signals. Also affecting the appropriate value of Q is the selected value for $SC_L$. Smaller regions (smaller $\theta_L$) around template vectors mean that Q will likely need to be higher. In general, however, it is expected that for patients having a variety of ectopic heartbeats, the number of categories is still quite limited since the morphology of a heartbeat is determined by its trigger source within the heart, and thus heartbeats of the same morphology result from triggers occurring at the same points in the heart.

Many other logical strategies for filling template slots, assessing angle θ between vectors, and other parts of the logical flow of the embodiment of FIGS. 1-4 are possible within the scope of the inventive method. For example, the embodiment of FIG. 2 fills template slots beginning with slot Q (Q being the highest slot index) and then fills the highest available empty template slot when another vector is found to be a new template vector. Thus, if any empty slots are available, they will have lower slot index values than any filled template slot. It is not a limitation of this invention that the order in which slots are filled begin with the highest slot number.

FIG. 3 is a schematic block diagram of yet another portion of the embodiment partially illustrated in FIGS. 1 and 2. The block diagram of FIG. 3 is a flow chart of steps illustrating a process portion 10C of the embodiment that sets the threshold T which is compared in flow chart element 20 with sum $G(t_i)$ of the absolute velocities of the plurality of ECG signals, as illustrated in FIG. 1.

Point B in FIG. 3 indicates that this process portion 10C of the embodiment of the inventive process proceeds from point B of FIG. 1. Process 10C uses sum $G(t_i)$ of the absolute velocities of the plurality of ECG signals to adjust threshold T every preset time period of $t_m$ seconds based on $G(t_i)$, refractory timer ($timer_R$) from point C in FIG. 1, and a threshold timer ($timer_m$) running within process 10C. Flow chart element 69 is connected by a dotted line to indicate that it functions only upon start-up to initialize threshold T.

In flow chart decision element 70, the value of $G(t_i)$ is compared with $G_{max}$. $G_{max}$ is the maximum value of $G(t_i)$ during preset time period $t_m$ as determined by flow chart elements 70-78 and 84. ($G_{max}$ is determined during preset time period $t_m$, and if average signal levels drift, the estimate of the expected maximum value in this embodiment also changes due to the preset time period $t_m$ periodically renewing the value of $G_{max}$.) If $G(t_i)$ is greater than $G_{max}$ in decision element 70, $G_{max}$ is updated with a new value, $G(t_i)$ in flow chart element 72 and threshold timer ($timer_m$) is decremented by $\Delta t$ in flow chart element 74. ($\Delta t$ in this embodiment is 1 msec.) If $G(t_i)$ is not found to be a new maximum in decision element 70, then threshold timer ($timer_m$) is decremented by $\Delta t$ in flow chart element 74. Threshold timer ($timer_m$) is checked to see if preset time period $t_m$ has elapsed ($timer_m=0$) in flow chart decision element 76. If $timer_m$ is not equal to 0 in decision element 76, process portion 10C is complete, and threshold T remains at its current value for the next comparison in flow chart element 20 of FIG. 1. Preset time period $t_m$ in the embodiment of FIGS. 1-4 is 2 seconds. Such a value for $t_m$ is not intended to be limiting; other values may be used. Higher values of $t_m$ slow the rate at which threshold T is adjusted but also reduce the risk that no heartbeat occurs within period $t_m$.

If preset time period $t_m$ has elapsed ($timer_m=0$) in decision element 76, threshold timer ($timer_m$) is reset to preset time period $t_m$ in flow chart element 78, and process portion 10C proceeds to adjust threshold T in flow chart elements 80, 82 and 86. In flow chart decision element 80, the value of refractory timer ($timer_R$) (from point C of FIG. 1) is compared with a preset detection failure time limit $t_L$.

The refractory timer (designated $timer_R$) measures the elapsed time since the last detected heartbeat. Two preset threshold time values are associated with refractory $timer_R$, preset refractory period $t_R$ and preset detection failure time limit $t_L$. These two threshold values provide two different functions. Preset refractory period $t_R$ serves to prevent false positive detections from occurring too soon after a heartbeat is detected. Preset detection failure time limit $t_L$ serves to monitor the overall detection process in the event that the detection process is failing (e.g., threshold T must be adjusted by a large amount because the signals have changed dramatically).

If $timer_R$ is greater than preset detection failure time limit $t_L$, threshold T is set to $G_{max}/2$ in flow chart element 86. If $timer_R$ is not greater than preset detection failure time limit $t_L$, threshold T is adjusted to $T=T+(G_{max}/2-T)/4$ where the values of T on the right side of the equation (and in element 82 in FIG. 2) represent the previous value of the threshold T. This equation is written in the form as used in computer coding, and such form is well-known by those skilled in the art of computer programming. (This is also true in other elements such as 46 and 48.) After new values for threshold T have been set in flow chart elements 82 or 86, $G_{max}$ is reset to 0 in flow chart element 84 since $timer_m$ has been reset in element 78 and the new value for threshold T is provided to process portion 10A in FIG. 1, point D. Preset detection failure time limit $t_L$ is 5 seconds in the embodiment of FIGS. 1-4. Such a value for $t_L$ is not intended to be limiting to the scope of the invention; other values may be used.

Figure 5:
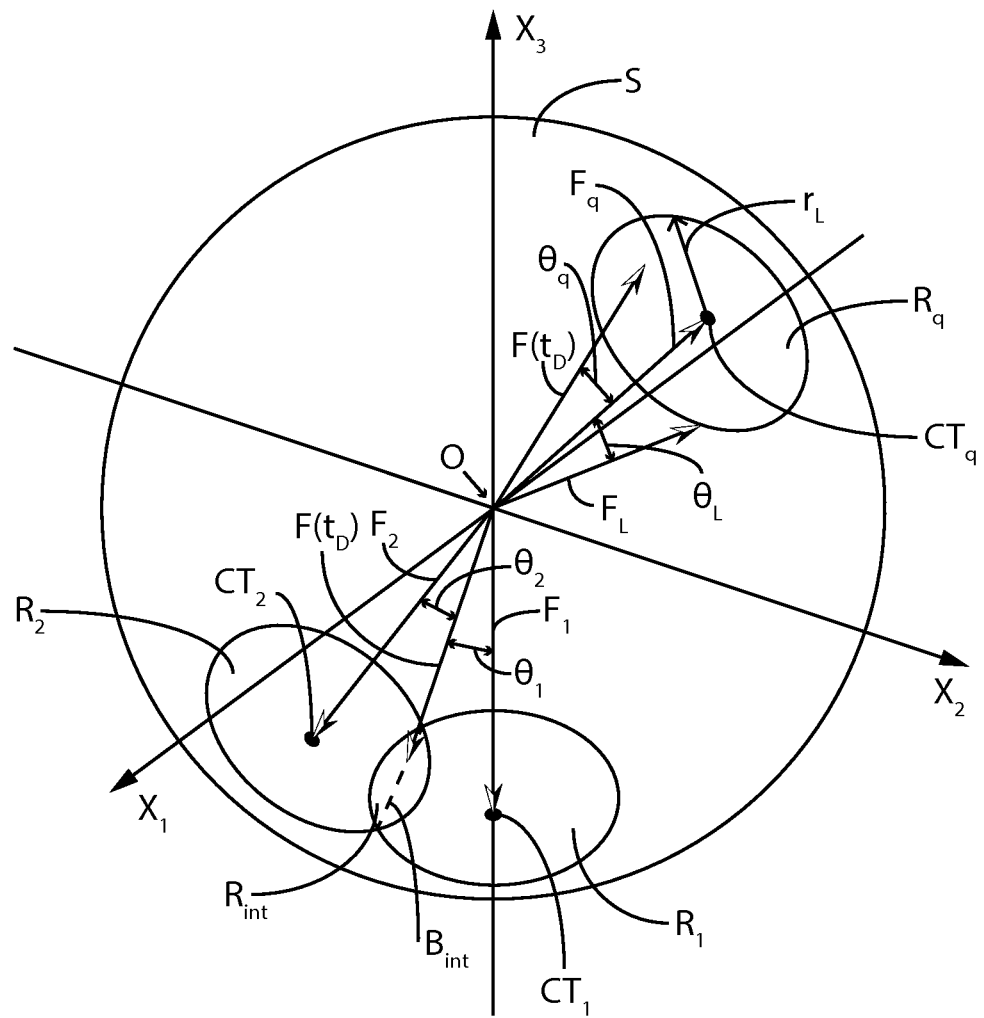
FIG. 5 is a drawing depicting a vector 3-space to illustrate the vector relationships employed in the inventive method.

FIG. 5 is a drawing depicting an N=3 vector space to illustrate the vector relationships employed in the inventive method. (Spaces for N>3 are of course not able to be drawn, but the concepts illustrated in FIG. 5 apply to methods employing greater than three selected ECG signals.) The elements of the drawing of FIG. 5 are employed as a means of illustration. For example, sphere S has no significance within the inventive method and is used here as a convenient way to illustrate a region $R_q$ subtended by a category represented by vector template $F_q$. Sphere S is centered around the origin O of a set of axes $[X_1, X_2, X_3]$ representing three directions in the 3-space and corresponding to three selected ECG signals. In FIG. 5, these axes are shown as an orthogonal set, but the selected ECG signals may not be "orthogonal" in a strict mathematical sense for the inventive method to be employed.

Drawn on the surface of sphere S is region $R_q$ which is centered around template vector $F_q$. Region $R_q$ has a radius of $r_L$ which results from the preset threshold angle $\theta_L$ and limit value $SC_L$ of $SCDA_q$ as described above. (In the embodiment of FIGS. 1-4, $\theta_L=25°$.) A vector $F_L$ is shown to illustrate one vector of a set of template vectors which are at the threshold limit angle $\theta_L$ for template vector $F_q$. A vector $F(t_D)$ representing a detected heartbeat at time $t_D$ which may be categorized as being in heartbeat category q since its angle $\theta_q$ is less than $\theta_L$. This heartbeat would be categorized as belonging to category q if its value of $SCDA_q$ was the maximum value $SC_M$ among all values of $SCDA_q$ as in the embodiment of FIGS. 1-4. FIG. 5 also illustrates this portion of the embodiment. At the lower portion of sphere S are two intersecting region $R_1$ and $R_2$ associated with template vectors $F_1$ and $F_2$, respectively. (The fact that these two regions are shown nearly 180° from region $R_q$ is unimportant. $R_1$ and $R_2$ are used only for illustration and are not related in any way to $R_q$.) As shown, it is possible that template vectors may have regions which overlap. In FIG. 5, this region of overlap is called $R_{int}$, and a boundary line $B_{int}$ marks the line along which the angles $\theta_1$ and $\theta_2$ between a heartbeat vector $F(t_D)$ ending along line $B_{int}$, are equal. With the precision of modern computers, the likelihood of a heartbeat vector ending precisely along line $B_{int}$, is extremely small, and if it occurs, placing $F(t_D)$ in either one of the heartbeat categories is an acceptable strategy. All other heartbeat vectors $F(t_D)$ ending in $R_{int}$ are categorized according to which angle $\theta_1$ and $\theta_2$ is the smallest, as set forth in the categorization process of FIG. 2.

Figure 6A:
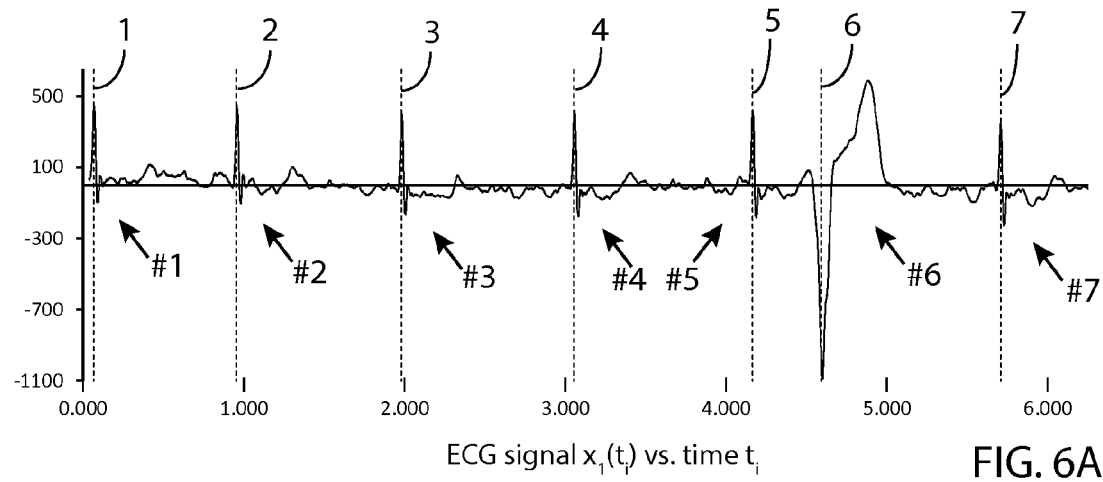
FIGS. 6A-6C show representative portions just over 6 seconds long of a set of three digitized ECG signals, sampled at 1,000 samples per second (sps).

FIGS. 6A-11D present an example of the operation of the embodiment of FIGS. 1-4. FIGS. 6A-6C show representative portions just over 6 seconds long of a set of three digitized ECG signals $[x_1(t_i), x_2(t_i), x_3(t_i)]$, sampled at 1,000 sps by A/D converters 12 (FIG. 1). (The precision of the digitized data in this example is 1 microvolt.) In the example, $x_1(t_i)$ is a digitized signal from an ECG standard lead II, $x_2(t_i)$ is a digitized signal from an ECG standard lead $V_1$, and $x_3(t_i)$ is a digitized signal from an ECG standard lead $V_5$. Over the same time period as in FIGS. 6A-6C, FIGS. 7A-7C show computed velocities $[f_1(t_i), f_2(t_i), f_3(t_i)]$ of the digitized ECG signals in FIGS. 6A-6C as computed in filters 14 in FIG. 1, and FIGS. 8A-8C show the absolute velocities $[g_1(t_i), g_2(t_i), g_3(t_i)]$ of the digitized ECG signals of FIGS. 6A-6C as generated in flow chart elements 16 in FIG. 1.

Figure 6B:
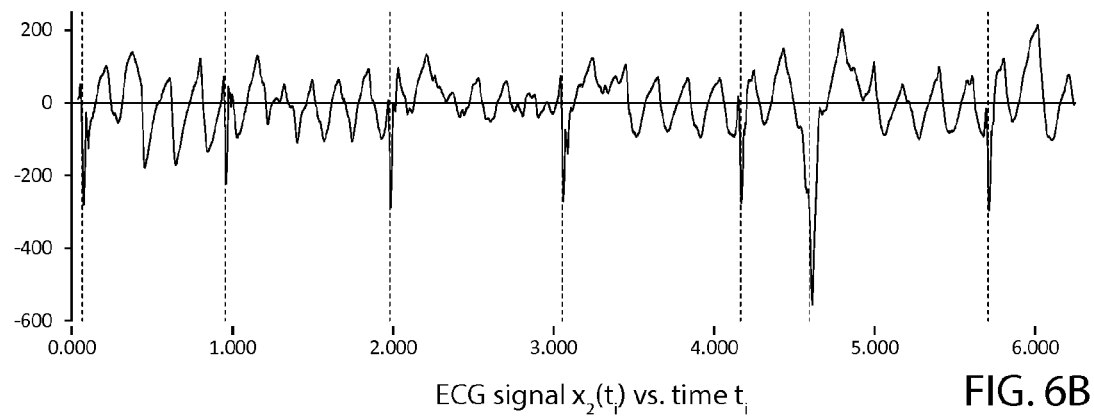
Figure 6C:
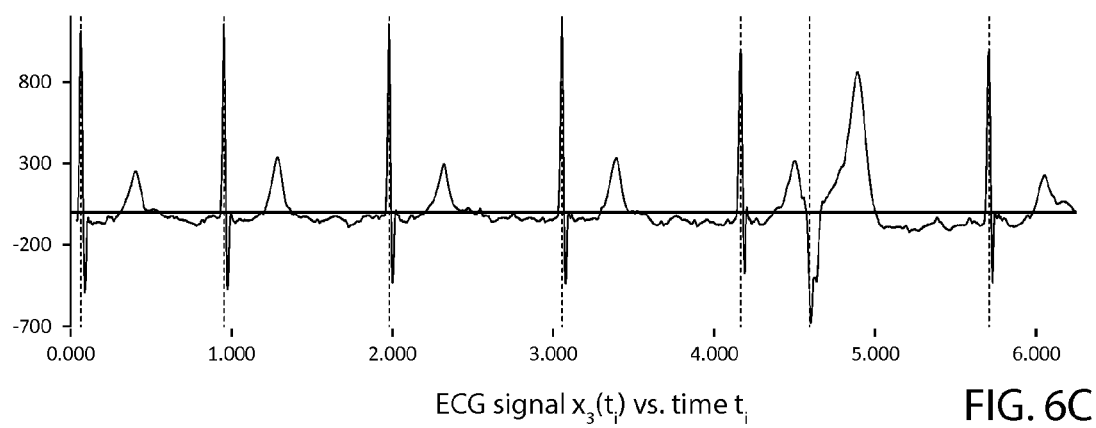
Figure 7A:
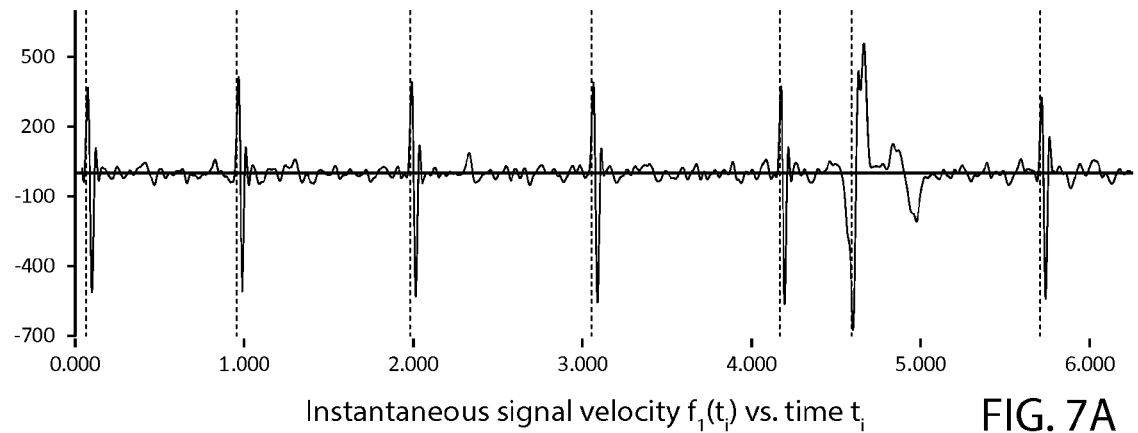
FIGS. 7A-7C show the velocities of the digitized ECG signals of FIGS. 6A-6C.
Figure 7B:
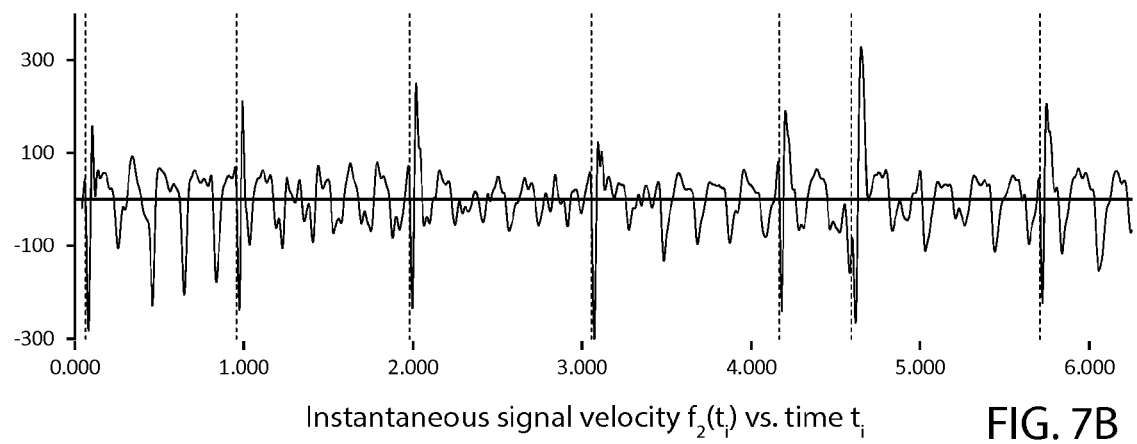
Figure 7C:
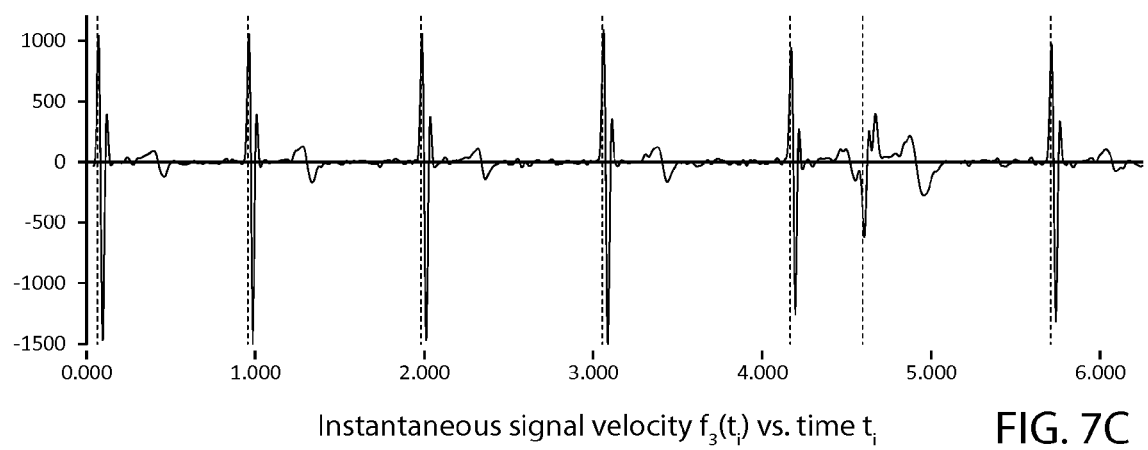
Figure 8A:
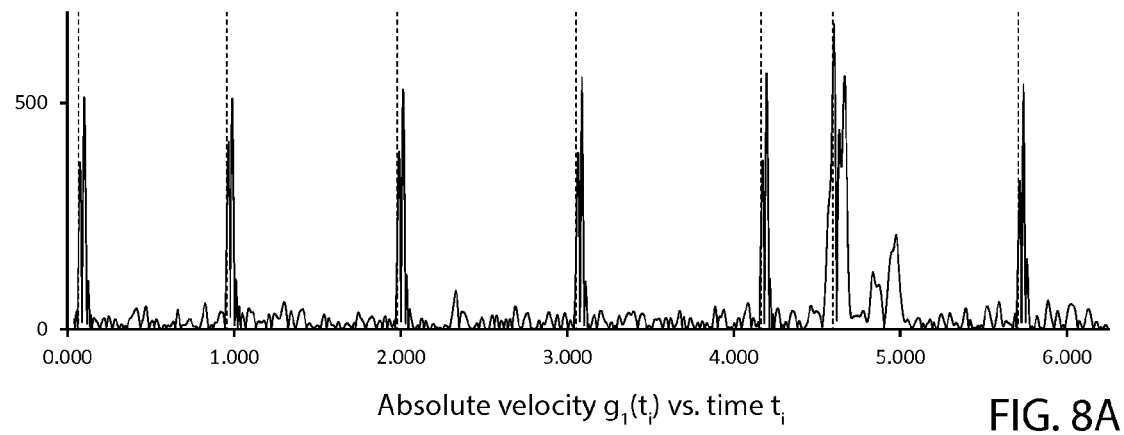
FIGS. 8A-8C show the absolute velocities of the digitized ECG signals of FIGS. 6A-6C.
Figure 8B:
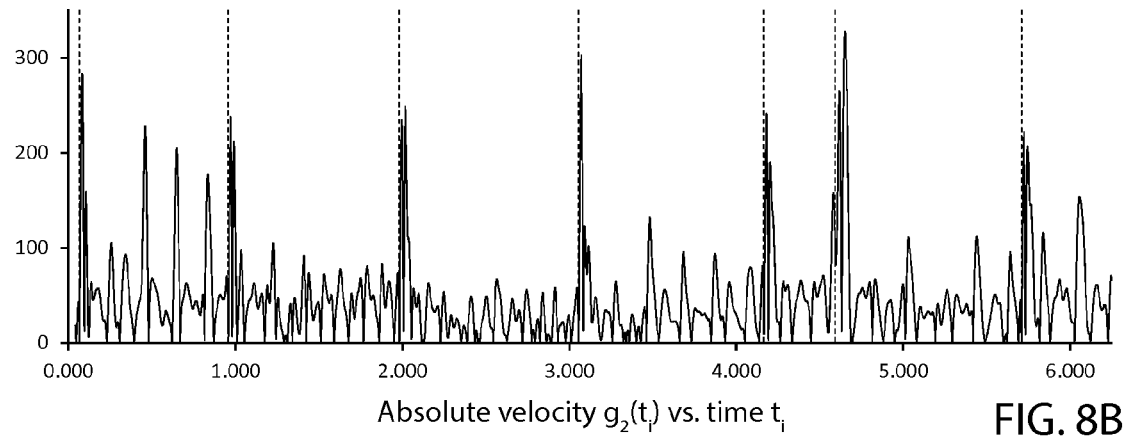
Figure 8C:
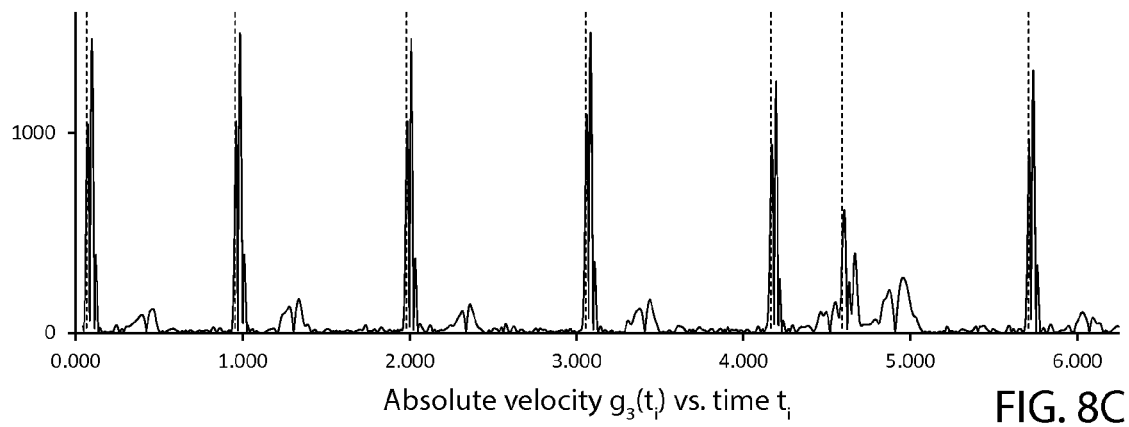
Figure 9A:
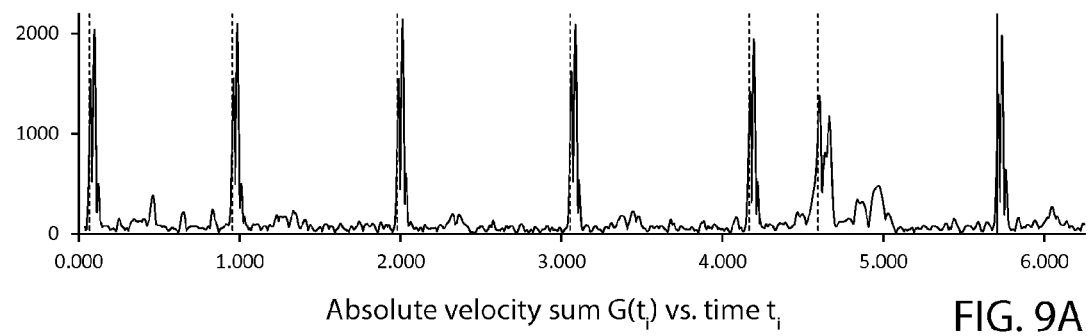
FIGS. 9A-9D show the sum (FIG. 9A) of the absolute velocities of FIGS. 8A-8C, the running maximum value (FIG. 9B) of the sum over contiguous 2-second periods, a threshold T (FIG. 9C) to which the sum is compared during heartbeat detection, and the values of a refractory timer (FIG. 9D) during the time period of FIGS. 6A-6C.
Figure 9B:
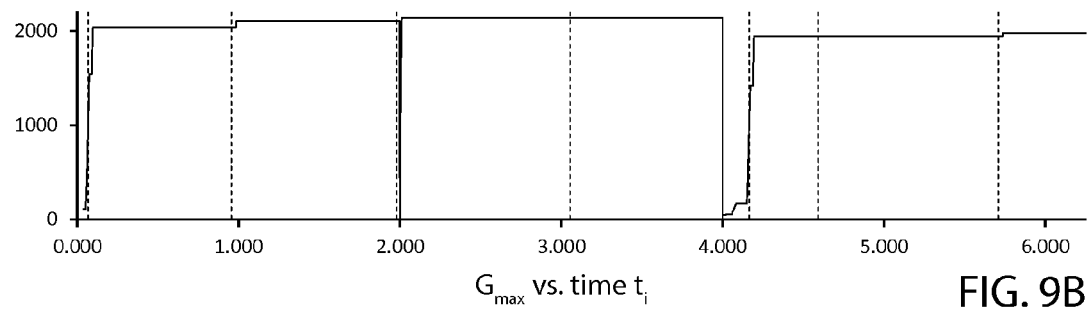
Figure 9C:
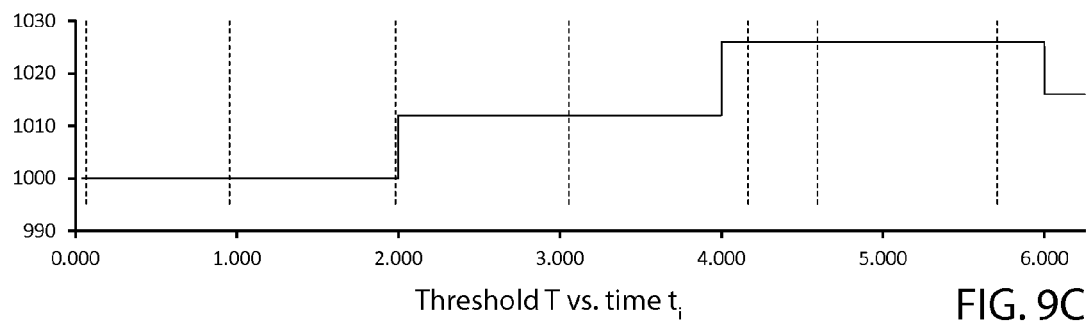
Figure 9D:
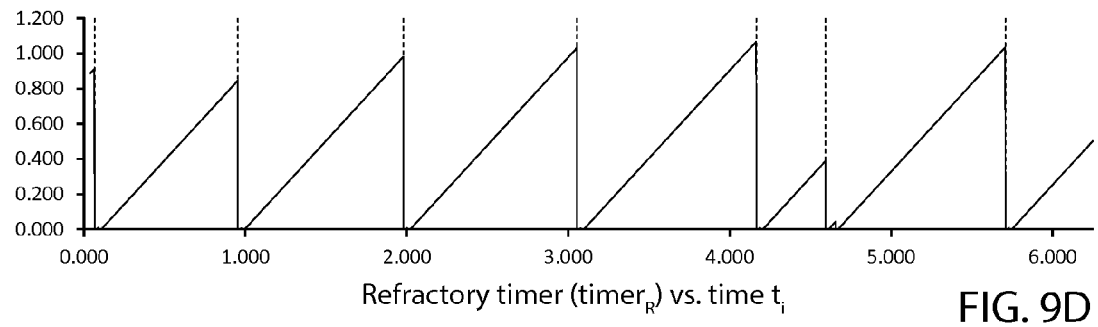

FIGS. 9A-9D show the sum $G(t_i)$ (FIG. 9A) of these absolute velocities, the running maximum value $G_{max}$ (FIG. 9B) of sum $G(t_i)$ over contiguous 2-second periods ($t_m$=2 seconds), threshold T (FIG. 9C) to which sum $G(t_i)$ is compared in flow chart element 20 during heartbeat detection, and the values of the refractory timer (timer$_R$) (FIG. 9D) during the time period of FIGS. 6A-6C. Threshold T is initialized in flow chart element 69 (see FIG. 3) to a value of 1000.

Each of FIGS. 6A-9D also show, with dotted vertical lines, the seven detection times t, as determined in the ECG signal data of the example. The dotted lines 1-7 indicate heartbeat detection times for heartbeats #1-#7, respectively. (Heartbeat reference numbers #1-#7 and heartbeat detection times 1-7 are only shown in FIG. 6A to reduce clutter in the figures. Each such figure is scaled identically so that heartbeats and detection times are easily identified.) In the example, heartbeats are detected at 0.066 seconds, 0.954 seconds, 1.980 seconds, 3.054 seconds, 4.165 seconds, 4.593 seconds, and 5.708 seconds. (These times are relative to the time axis origin chosen for the example and are not actual run times in the ECG data. The 6.25-second time period was simply chosen for this illustration of the inventive method.)

The characteristics of the ECG data in this example are those of the ECG of an atrial flutter patient, and the rapid oscillations particularly evident in $x_2(t_i)$ (lead $V_1$) are not signal noise. These oscillations are referred to as "flutter waves."

FIG. 10A shows a table of detection times of the seven detected heartbeats during the time period of FIGS. 6A-6C and values of computed velocity and squared vector magnitudes of the velocity vector $F(t_D)=\{f_1(t_D), \ldots, f_n(t_D)\}$ generated in the embodiment of FIGS. 1-4 for the selected signals in FIGS. 6A-6C. FIG. 10A also includes three template vectors and their squared vector magnitudes $SVM_D$ as generated within the example. (In this example, the velocities are in units of 62.5 microvolts/second. Thus for example, $f_1(0.066)$ =186 equates to 11.625 millivolts per second from 186*62.5=11,625.)

FIG. 10B is a table illustrating the computations made during the operation of the inventive method for the time period shown in FIGS. 6A-6C. Each of the rows of the table of FIG. 10B correspond to the detection time t, as indicated by the detected heartbeat number in the table of FIG. 10A. Thus, for detected heartbeat #1 at $t_D$=0.066 seconds and the associated heartbeat vector $F(t_D)$ and $SVM_D$, $DP_8$, the dot product of $F(t_D)$ with template vector $F_8$, is −200100, the squared cosine difference angle $SCDA_8$ is −0.1517, and the corresponding angle $\theta_8$ is 112.92°. Similar computations are seen in the table of FIG. 10B for comparisons of the heartbeat vectors #2-#7 with the template vectors as appropriate. In the example, a value for the limit of $SCDA_q$ ($SC_L$) of 0.8214 has been used, corresponding to a threshold angle $\theta_L$ of 25°. (For threshold angle $\theta_L$ of 25°, $SC_L$=) $\cos^2(25°$ or $SC_L \approx 0.8214$.)

For purposes of illustration, template vector $F_8$ shown in FIG. 10A has been assumed to have been generated by a heartbeat previous to the time period of the ECG data of FIGS. 6A-6C. Since the comparison of heartbeat #1 and template vector $F_8$ results in $SCDA_8$=−0.1517 ($\theta_8$ 113°), heartbeat #1 is not categorized as similar to the heartbeat which generated template vector $F_8$ and thus a new template vector $F_7$ is created.

Heartbeats #2 through #5 and #7 each are similar to heartbeat #1 as represented by template vector $F_7$ and are thus categorized. As seen in the table of FIG. 10B, heartbeat #6 is dissimilar to both of the heartbeats represented by template vectors $F_8$ and $F_7$ and thus a new template vector $F_6$ is created from heartbeat #6.

Figure 11A:
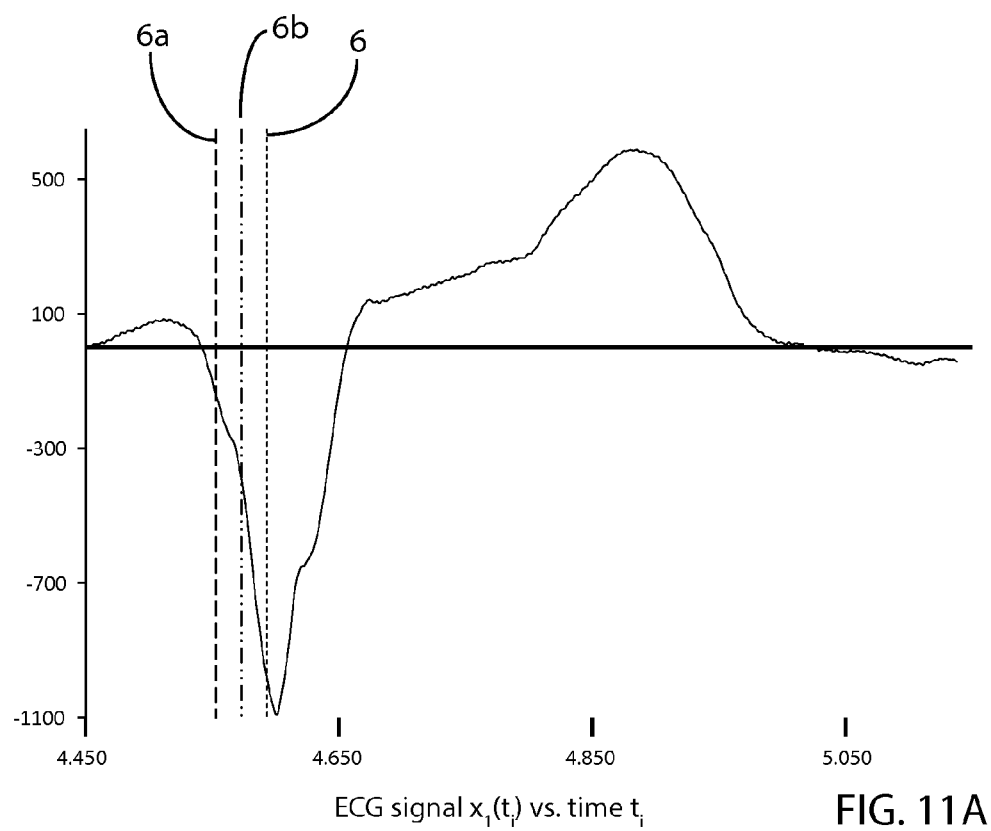
FIGS. 11A-11C show a portion of the ECG signals of FIGS. 6A-6C which include a single detected heartbeat.
Figure 11B:
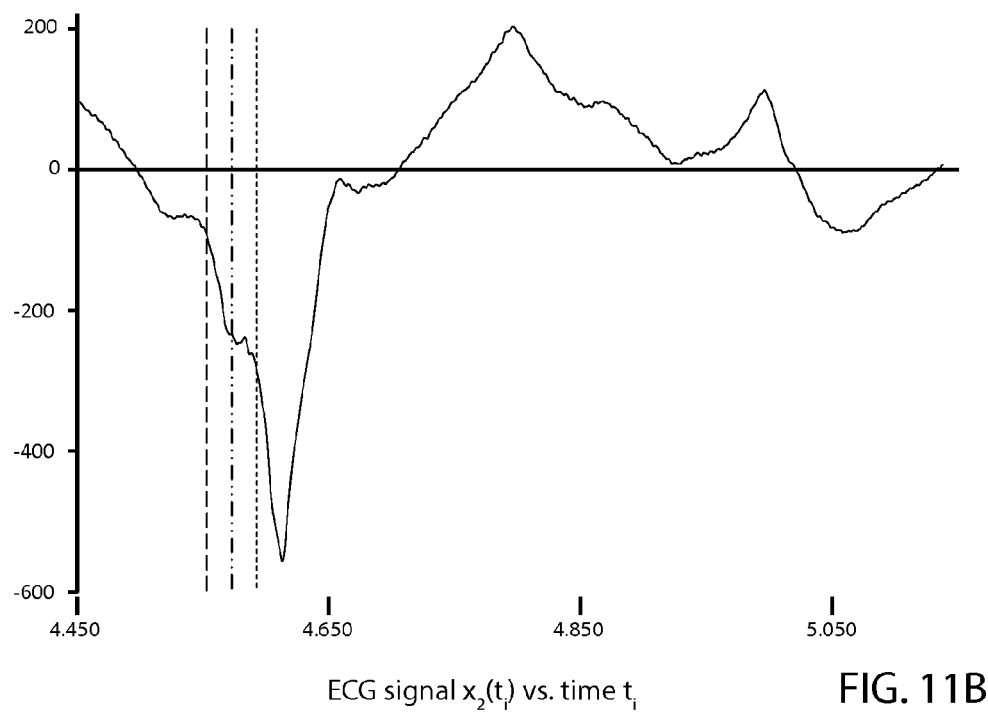
Figure 11C:
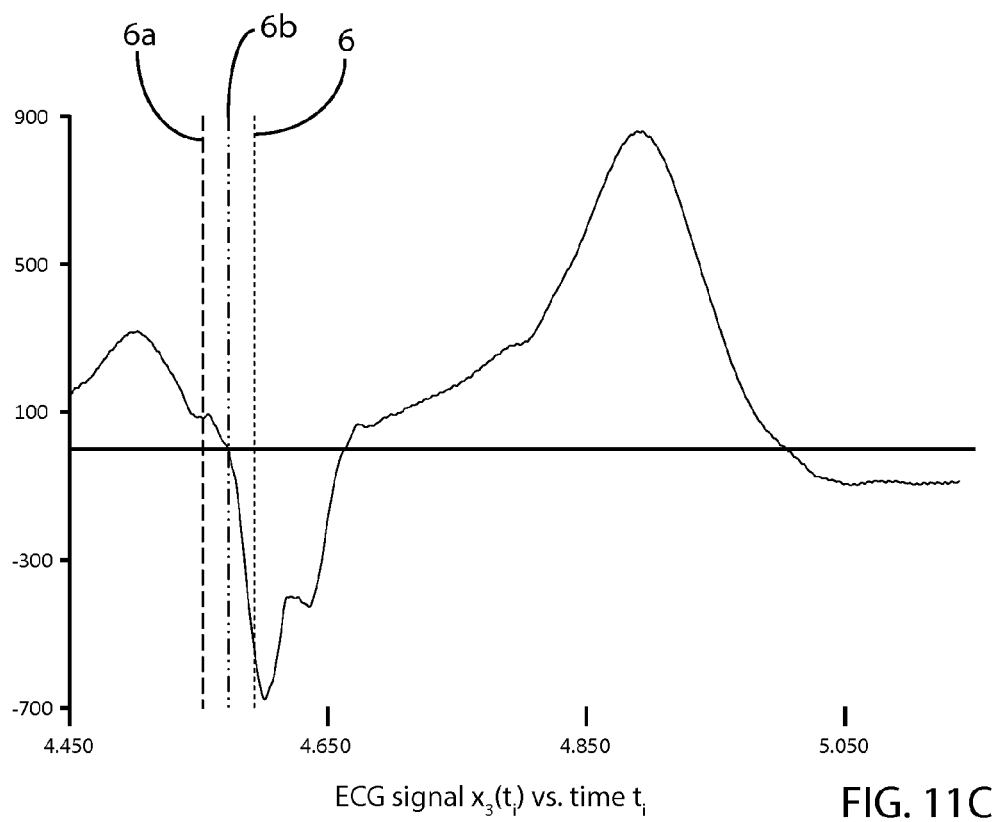
Figure 11D:
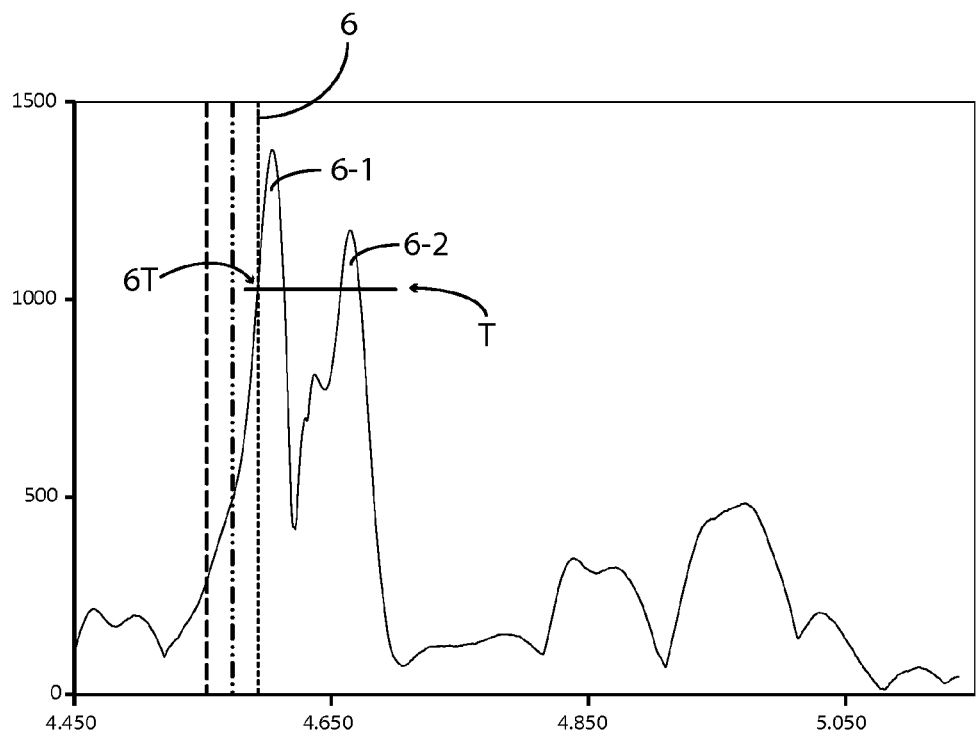
FIG. 11D shows the sum of the absolute velocities for the ECG signals of FIGS. 11A-11C.

Heartbeat #6 detected at 4.953 seconds is a premature ventricular contraction (PVC), and this beat is shown in further detail in FIGS. 11A-11D. FIGS. 11A-11C show the portion of the ECG signals of FIGS. 6A-6C which include single detected heartbeat #6. FIG. 11D shows the sum of the absolute velocities for the ECG signals of FIGS. 11A-11C. In FIGS. 11A-11D, detection time $t_i$=4.593 seconds is indicated by vertical dotted line 6 as in previous FIGS. 6A-9D. (Absolute velocity sum $G(t_i)$ intersects threshold T at $t_D$=4.593 seconds, at intersection 6T, and intersection 6T is marked by vertical dotted lines 6.) In addition, two other vertical lines with different dotted-line patterns are shown. Vertical line 6a is located at $t_i$=4.553 seconds, and vertical line 6b is located at $t_i$=4.573 seconds. (Vertical lines 6, 6a and 6b are only labeled in FIGS. 11A and 11C to reduce clutter in the figures.)

The time periods between line 6 and line 6b and between line 6b and line 6a represent the spans of the two boxcars of filters 14 (FIG. 1) which are used in this example to determine velocities $[f_1(t_i), f_2(t_i), f_3(t_i)]$ of the three selected, digitized ECG signals $[x_1(t_i), x_2(t_i), x_3(t_i)]$. Based on this embodiment by which velocities $[f_1(t_i), f_2(t_i), f_3(t_i)]$ are determined, the values of the velocity components which are computed are delayed 20 msec from the "actual" velocities of the ECG signals. In other words, the characteristics of the signal velocities by which the inventive method detects a heartbeat occur very early in the period of a heartbeat. In the case of heartbeat #6 in FIGS. 11A-11D, the features of the signals as they are at $t_i$=4.573 seconds (line 6b) are such that heartbeat #6 is detected. Note that detection occurs at $t_D$=4.593 seconds, not 4.573 seconds, due to the operation of the embodiment of FIGS. 1-4, but the physical signals being processed reach a state at $t_i$=4.573 seconds by which not only is a heartbeat detected but is able to be categorized with such information from early in the period of the heartbeat.

Referring to FIG. 11D which shows the sum $G(t_i)$ of absolute velocities $[g_1(t_i), g_2(t_i), g_3(t_i)]$ for the PVC (heartbeat #6), a second peak 6-2 in $G(t_i)$ occurs after a first peak 6-1. There are numerous values of $G(t_i)$ within peaks 6-1 and 6-2 which have values above threshold T, but each of these points occurs at a time well below preset refractory period $t_R$ of 120 msec. Along $G(t_i)$, the final point within peak 6-2 which is above threshold T occurs at t=4.671 seconds, 78 msec after the heartbeat detection at $t_D$=4.593 seconds. As described above, the main function of preset refractory period $t_R$ is to prevent false positive detections from occurring too soon after a detection.

Figure 12:
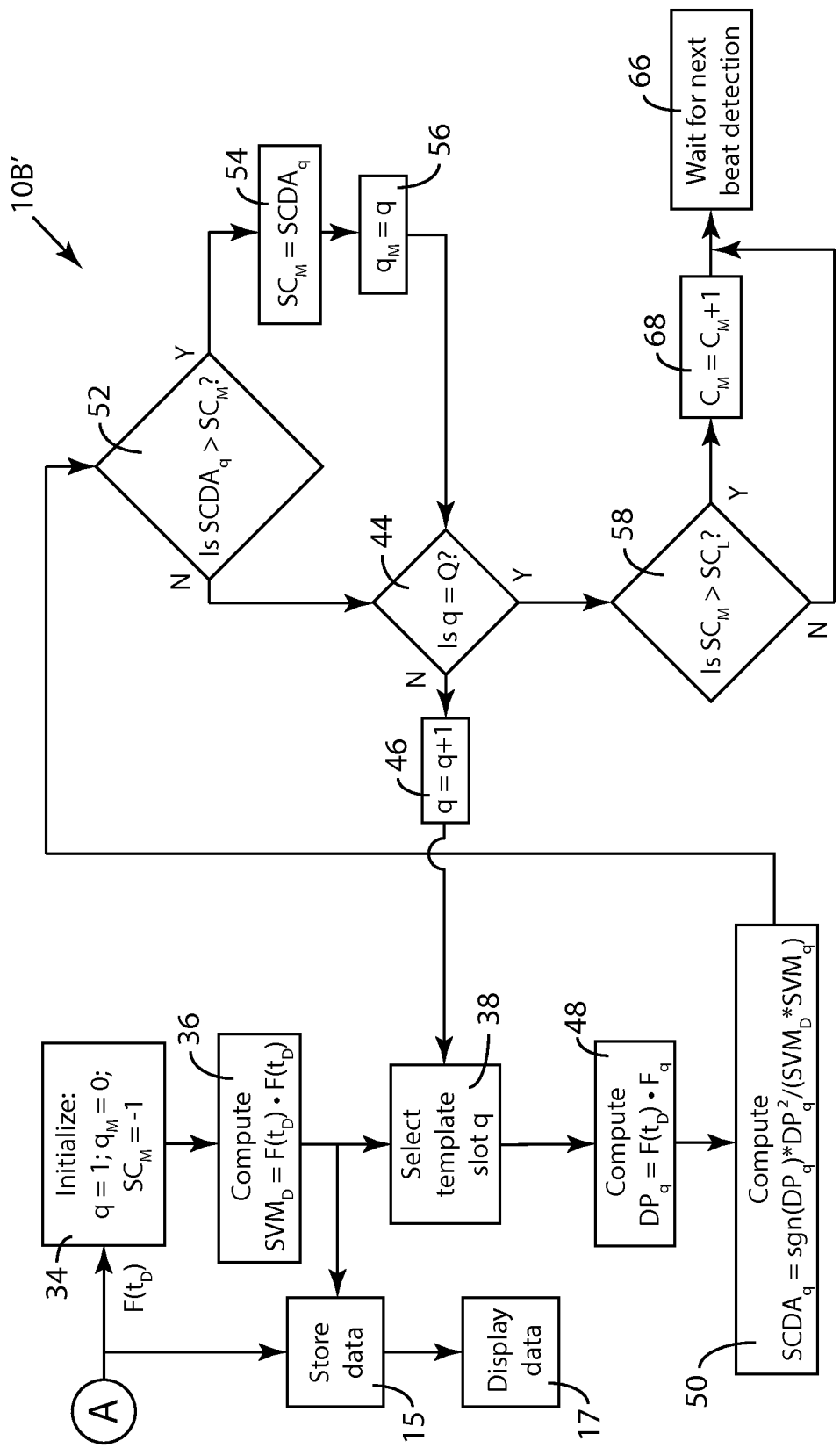
FIG. 12 is a schematic block diagram of an alternative embodiment of the heartbeat categorization portion of the inventive method for heartbeat detection.

FIG. 12 is a schematic block diagram of an alternative embodiment 10B' of the heartbeat categorization portion of the inventive method for heartbeat detection. Alternative embodiment portion 10B' replaces portion 10B of FIG. 2 and is combined with FIGS. 1 and 3-4 to form a complete alternative embodiment of the inventive method. The block diagram of FIG. 12 illustrates a process in which the template vectors to be compared with the vectors representing detected heartbeats are all preset vectors.

Comparing FIG. 12 with FIG. 2, alternative embodiment 10B' does not require the determination of empty template slot $q_E$ which occurs in flow chart decision element 40 and flow chart element 42. Further, the functions of adding a new template vector which occur in flow chart decision elements 60 and 61, and flow chart elements 62 and 64 are also not required. Alternative embodiment 10B' may also be modified to allow preset template vectors to be replaced (as in FIG. 2) if one or more of the preset vectors are found not to be useful during a monitoring procedure.

FIGS. 1-4 also represent an embodiment in which only a portion of the template vectors to be compared with the vectors representing detected heartbeats are preset vectors.

Figure 13B:
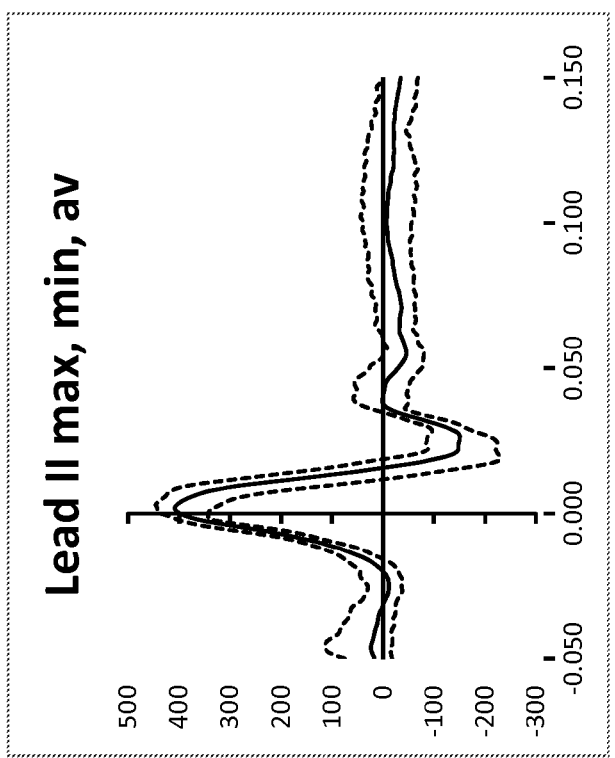
FIG. 13B shows, for the same time period as in FIG. 13A, the maximum, minimum and average values of $x_1(t_i)$.
Figure 13A:
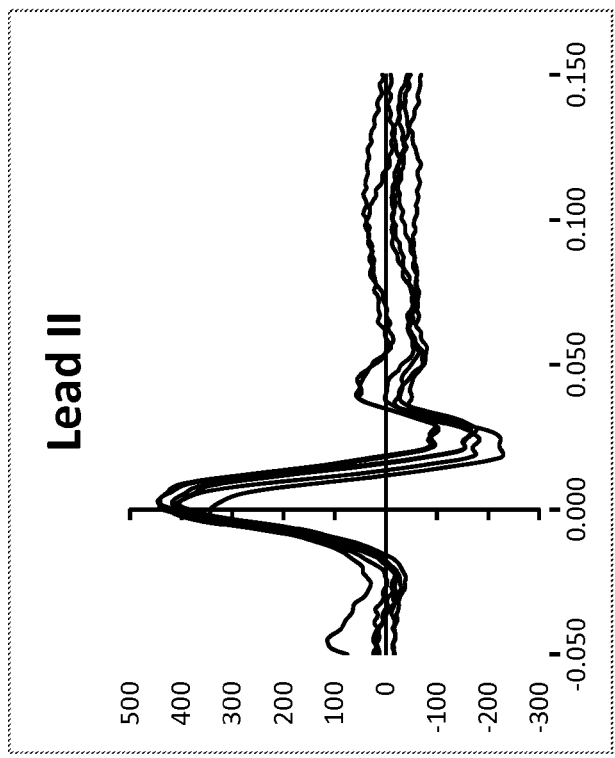
FIG. 13A shows the $x_1(t_i)$ signals for each heartbeat in the example of FIGS. 6A-10B which was detected and categorized as belonging to heartbeat category 7, with each detection time $t_D$ aligned at $t_i=0$ on the plot.
Figure 13D:
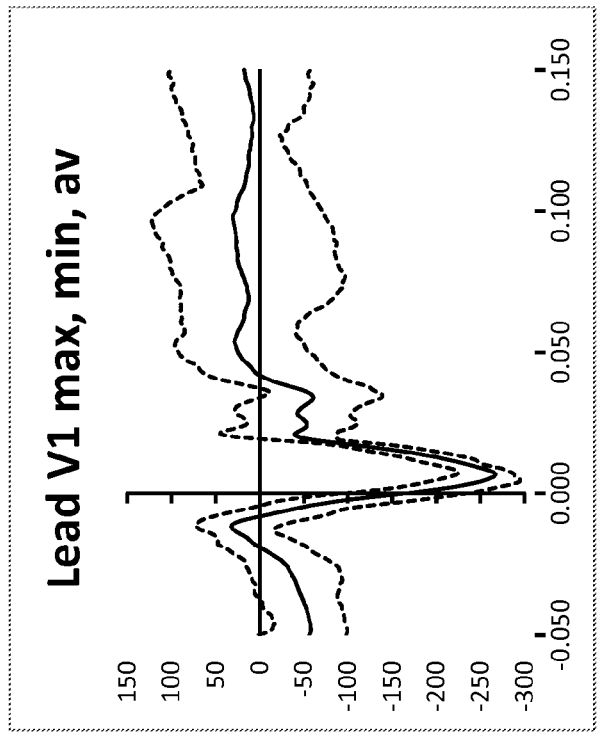
FIG. 13D shows, for the same time period as in FIG. 13C, the maximum, minimum and average values of $x_2(t_i)$.
Figure 13C:
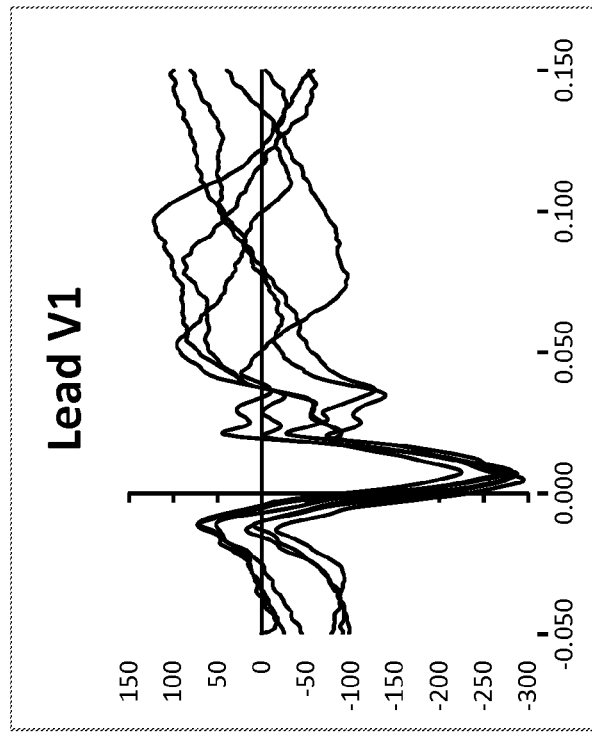
FIG. 13C shows the $x_2(t_i)$ signals for each heartbeat in the example of FIGS. 6A-10B which was detected and categorized as belonging to heartbeat category 7, with each detection time $t_D$ aligned at $t_i=0$ on the plot.
Figure 13F:
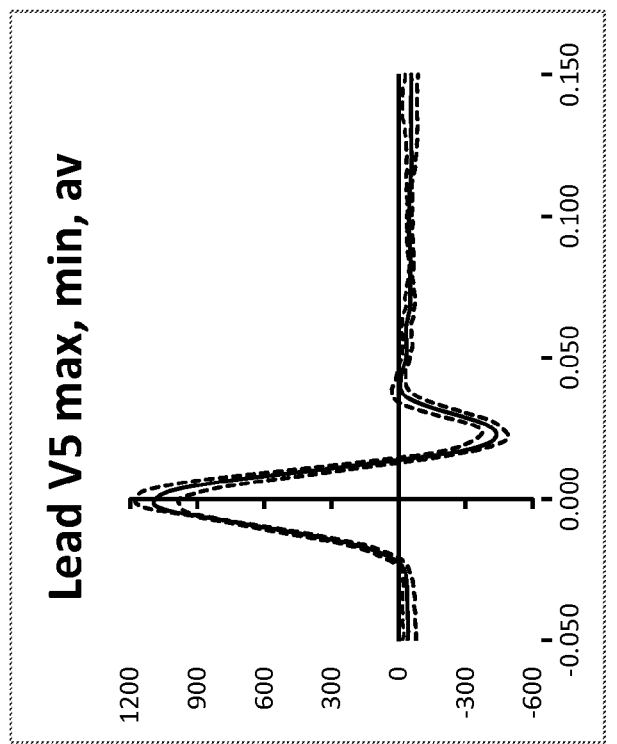
FIG. 13F shows, for the same time period as in FIG. 13E, the maximum, minimum and average values of $x_3(t_i)$.
Figure 13E:
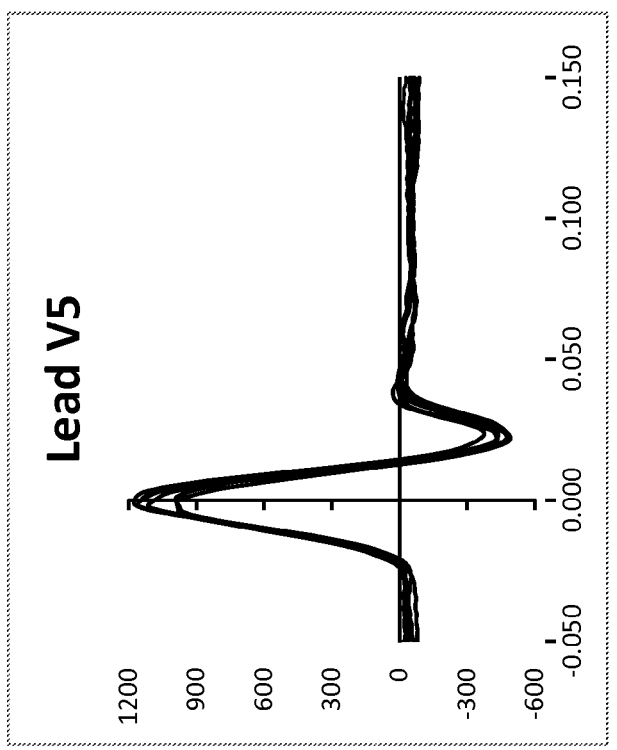
FIG. 13E shows the $x_3(t_i)$ signals for each heartbeat in the example of FIGS. 6A-10B which was detected and categorized as belonging to heartbeat category 7, with each detection time $t_D$ aligned at $t_i=0$ on the plot.

FIG. 13A shows the $x_1(t_i)$ signals for each heartbeat in the example of FIGS. 6A-10B which was detected and categorized as belonging to heartbeat category 7, with each detection time $t_D$ aligned at $t_i=0$ on the plot. FIG. 13B shows, for the same time period as in FIG. 13A, the maximum, minimum and average values of $x_1(t_i)$. The pairs of figures (FIGS. 13C-13D and 13E-13F) in similar fashion show the $x_2(t_i)$ and $x_3(t_i)$ signals, respectively. A user of the inventive method may wish to view the results of the method, such as on a computer display. One possible way in which results may be displayed include the superimposed traces of the individual selected ECG signals as illustrated in FIGS. 13A, 13C and 13E. By such a display the user can confirm that the heartbeats in a category indeed have similar morphology. A user may also confirm that a category represents a particular heartbeat morphology of interest. The specific morphology may be seen more clearly in the display of information such as is shown in FIGS. 13B, 13D and 13F. In such figures, an envelope containing all of the heartbeats in a category is shown by displaying the maximum and minimum values of the selected ECG signals as a function of time $t_i$ of all heartbeats in a category. This envelope is indicated by the dotted-line traces of such figures. This envelope is one such way of displaying a representative heartbeat.

Another way of showing a heartbeat representative of a category is to compute and display the average of all heartbeats in a category as a function time $t_i$. Such information is shown as the solid-line trace in FIGS. 13B, 13D and 13F. Other possible representative heartbeats are possible such as computing and displaying the median as a function of time $t_i$.

Figure 14:
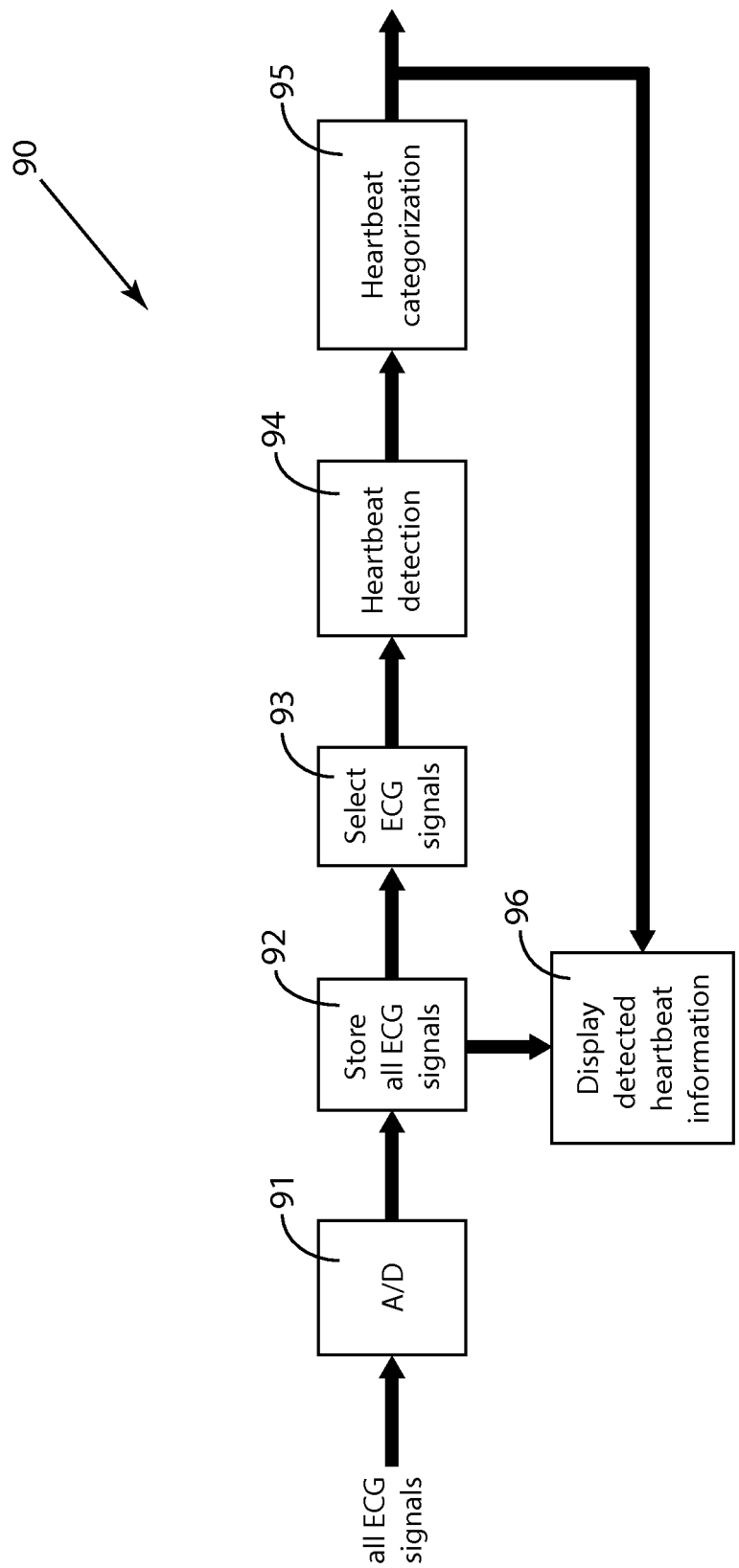
FIG. 14 is a high-level schematic block diagram of an embodiment of the inventive method in which all available ECG signals are digitized and stored and at least a portion of which are displayed.

FIG. 14 is a high-level schematic block diagram of an embodiment 90 of the inventive method in which all available ECG signals are digitized and stored and at least a portion of which are displayed. (The lines between the flow chart elements of embodiment 70 are shown as heavy lines to indicate that such lines may represent more than one ECG signal.) The ECG signals are digitized in flow chart element 91, and the digitized ECG signals are stored in available memory as represented by flow chart element 92. Flow chart element 93 represents the process of selecting ECG signals from among all the ECG signals, and flow chart elements 94 and 95 depict the steps of the inventive method to detect (94) and categorize (95) the heartbeats as described above in this application, such as by process portions 10A (and 10C) and 10B, respectively. Then flow chart element represent the step of displaying information descriptive of a detected heartbeat from the information stored in the step of flow chart element 92. For example, there may be a dozen or more ECG signals available, some of which may not be body surface signals, and many of these signals which are not among those selected and processed for detection and categorization may be displayed from storage to assist a user in the decision-making required during an interventional procedure.

Statistical studies on actual patient data from multiple patients have shown that comparison of the absolute velocity sum $G(t_i)$ against an adaptively-adjusted threshold T is a reliable detection method for heartbeats. Studies have also shown that the vector $F(t_D)$ is a reliable and robust measure by which to sort heartbeats into categories of heartbeats having similar morphology. The significance of this inventive method is that (1) heartbeats are detected early in the period of a heartbeat, (2) heartbeats are reliably categorized using measurements just at the instant ($t_D$) of detection rather than using a much larger amount of data related to the features of a heartbeat during its entire heartbeat period, and (3) categorization according to anatomical origin is facilitated by use of the earliest discriminating features of a heartbeat.

The value of $SC_L$, the limit value of $SCDA_q$, defines the region in N-space in which heartbeat vectors $F(t_D)$ must fall to be categorized as being similar to heartbeats in the category represented by template vector $F_q$. A larger value of $SC_L$ (smaller region subtended by the category) tends to increase the number of categories needed to categorize all of the heartbeats of a patient during a session of monitoring the patient's ECG.

Figure 15:
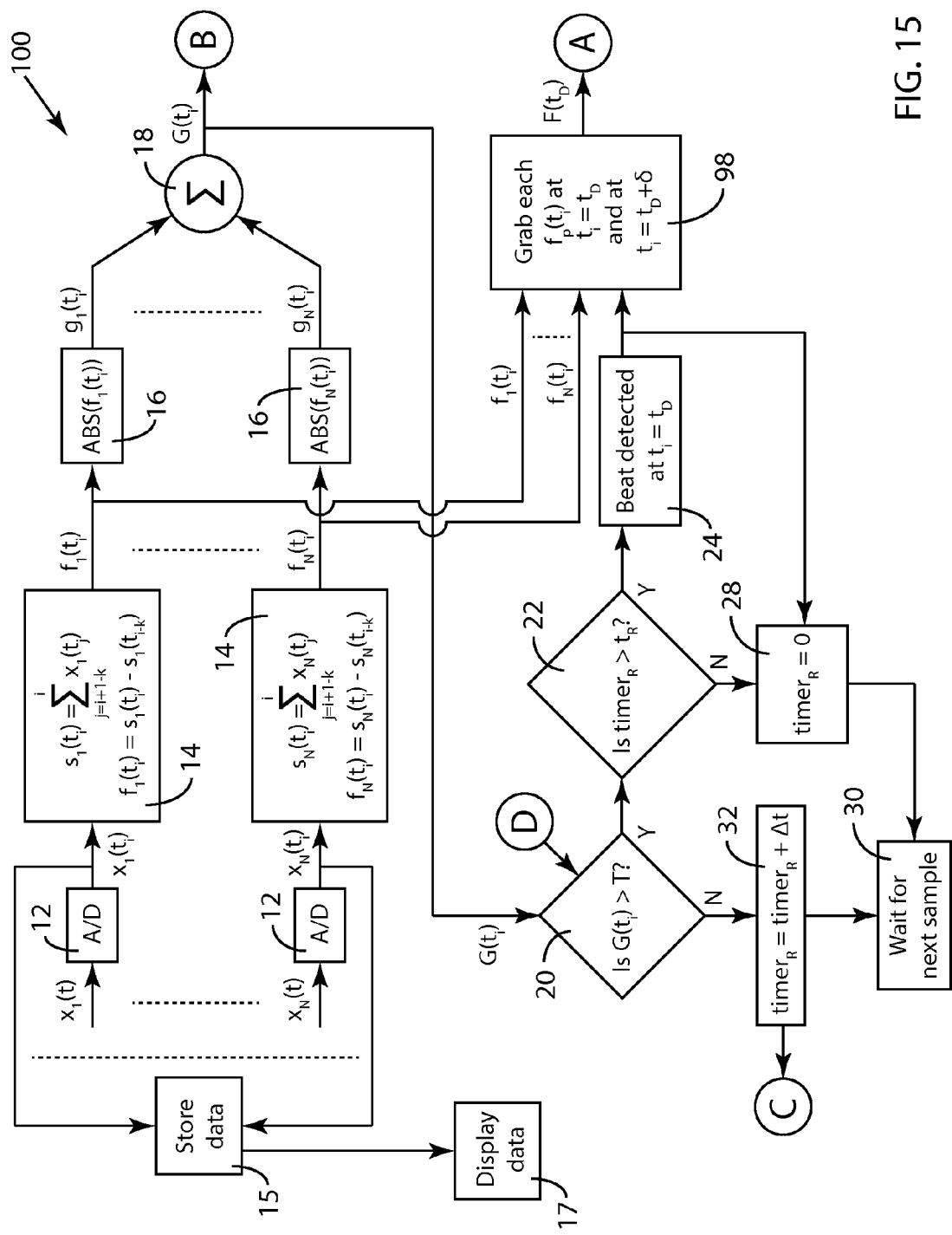
FIG. 15 is a schematic block diagram of an alternative embodiment of the heartbeat detection portion of the inventive method for heartbeat detection wherein after heartbeat detection, the vector representing a detected heartbeat is augmented with additional velocity components for categorization processing.

FIG. 15 is a schematic block diagram of an alternative embodiment 100 of the heartbeat detection portion of the inventive method for heartbeat detection wherein after heartbeat detection, vector $F(t_D)$ representing a detected heartbeat is augmented with additional velocity components for categorization processing. Embodiment 100 of FIG. 15 is identical to that of the embodiment of process portion 10A of FIG. 1 except that flow chart element 98 in FIG. 15 has replaced flow chart element 26 of FIG. 1.

In flow chart element 98, vector $F(t_D)$ is modified from that of flow chart element 26 in FIG. 1 such that vector f(tD) is now $$F(t_D)=\{f_1(t_D),\ldots,f_N(t_D),f_1(t_D+\delta),\ldots,f_N(t_D+\delta)\}$$

where $\delta$=a time period after heartbeat detection time $t_D$. In other words, vector $F(t_D)$ is now a vector associated with the heartbeat detected at time t, which has 2N components, the second set of which are the N velocities of the selected ECG signals at time $t_D+\delta$. In embodiment 100, vector $F(t_D)$ contains the N velocity components at detection time $t_D$ and N velocity components of the same ECG signals but measured at time $t_D+\delta$.

Figure 16A:
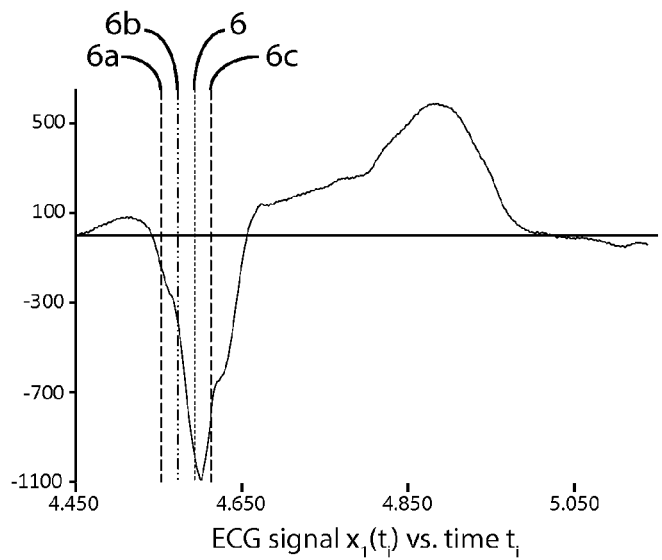
FIGS. 16A-16C are modified versions of FIGS. 11A-11C, showing a portion of the ECG signals of FIGS. 6A-6C which include a single detected heartbeat. The modifications in FIGS. 16A-16C for the example of FIGS. 6A-11D indicate the time at which additional velocity determinations are made, 20 milliseconds (msec) after a heartbeat is detected.
Figure 16B:
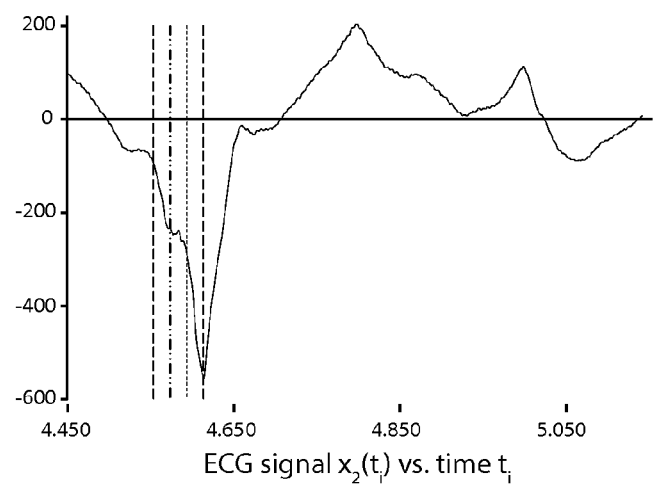
Figure 16C:
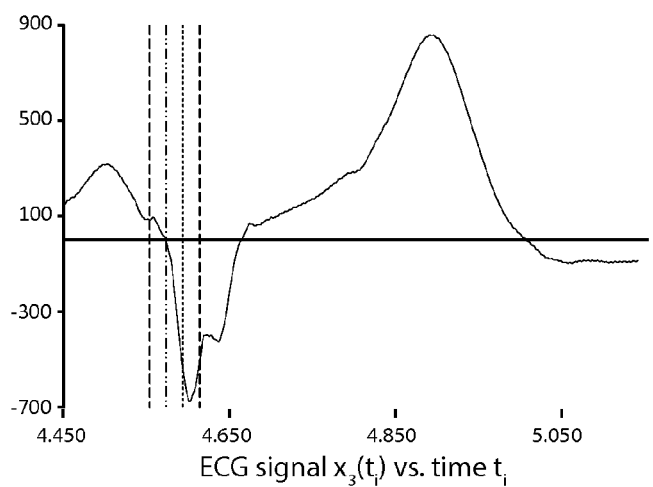

Adapting embodiment 100 to the example of FIGS. 6A-9D in which N=3, vector $F(t_D)$ now becomes $F(t_D)=\{f_1(t_D), f_2(t_D), f_3(t_D), f_1(t_{D+k}), f_2(t_{D+k}), f_N(t_{D+k})\}$ where k=20. Thus, the three additional velocity components of $F(t_D)$ are the velocities of the selected ECG signals measured one boxcar width k after detection time $t_D$. FIGS. 16A-16C are modified versions of FIGS. 11A-11C, showing a portion of the ECG signals of FIGS. 6A-6C which include a single detected heartbeat. The modifications in FIGS. 16A-16C for the example of FIGS. 6A-11D indicate the time at which additional velocity determinations are made, 20 msec after a heartbeat is detected. Vertical dotted line 6c is located at time 4.613 seconds, 20 msec after $t_D$=4.593 seconds for heartbeat #6.

As discussed above, in embodiment 100 for the example, vector $F(t_D)$ now has six velocity components instead of three. Categorization process 10B proceeds just as described above for the N=3 example. FIG. 17A is a table (similar to that of FIG. 10A) which shows detection times of the seven detected heartbeats during the time period of FIGS. 6A-6C and values of computed velocities and squared vector magnitudes of the velocity vector $F(t_D)=\{f_1(t_D),\ldots,f_n(t_D)\}$ generated in the alternative embodiment 100 of FIG. 15 (combined with FIGS. 2-4) for the selected ECG signals in FIGS. 6A-6C. FIG. 17A also includes four template vectors and their squared vector magnitudes as generated within this example. The heartbeat detection process of embodiment 100 is identical to that of process portion 10A, thus resulting in identical detected heartbeats #1-#7 as shown in FIG. 10A. FIG. 17A includes three additional columns which are the ECG signal velocities at $t_i=t_{D+k}$ (at $t_i=t_D+0.020$ seconds since k=20 samples and the sampling rate is 1,000 sps).

FIG. 17B is a table (similar to that of FIG. 10B) illustrating the computations made during the operation of this alternative embodiment during the time period shown in FIGS. 6A-6C. For this example, the value of preset threshold angle $\theta_L$ is 10°. The smaller value of preset threshold angle $\theta_L$ and the additional information provided by the second set of ECG signal velocities result in greater specificity of the categorization process.

In this brief (short time period of data) example, the alternative embodiment of the inventive method identified an additional heartbeat category characterized by heartbeat #5 (Template 6) while in the example summarized in FIG. 10B, heartbeat #5 was categorized as being similar to heartbeat #1 (characterized by Template 7).

Additional statistical studies on actual patient data have shown that the modified velocity vector $F(t_D)$ (having 2N components) improves the specificity of heartbeat categorization when compared with embodiment 10A of FIGS. 1-4. Such improvement in specificity is accomplished without applying smaller values for preset threshold angle $\theta_L$. In other words, adding a second velocity measurement into each velocity vector $F(t_D)$ yields similar improvements in categorization performance as tightening preset threshold angle $\theta_L$ for the single-velocity embodiment of the inventive method. In addition, the studies indicated that fewer but more precise templates were identified using embodiment 100 when compared with the embodiment 10A with a smaller preset threshold angle $\theta_L$.

FIG. 18A is a high-level schematic block diagram of an embodiment 110 of the inventive method for heartbeat categorization, illustrating that the inventive method utilizes a vector $F(t_C)$ for heartbeat categorization where $t_C$ is a categorization fiducial time at which the vector $F(t_C)$ is evaluated. In FIG. 18A, flow chart elements 114 and embodiment 10B" comprise a combined set of method steps 116 of the inventive method for heartbeat categorization which is independent of the method by which a heartbeat is detected and made available as an input (flow chart element 112) to the inventive method and the way in which categorization fiducial time $t_C$ is determined. Categorization fiducial time $t_C$, which may be provided by a number of sources, is used as the time at which vector $F(t_C)$ is evaluated in flow chart element 114.

FIG. 18B is a high-level schematic block diagram which is a modification to FIG. 18A, illustrating an embodiment 120 in which determination of categorization fiducial time $t_C$ in flow chart element 118 is done by analyzing a detected heartbeat from flow chart element 112 prior to heartbeat categorization 116. In FIG. 18B (and in FIG. 18A), flow chart element 112 may include storage of more than the most recent ECG signals, and such ECG signals may be available to be used in the remaining method steps of embodiment 120 or other embodiments of the inventive method of heartbeat categorization.

In the embodiments 110 and 120 of FIGS. 18A and 18B, respectively, heartbeat categorization 10B" is shown as utilizing the method steps of embodiment 10B of FIG. 2 by substituting the value of categorization fiducial time $t_C$ for the value for heartbeat detection time $t_D$. This substitution is found in detail in FIG. 20. Thus, in these embodiments, heartbeat categorization is independent of the inventive steps of heartbeat detection shown in FIGS. 1, 3 and 22-28. The term heartbeat categorization is used here specifically for flow chart element 10B" (and 10B''') and more generally for the combined steps 116 which include forming the vector $F(t_C)$ in flow chart element 114 and flow chart element 10B" (and 10B''') since the formation and use of vector $F(t_C)$ is an important element of the inventive method for heartbeat categorization as disclosed herein.

Figure 19:
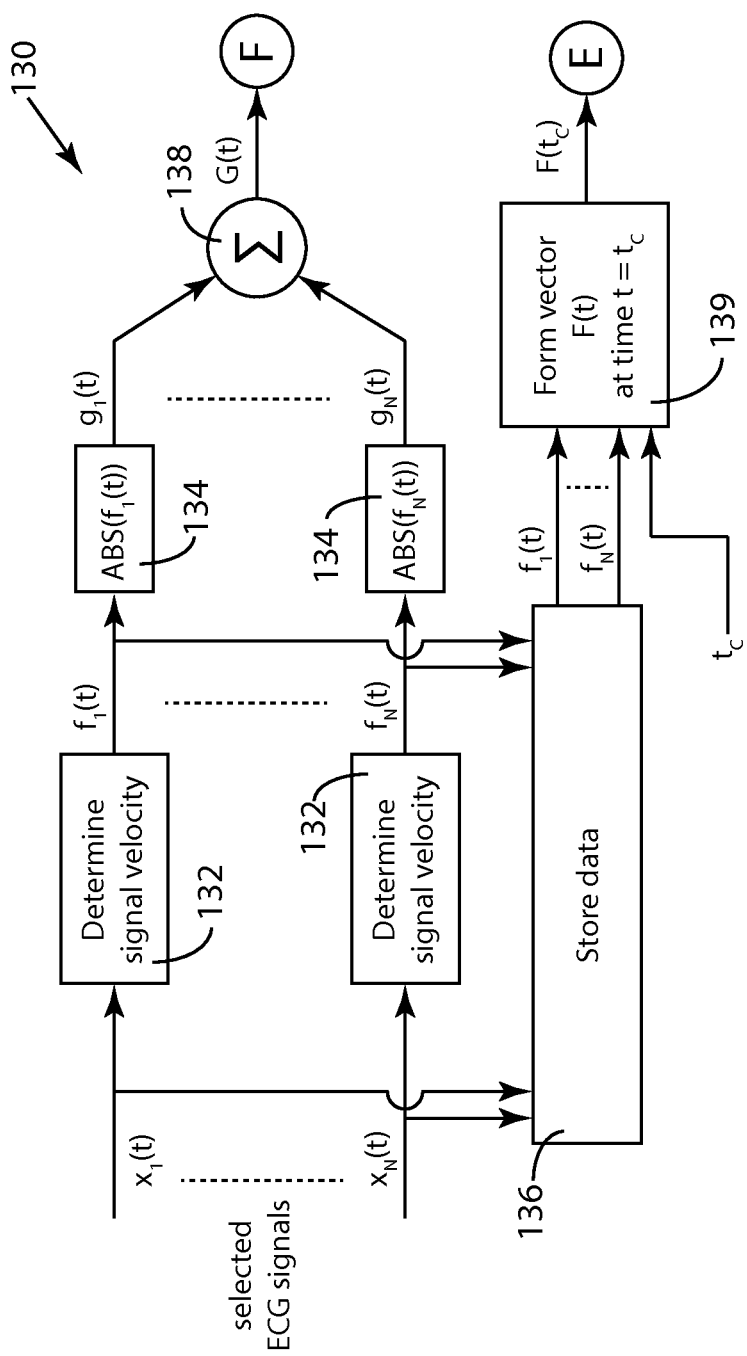
FIG. 19 is a block diagram schematic of method steps which generate velocity sum $G(t)$ and vector $F(t_C)$. $G(t)$ is used for some methods of heartbeat detection, and vector $F(t_C)$ is used within the inventive heartbeat categorization method.

FIG. 19 is a more detailed block diagram schematic of method steps which generate velocity sum G(t) and vector $F(t_C)$ for later use in the inventive method. G(t) is used for some methods of heartbeat detection, and vector $F(t_C)$ is used within the inventive heartbeat categorization method as disclosed herein. In flow chart elements 132, the signal velocities $f_p(t)$ are determined, and in flow chart elements 134, the absolute values $g_p(t)$ of velocities $f_p(t)$ are determined. In flow chart element 136, values of $x_p(t)$ and $f_p(t)$ are stored as needed. Summing point 138 provides the summation of $g_p(t)$ to generate absolute value velocity sum G(t) which may be used for heartbeat beat detection as needed. In flow chart element 139, vector $F_C(t)$ is formed for use within later portions of categorization.

Figure 20:
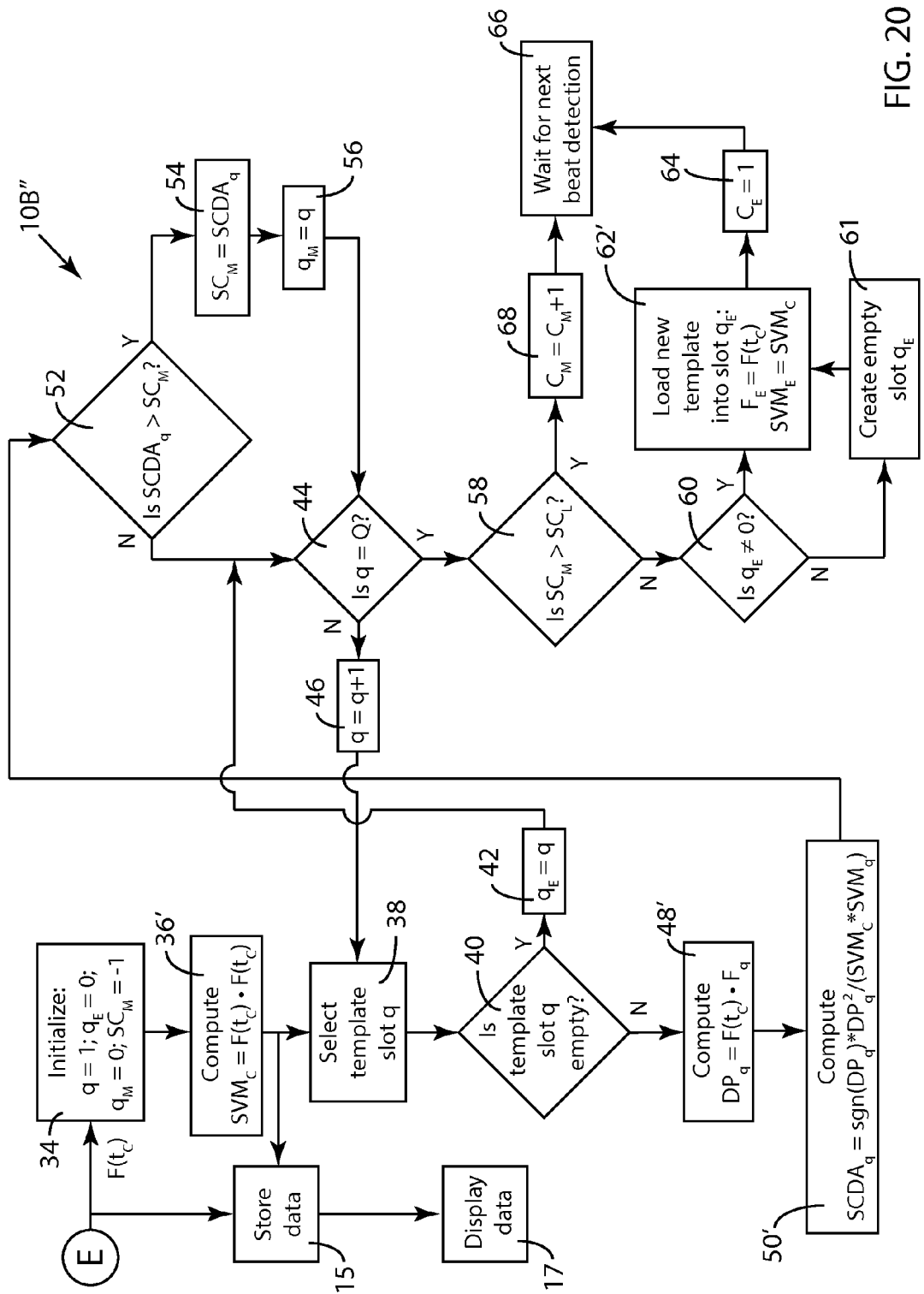
FIG. 20 is a modification of FIG. 2 with heartbeat detection time $t_D$ replaced with categorization fiducial time $t_C$ in the method steps of embodiment 10B of FIG. 2 to produced the method steps of embodiment 10B" of FIG. 20.
Figure 21:
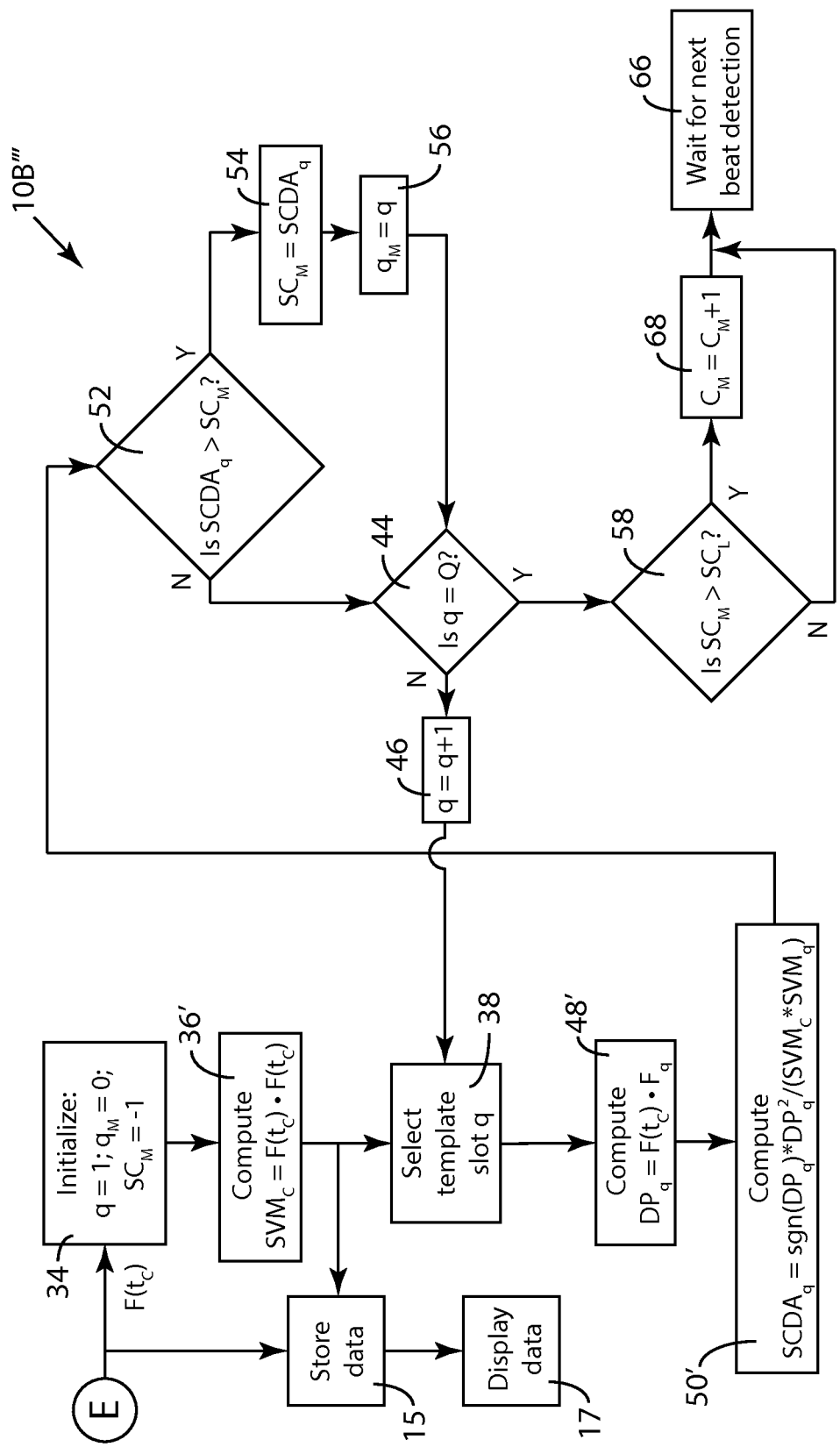
FIG. 21 is a modification of FIG. 12 with heartbeat detection time $t_D$ replaced with categorization fiducial time $t_C$ in the method steps of embodiment 10B' of FIG. 12 to produced the method steps of embodiment 10B''' of FIG. 21.

The method steps of alternative embodiment 10B''' of FIG. 21 may be utilized in step 116 (see FIGS. 18A and 18B) instead of the method steps of the embodiment 10B" (FIG. 20). Similar to FIG. 20, FIG. 21 is a modification of FIG. 12 with heartbeat detection time $t_D$ replaced with categorization fiducial time $t_C$ in the method steps of FIG. 12 to produce the method steps of FIG. 21. In FIGS. 20 and 21, method steps 36', 48', 50', and 62' (FIG. 20 only) are indicated with primed reference numbers since these method steps include the aforementioned substitution in corresponding unprimed method steps in FIGS. 2 and 12, respectively.

Referring to FIGS. 18A, 18B and 19, such figures show the vector $F(t_C)$ formed in method step 114 (FIGS. 18A and 18B) and method step 139 (FIG. 19) in a similar fashion as in method step 26 of FIG. 1. Vector $F(t_C)$ of velocities $f_p(t_C)$ is formed such that $F(t_C)=\{f_1(t_C), \ldots, f_N(t_C)\}$. The vectors $F(t_C)$ are inputs to the method steps of embodiment 10B" of FIG. 20 (or embodiment 10B''' of FIG. 21) as indicated by point E in FIGS. 18A, 18B, 19, 20 and 21. Point E indicates that the processes of embodiments 110 and 120 proceed from point E of FIGS. 18A and 18B and from embodiment 130 of FIG. 19 to the corresponding points in FIG. 20 or 21, depending on the specific embodiments of the inventive method. The differences between the method steps of FIGS. 20 and 21 are found in the descriptions of FIGS. 2 and 12 earlier in this document. Note that the block diagram elements 10B" in FIGS. 18A and 18B are shown in dotted lines to indicate that these elements are shown in FIGS. 18A and 18B as well as in FIGS. 20 and 21 as indicated by the use of point E in the embodiments of the diagrams. (This redundancy in FIGS. 18A and 18B merely further illustrates that point E corresponds to the input for the method steps of FIGS. 20 and 21.)

FIGS. 22A-28 illustrate several embodiments for finding categorization fiducial time $t_C$ within a detected heartbeat, the information about which is then passed to the inventive method for heartbeat categorization. In these figures, where velocity sum G(t) is involved in the embodiments, the same representative trace of G(t) within a single cardiac cycle is used in FIGS. 22B, 23B, 24B, 25C, and 26B to provide illustration of the various embodiments. The representative trace of G(t) includes the cardiac cycle spanning the time from t=1.765 seconds to 2.821 seconds. The data used for this representative G(t) comes from the same dataset as is used in other figures herein, such as FIGS. 6A-9D. The signals are sampled at 1000 sps.

As used herein, the term "heartbeat" more specifically refers to the more active portion of the ECG signals within a cardiac cycle, typically referred to as the QRS complex and well-known to those skilled in the area of cardiology. A heartbeat is detected within a cardiac cycle, and the data stored and analyzed in order to determine categorization fiducial time $t_C$ includes the data within a cardiac cycle. Thus, in general, the entire time history of ECG signals can be stored and some computed values may also be stored for quicker retrieval when needed. Modern computing equipment is capable of extremely fast computation and storing very large amounts of data which enables some such rapid and data-intensive computation to occur essentially in real time.

Figure 22A:
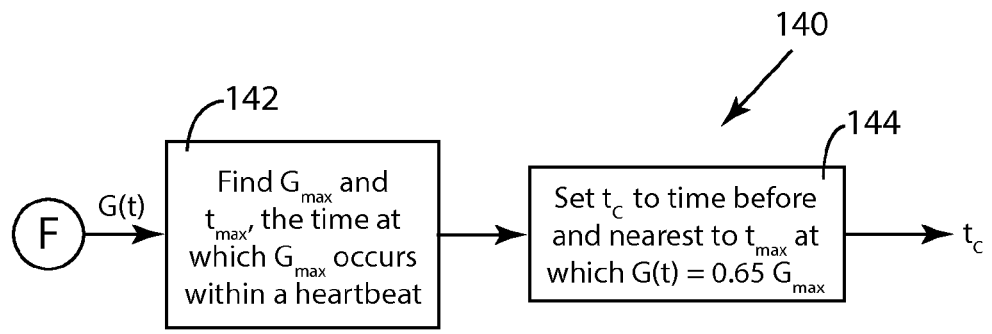
FIG. 22A is a block diagram schematic of an embodiment in which the categorization fiducial time $t_C$ is determined as the time within a detected heartbeat before and nearest to the peak of velocity sum $G(t)$ when the sum is substantially equal to a preset fraction of $G(t)$.

FIG. 22A is a block diagram schematic of an embodiment 140 in which categorization fiducial time $t_C$ is determined as the time within a detected heartbeat before and nearest to the peak of velocity sum G(t) within the detected heartbeat when the sum is substantially equal to a preset fraction of G(t). G(t) is passed from the method steps of embodiment 130 (FIG. 19) at point F. In method step 142, the maximum $G_{max}$ of G(t) within the detected heartbeat is found, and the time of the occurrence of $G_{max}$ is $t_{max}$. In method step 144, $t_C$ is set as the time at which G(t) is equal to a preset fraction (65%) of $G_{max}$. In exemplary embodiment 140, the preset fraction shown as 65%, but the value 65% as the preset fraction is not intended to be limiting to the scope of the heartbeat categorization method of this invention. It is merely chosen here in FIGS. 22A and 22B as exemplary.

Figure 22B:
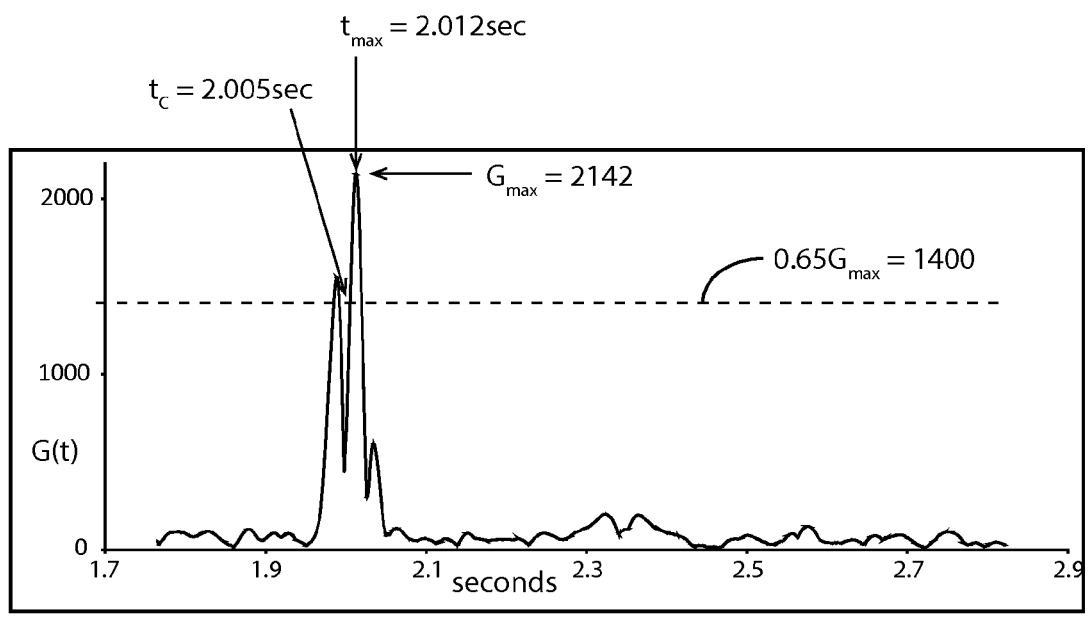
FIG. 22B is a plot of a representative time trace of $G(t)$ illustrating the determination of categorization fiducial time $t_C$ as shown in FIG. 22A.

FIG. 22B is a plot of a representative time trace of G(t) illustrating the determination as illustrated in FIG. 22A. In FIG. 22B, $G_{max}$ is 2142 at $t_{max}$=2.012 seconds. There are three points within the exemplary detected heartbeat of FIG. 22B at which G(t) is equal to 65% of $G_{max}$. These three points are at t=1.984 seconds, t=1.992 seconds and t=2.005 seconds. Among these three points, the value of time t before and nearest to $t_{max}$ is 2.005 seconds; thus, in this example, $t_C$=2.005 seconds, as indicated in FIG. 22B.

This determined value of $t_C$ is passed to method step 139 of embodiment 130 (FIG. 19), and method step 139 uses the data stored at method step 136 to form vector $F(t_C)$ which is then passed at point E to embodiments 10W (FIG. 20) or 10B''' (FIG. 21) for heartbeat categorization.

Figure 23A:
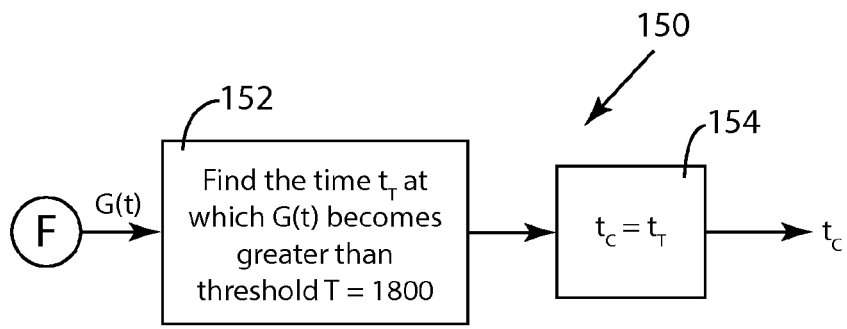
FIG. 23A is a block diagram schematic of an embodiment in which the categorization fiducial time $t_C$ is determined as the time within a detected heartbeat at which the velocity sum $G(t)$ becomes greater than a threshold T.

FIG. 23A is a block diagram schematic of an embodiment 150 in which categorization fiducial time $t_C$ is determined as the time within a detected heartbeat at which velocity sum G(t) becomes greater than a threshold T. As in embodiment 140 of FIG. 22A, G(t) is passed from the method steps of embodiment 130 (FIG. 19) at point F. In method step 152, the time $t_T$ at which G(t) becomes greater than threshold T is determined, and in method step 154, $t_C$ is set to time $t_T$. In exemplary embodiment 150, threshold T is shown as having a value of 1800, but this value for T is not intended to be limiting to the scope of the heartbeat categorization method of this invention. It is merely chosen here in FIGS. 23A and 23B as exemplary.

Figure 23B:
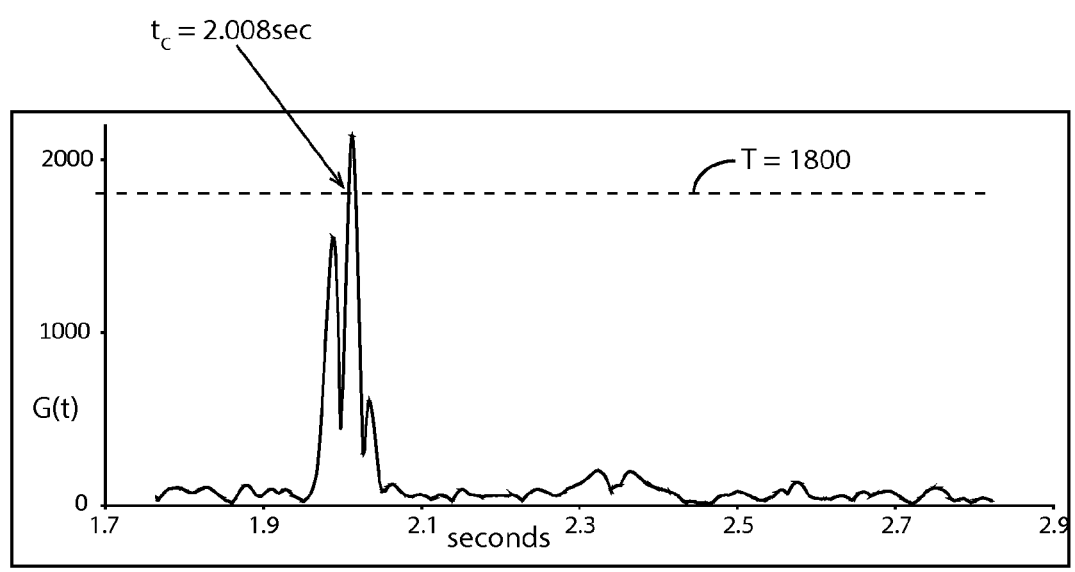
FIG. 23B is a plot of a representative time trace of $G(t)$ illustrating the determination of categorization fiducial time $t_C$ as shown in FIG. 23A.

FIG. 23B is a plot of a representative time trace of G(t) illustrating the determination as illustrated in FIG. 23A. In FIG. 23B, $t_T$ occurs at t=2.008 seconds.

As with embodiment 140 of FIG. 22A, the determined value $t_C$ in embodiment 150 of FIG. 23A is passed to method step 139 of embodiment 130 (FIG. 19), and method step 139 uses the data stored at method step 136 to form vector $F(t_C)$ which is then passed at point E to embodiments 10W (FIG. 20) or 10B''' (FIG. 21) for heartbeat categorization.

Figure 24A:
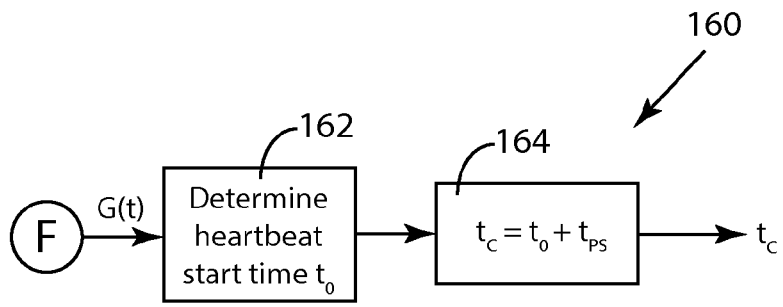
FIG. 24A is a block diagram schematic of an embodiment in which the categorization fiducial time $t_C$ is determined to be at a preset time after the start of a detected heartbeat.

FIG. 24A is a block diagram schematic of an embodiment 160 in which categorization fiducial time $t_C$ is determined to be at a preset time $t_{PS}$ after the start time $t_0$ of a detected heartbeat. In flow chart element 162, start time $t_0$ is determined as the time at which velocity sum G(t) rises above a heartbeat-pending threshold $T_p$ and remains above $T_p$ until G(t) rises above a heartbeat-confirming threshold $T_c$. Flow chart element 164 simply illustrates this setting of time $t_C$ at preset time $t_{PS}$ after start time $t_0$.

Figure 24B:
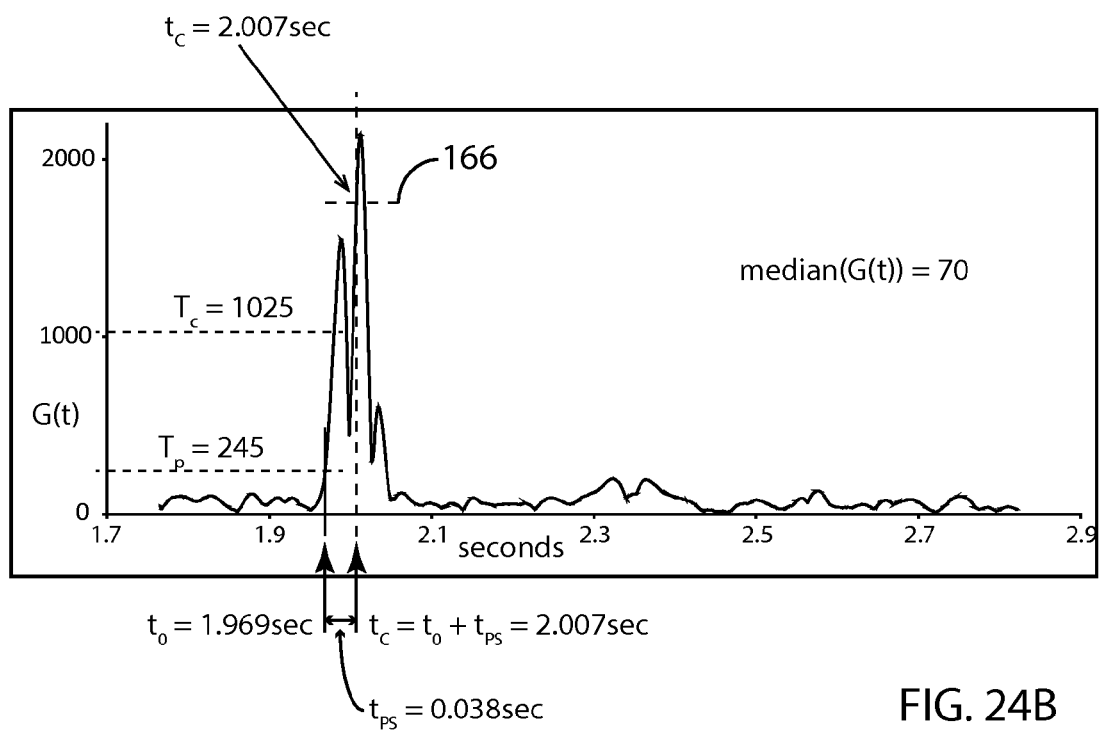
FIG. 24B is a plot of a representative time trace of $G(t)$ illustrating the determination of categorization fiducial time $t_C$ as shown in FIG. 24A.

FIG. 24B is a plot of a representative time trace of G(t) illustrating the determination of categorization fiducial time $t_C$ as outlined in FIG. 24A. The cardiac cycle in FIG. 24B begins at time 1.765 seconds and ends at time 2.821 seconds. The determination of start time $t_0$ in flow chart element 162 includes the computation of the median of sum G(t) across the cardiac cycle, and the median of G(t) in FIG. 24B is found to be 70. Heartbeat-pending threshold $T_p$ is set in this exemplary embodiment as 3.5 times the median as indicated in FIG. 24B; thus, $T_p$=245. Heartbeat-confirming threshold $T_c$ is set in this example at 50% of the expected peak, and the value of the expected peak was found to be 2050; thus, $T_c$=1025.

Referring again to FIG. 24B, using the above values for $T_p$ and $T_c$ as shown, $t_0$ occurs at t=1.969 seconds, and a preset time $t_{PS}$ of 0.038 seconds is used, yielding a determined value of $t_C$ of 2.007 sec. The value for $t_{PS}$ of 0.038 seconds used in exemplary embodiment 160 is not intended to be limiting to the scope of the heartbeat categorization method of this invention. (The horizontal dotted line 166 simply indicates point along the trace of velocity sum $G(t_C)$ although this value of G(t) is not of particular importance in embodiment 160.)

The expected value of the peak of the sum G(t) may be determined in a variety of ways, such as by computing the average of a number of past peaks. The average may also be weighted toward more recent peaks. The method by which the expected value of the peak of G(t), the exemplary value for the multiple of the median of G(t), and the fraction of the peak by which $T_c$ is determined are all not intended to be limiting to the scope of the inventive method of heartbeat categorization as disclosed herein.

The use of a multiple of the median of sum G(t) sets the value of heartbeat-pending threshold $T_p$ above the signal noise in G(t), and the use of a fraction of the expected value of the peak of sum G(t) for heartbeat-confirming threshold $T_c$ attempts to assure that no QRS complexes are missed (false negatives) and that there are no extra detections (false positives) of QRS complexes. A useful range of this fraction of the expected value of the peak is between about 30% and 60%. The height of the peaks in sum G(t) typically vary such that too high a value may miss some heartbeats. Further, too low a value for heartbeat-confirming threshold $T_c$ may introduce false positives from ECG features such as P-waves.

The determined value of $t_C$ in embodiment 160 of FIG. 24A is passed to method step 139 of embodiment 130 (FIG. 19), and method step 139 uses the data stored at method step 136 to form vector $F(t_C)$ which is then passed at point E to embodiments 10B'' (FIG. 20) or 10B''' (FIG. 21) for heartbeat categorization.

Figure 25A:
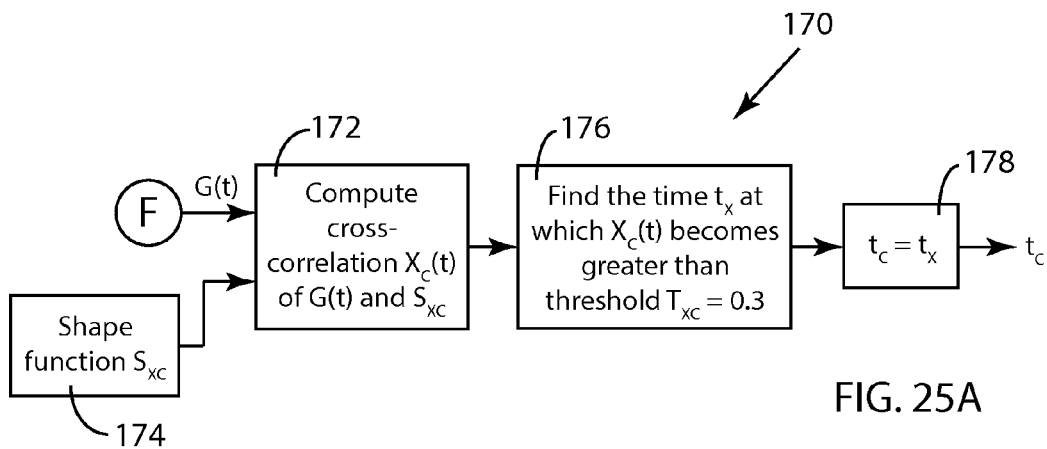
FIG. 25A is a block diagram schematic of an embodiment in which the categorization fiducial time $t_C$ is determined as the time at which the cross-correlation of sum $G(t)$ and a shape function becomes greater than a correlation threshold.

FIG. 25A is a block diagram schematic of an embodiment 170 in which the categorization fiducial time $t_C$ is determined as the time at which a cross-correlation $X_C(t)$ of sum G(t) and a shape function $S_{XC}$ becomes greater than a correlation threshold $T_{XC}$. Flow chart element 174 provides shape function $S_{XC}$ to flow chart element 172 in which cross-correlation $X_C(t)$ is computed. In flow chart element 176, the time $t_X$ at which cross-correlation $X_C(t)$ becomes greater than correlation threshold $T_{XC}$ is determined. Threshold $T_{XC}$ in this example is shown as 0.3 (30% of the peak value of $X_C(t)$ since $X_C(t)$ has been normalized to have a maximum value of 1.) In flow chart element 176, categorization fiducial time $t_C$ is set to $t_X$.

Figure 25B:
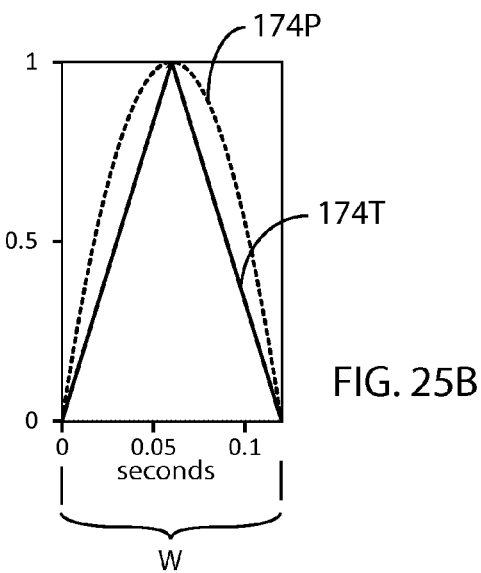
FIG. 25B illustrates two possible shape functions to cross-correlate with the sum $G(t)$ in the embodiment of FIG. 25A.

FIG. 25B illustrates two possible shape functions $S_{XC}$ to be used to cross-correlate with sum G(t) in the embodiment 170 of FIG. 25A. Shape function 174T is triangular in shape, and shape function 174P is parabolic in shape. Shape functions 174T and 174P are shown in FIG. 25B as having a width W of 120 milliseconds. Width W is about the width of many QRS complexes found in the field of human electrophysiology, and a width range of about 90 to 150 milliseconds is found to encompass a very wide range of human QRS complexes.

Figure 25C:
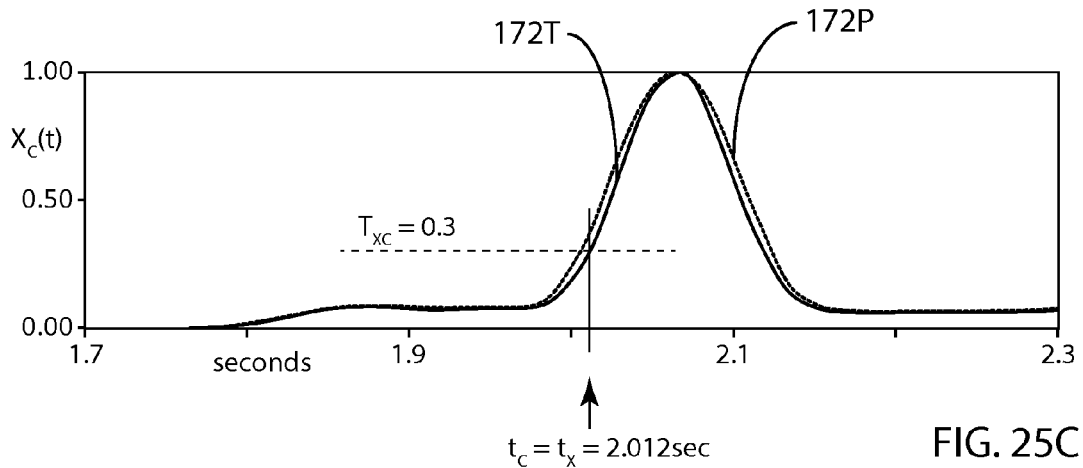
FIG. 25C shows two plots of cross-correlations of a representative portion of a sum $G(t)$ with the two shape functions of FIG. 25B, the plots illustrating the determination of categorization fiducial time $t_C$ as described in the block diagram schematic of FIG. 25A.

FIG. 25C shows two plots of cross-correlations $X_C(t)$ of a representative portion of a sum G(t) with the two shape functions of FIG. 25B. Cross-correlation plot 172T (solid line) has resulted from cross-correlating G(t) with shape function 174T (solid line), and cross-correlation plot 172P (dotted line) has resulted from cross-correlating G(t) with shape function 174P (dotted line). Cross-correlation plot 174T is used in FIG. 25C to illustrate the determination of categorization fiducial time $t_C$ as described in the block diagram schematic of FIG. 25A. Correlation threshold $T_{XC}$ is shown as 0.3, and the time $t_X$ at which $X_C(t)$ becomes greater than $T_{XC}$ is shown as 2.012 seconds. Categorization fiducial time $t_C$ is thus determined to be 2.012 seconds in embodiment 170.

The determined value of $t_C$ in embodiment 170 of FIG. 25A is passed to method step 139 of embodiment 130 (FIG. 19), and method step 139 uses the data stored at method step 136 to form vector $F(t_C)$ which is then passed at point E to embodiments 10B" (FIG. 20) or 10B''' (FIG. 21) for heartbeat categorization.

Figure 26A:
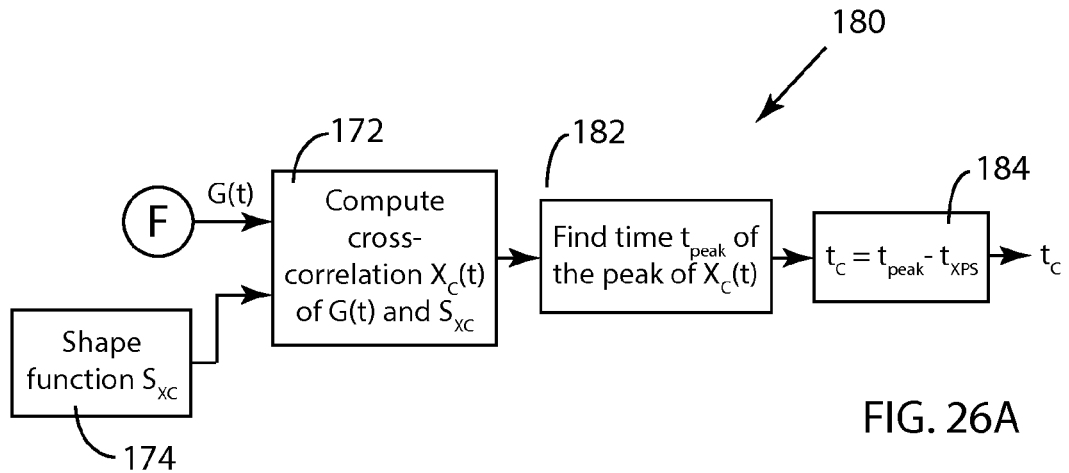
FIG. 26A is a block diagram schematic of an embodiment in which the categorization fiducial time $t_C$ is determined as the time at which the cross-correlation of sum $G(t)$ and a shape function reaches its peak minus a preset interval of time.

FIG. 26A is a block diagram schematic of an embodiment 180 in which the categorization fiducial time $t_C$ is determined as the time at which the cross-correlation $X_C(t)$ of sum G(t) and shape function reaches its peak value minus a preset time interval $t_{XPS}$. Flow chart element 174 provides shape function $S_{XC}$ to flow chart element 172 in which cross-correlation $X_C(t)$ is computed. (As is embodiment 170, cross-correlation $X_C(t)$ has been normalized to produce a maximum value of 1.) In flow chart element 182, the time $t_{peak}$ of the occurrence of the cross-correlation peak is determined, and in flow chart element 184, categorization fiducial time $t_C$ is set to $t_{peak}$ minus a preset correlation time interval $t_{XPS}$.

Figure 26B:
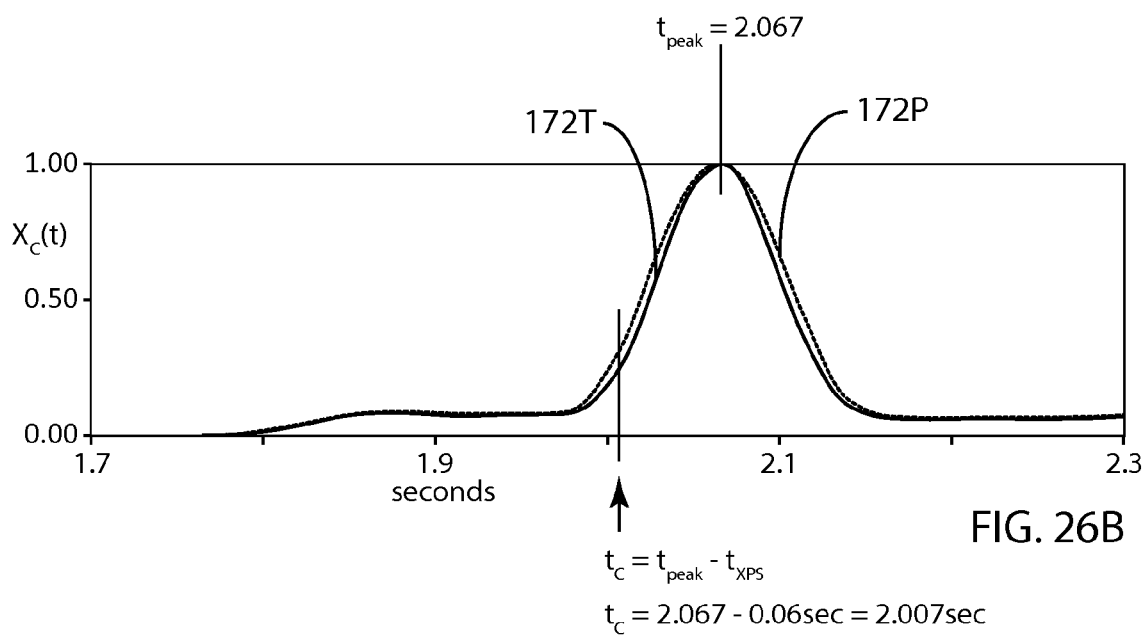
FIG. 26B shows two plots of cross-correlations of a representative portion of a sum $G(t)$ with the two shape functions of FIG. 25B, the plots illustrating the determination of categorization fiducial time $t_C$ as described in the block diagram schematic of FIG. 26A.

FIG. 26B shows the same two plots of cross-correlations $X_C(t)$ as shown in FIG. 25C. As in FIG. 25C, cross-correlation plot 172T has resulted from cross-correlating G(t) with shape function 174T, and cross-correlation plot 172P has resulted from cross-correlating G(t) with shape function 174P. Cross-correlation plot 174T is used in FIG. 26B to illustrate the determination of categorization fiducial time $t_C$ as described in the block diagram schematic of FIG. 26A. The peak of cross-correlation $X_C(t)$ of plot 172T is shown to be at time $t_{peak}$=2.067 seconds. Also as shown in FIG. 26B, preset correlation time interval $t_{XPS}$ in the example is set at 0.06 seconds, thus resulting in a determined value of categorization fiducial time tC of 2.007 seconds.

The determined value of $t_C$ in embodiment 180 of FIG. 26A is passed to method step 139 of embodiment 130 (FIG. 19), and method step 139 uses the data stored at method step 136 to form vector $F(t_C)$ which is then passed at point E to embodiments 10B" (FIG. 20) or 10B''' (FIG. 21) for heartbeat categorization.

Figure 27:
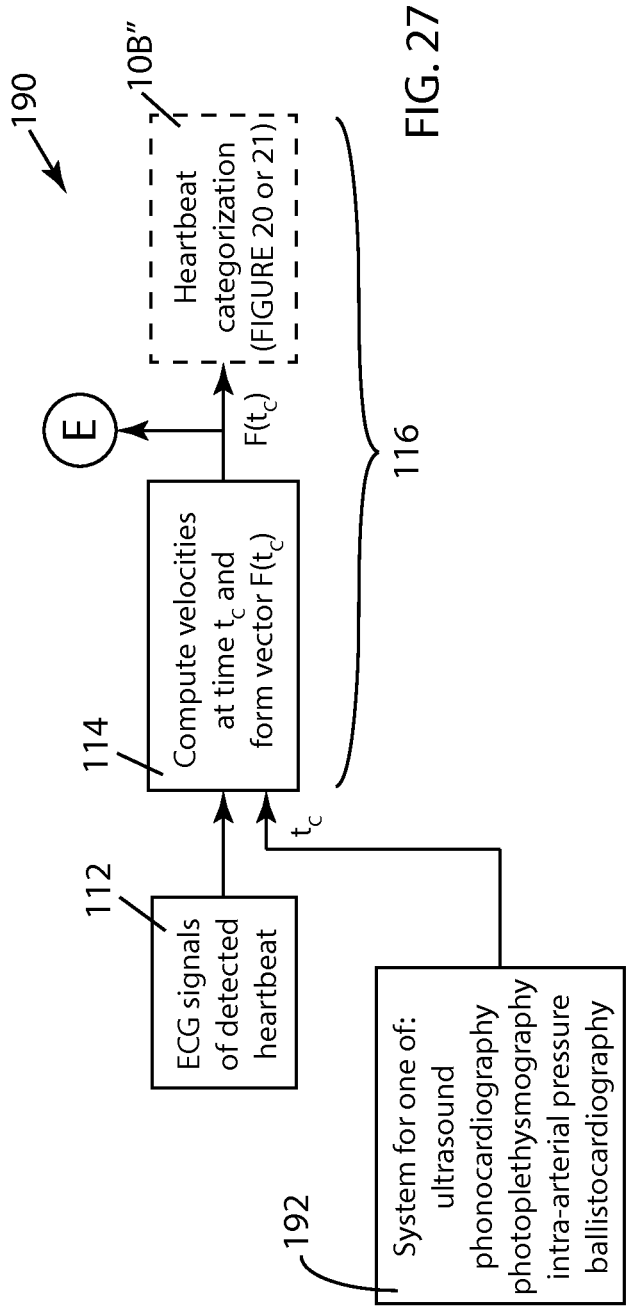
FIG. 27 is a block diagram schematic of an embodiment in which the source of categorization fiducial time $t_C$ is a system which uses sensors other than ECG electrodes.

Heartbeats may be detected by a numerous methods and systems. Among this group are systems such as motion ultrasound, audio (phonocardiography), optical (photoplethysmography), intra-arterial blood pressure measurement, and body motion measurement (ballistocardiography). FIG. 27 illustrates an embodiment 190 in which such a non-ECG system is the source for heartbeat detection and categorization fiducial time $t_C$. FIG. 27 is a modification of FIG. 18A and illustrates one of such systems 192 as providing heartbeat detection and the determination of categorization fiducial time $t_C$ to the inventive heartbeat categorization method disclosed herein. Using categorization fiducial time $t_C$ provided by heartbeat detector 192 and ECG signals from flow chart element 112, flow chart element 114 computes signals velocities and forms vector $F(t_C)$ which is then available at point E for operations within the method steps of embodiment 10B" (or 10B''') as described earlier in this document.

Methods and systems 192 all use different sensing technologies to produce a continuous time measurement of a parameter that varies recognizably and usefully with every heartbeat. By detecting a feature (such as peak, slope or zero-crossing) of these parameter waveforms and offsetting by an appropriate time interval, the moment of the beginning of a heartbeat can be identified, and categorization fiducial time $t_C$ can be determined.

A method to detect heart rate from ultrasound is known and often of use in monitoring a fetus because application of ECG electrodes to the fetus is impractical or impossible in the mother's womb. Peters et al. (2004 Physiol. Meas. 25, 585-593) and Jezewski et al. (IEEE Trans. on Biomedical Engineering, Vol. 53, Issue 5, May 2006, 855-864) are two examples of the use of this technology to determine heart rate from Doppler ultrasound.

Phonocardiography is the science of graphing heart activity as evidenced from the audio sounds produced mainly by the working of heart valves. Doctors hear these same sounds via a stethoscope. The science is useful again for fetal monitoring because of the difficulty of attaching ECG electrodes. It is particularly useful in telemonitoring for which patients are required to make connections themselves at remote locations, often difficult for the non-professional. Godinez et al. (Proceedings of the Engineering in Medicine and Biology Society Int'l Conf., Sep. 17-21, 2003, 3141-3144) and Torres-Pereira (Proceedings of the IEEE Int'l Symposium on Industrial Electronics, Jul. 7-11, 1997, 856-859) are two examples of heart rate determination from phonocardiograms.

Photoplethysmography is the science of graphing a changing volume measured by the transmission of light through the volume. It is a subset of the technology used in pulse oximeters which measure heart rate and blood oxygenation. Blood flow is inferred from the changing volume of the finger. Such devices are very useful and simple, typically being attached to a patient's finger. The signal from such a system contains information suitable for obtaining heart rate. Dekker (U.S. Pat. No. 6,702,752) discloses an example of heart rate determination from a pleth signal, and Selvarej et al. (Journal of Medical Engineering & technology, Vol. 32, No. 6, November/December 2008, 479-484) presents a further example of heart rate determination from a pleth signal.

Intra-arterial blood pressure measurement is considered the gold standard of blood pressure measurements because it employs a direct mechanical connection, the output of which is a blood pressure waveform. The upstroke of pressure occurs when the heart contracts (systolic phase) and is early in the cardiac cycle. Mancia et al. (Hypertension. February 1987; vol. 9:209-215) and de Boer et al. (Medical & Biological Engineering & Computing, July 1985, Vol. 4, pp 352-358) disclose two examples of heart rate measurement from an intra-arterial blood pressure waveform.

Sensitive force transducers can detect the shifting masses as the heart pumps blood if a patient will otherwise lie still, for example on a bed. The science is called ballistocardiography. Mack et al. (IEEE Trans. on Information Technology in Biomedicine, Vol. 13, Issue 1, January 2009, 111-120) and Alihank et al. (Journal of the American Physiological Society—Regulatory, Integrative and Comparative Physiology, May 1, 1981, Vol. 240, No. R384-R392) show two examples of systems that measure heart rate from the ballistogram by selective filtering.

Figure 28:
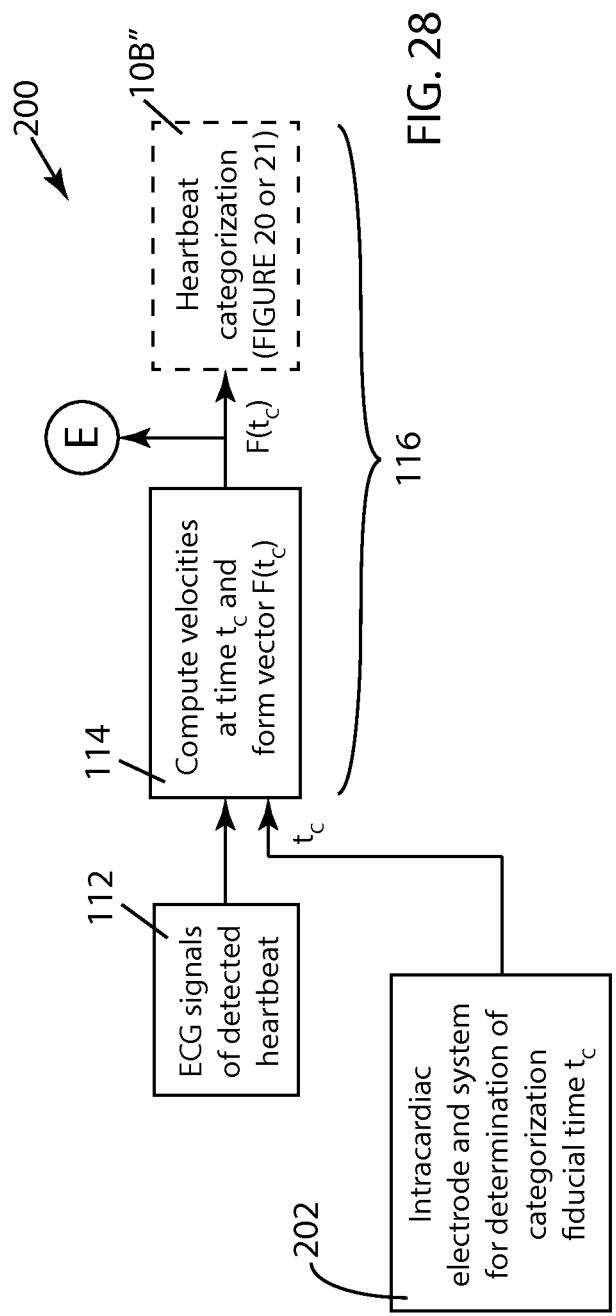
FIG. 28 is block diagram schematic of an embodiment in which the source of categorization fiducial time $t_C$ is a system which uses an intracardiac electrode other than the ECG electrodes otherwise used to generate the ECG signals for the method steps for heartbeat categorization.

FIG. 28 illustrates an additional alternative embodiment 200 of the inventive method for heartbeat categorization which utilizes the signal from an intracardiac electrode 202 placed adjacent to the origin of the heartbeat to determine the categorization fiducial time $t_C$. The intracardiac electrode provides a cardiac signal separate from the ECG channel signals being used within the heartbeat categorization method steps. Using categorization fiducial time $t_C$ provided by the signal from intracardiac electrode 192 and ECG signals from flow chart element 112, flow chart element 114 computes signals velocities and forms vector $F(t_C)$ which is then available at point E for operations within the method steps of embodiment 10B″ (or 10B‴) as described earlier in this document.

While the principles of this invention have been described in connection with specific embodiments, it should be understood clearly that these descriptions are made only by way of example and are not intended to limit the scope of the invention.

The invention claimed is:

1. An automatic method for categorizing heartbeats, the method comprising, when a heartbeat has been detected, the steps of:
sensing two or more selected ECG signals with electrodes; and
automatically processing the ECG signals with a programmable processor configured to:
determine a signal velocity for each selected signal at a categorization fiducial time $t_C$ within the detected heartbeat;
form a vector $F(t_C)$ the components of which are the velocities of each of the selected signals at the time $t_C$;
determine the angle between the vector $F(t_C)$ and a previously-stored template vector;
compare the angle with a threshold angle; and
categorize the heartbeat as similar to a heartbeat which corresponds to the template vector when the angle is less than the threshold angle.

2. The automatic heartbeat categorization method of claim 1 wherein the angle determination and comparison include the steps of:
computing a squared vector magnitude $SVM_C$ as the dot product $F(t_C) \cdot F(t_C)$,
computing the dot product $DP_q$ of $F(t_C)$ with a template vector $F_q$;
computing a squared vector magnitude $SVM_q$ as the dot product $F_q \cdot F_q$;
computing a signed squared cosine difference angle $SCDA_q$ as $SCDA_q = \text{sgn}(DP_q) * DP_q * DP_q / (SVM_C * SVM_q)$; and comparing $SCDA_q$ with a squared cosine threshold $SC_L$.

3. The automatic heartbeat categorization method of claim 2 further including comparing the vector $F(t_C)$ with each of a plurality of template vectors to determine if the vector $F(t_C)$ is within the threshold angle of any of the plurality of template vectors.

4. The automatic heartbeat categorization method of claim 3 wherein when the angle between the vector $F(t_C)$ and more than one of the plurality of template vectors is less than the threshold angle, categorizing the heartbeat as similar to a heartbeat which corresponds to the template vector having the smallest angle between itself and the vector $F(t_C)$.

5. The automatic heartbeat categorization method of claim 4 wherein when the angle between the vector $F(t_C)$ and each of the plurality of template vectors is greater than or equal to the threshold angle, adding a template vector equal to the vector $F(t_C)$ to the plurality of template vectors.

6. The automatic heartbeat categorization method of claim 4 wherein the patient is in a non-sedated state and further including the step of providing interventional treatment to the patient in a sedated state based on heartbeats categorized while the patient was in the non-sedated state.

7. The automatic heartbeat categorization method of claim 1 further including comparing the vector $F(t_C)$ with each of a plurality of template vectors to determine if the vector $F(t_C)$ is within the threshold angle of any of the plurality of template vectors.

8. The automatic heartbeat categorization method of claim 7 wherein when the angle between the vector $F(t_C)$ and more than one of the plurality of template vectors is less than the threshold angle, categorizing the heartbeat as similar to a heartbeat which corresponds to the template vector having the smallest angle between itself and the vector $F(t_C)$.

9. The automatic heartbeat categorization method of claim 7 wherein when the angle between the vector $F(t_C)$ and each of the plurality of template vectors is greater than or equal to the threshold angle, adding a template vector equal to the vector $F(t_C)$ to the plurality of template vectors.

10. The automatic heartbeat categorization method of claim 7 wherein the patient is in a non-sedated state and further including the step of providing interventional treatment to the patient in a sedated state based on heartbeats categorized while the patient was in the non-sedated state.

11. The automatic heartbeat categorization method of claim 7 wherein each of the template vectors has a threshold angle associated therewith, and not all such vectors have the same threshold angle associated therewith.

12. The automatic heartbeat categorization method of claim 7 wherein at least a portion of the plurality of template vectors are preset template vectors.

13. The automatic heartbeat categorization method of claim 12 wherein each of the plurality of template vectors is a preset template vector.

14. The automatic heartbeat categorization method of claim 4 further including a slot-plurality of template vector slots, the slot-plurality being greater than or equal to the plurality of template vectors and each template vector is stored in a corresponding template vector slot, wherein if the vector $F(t_C)$ is not within the threshold angle of any of the plurality of template vectors and an empty template vector slot is available, adding a template vector equal to the vector $F(t_C)$ to the plurality of template vectors.

15. The automatic heartbeat categorization method of claim 14 wherein if no empty template vector slot is available, replacing one of the template vectors with a new template vector equal to the vector $F(t_C)$.

16. The automatic heartbeat categorization method of claim 1 further including storing the categorized heartbeat.

17. The automatic heartbeat categorization method of claim 16 further including displaying information descriptive of one or more stored heartbeats.

18. The automatic heartbeat categorization method of claim 1 wherein determining the velocity of each of the selected signals includes:
digitizing each of the selected signals; and
filtering each of the digitized signals to generate the velocity for each selected signal.

19. The automatic heartbeat categorization method of claim 1 further including selecting three ECG signals, and the signals form a quasi-orthogonal set.

20. The automatic heartbeat categorization method of claim 1 wherein the ECG signals further include one or more ECG signals in addition to the selected ECG signals, and the method includes storing one or more of the additional ECG signals.

21. The automatic heartbeat categorization method of claim 20 further including displaying information descriptive of a detected heartbeat.

22. The automatic heartbeat categorization method of claim 1 further including, when a heartbeat has been detected, the steps of:
 forming a vector $F(t_C)$ the components of which are the velocities of each of the selected signals at the time $t_C$ and the velocities of each of the selected signals at time $t_C+\delta$;
 determining the angle between the vector $F(t_C)$ and a previously-stored template vector;
 comparing the angle with a threshold angle; and
 when the angle is less than the threshold angle, categorizing the heartbeat as similar to a heartbeat which corresponds to the template vector.

23. The automatic heartbeat categorization method of claim 22 wherein angle determination and comparison include the steps of:
 computing a squared vector magnitude $SVM_C$ as the dot product $F(t_C) \cdot F(t_C)$;
 computing the dot product $DP_q$ of $F(t_C)$ with a template vector $F_q$;
 computing a squared vector magnitude $SVM_q$ as the dot product $F_q \cdot F_q$;
 computing a signed squared cosine difference angle $SCDA_q$ as $SCDA_q = \text{sgn}(DP_q) * DP_q * DP_q / (SVM_C * SVM_q)$; and comparing $SCDA_q$ with a squared cosine threshold $SC_L$.

24. The automatic heartbeat categorization method of claim 23 further including comparing the vector $F(t_C)$ with each of a plurality of template vectors to determine if the vector $F(t_C)$ is within the threshold angle of any of the plurality of template vectors.

25. The automatic heartbeat categorization method of claim 24 wherein if the angle between the vector $F(t_C)$ and more than one of the plurality of template vectors is less than the threshold angle, categorizing the heartbeat as similar to a heartbeat which corresponds to the template vector having the smallest angle between itself and the vector $F(t_C)$.

26. The automatic heartbeat categorization method of claim 25 wherein if the angle between the vector $F(t_C)$ and each of the plurality of template vectors is greater than or equal to the threshold angle, adding a template vector equal to the vector $F(t_C)$ to the plurality of template vectors.

27. The automatic heartbeat categorization method of claim 25 wherein the patient is in a non-sedated state and further including the step of providing interventional treatment to the patient in a sedated state based on heartbeats categorized while the patient was in the non-sedated state.

28. The automatic heartbeat categorization method of claim 22 further including comparing the vector $F(t_C)$ with each of a plurality of template vectors to determine if the vector $F(t_C)$ is within the threshold angle of any of the plurality of template vectors.

29. The automatic heartbeat categorization method of claim 28 wherein when the angle between the vector $F(t_C)$ and more than one of the plurality of template vectors is less than the threshold angle, categorizing the heartbeat as similar to a heartbeat which corresponds to the template vector having the smallest angle between itself and the vector $F(t_C)$.

30. The automatic heartbeat categorization method of claim 28 wherein when the angle between the vector $F(t_C)$ and each of the plurality of template vectors is greater than or equal to the threshold angle, adding a template vector equal to the vector $F(t_C)$ to the plurality of template vectors.

31. The automatic heartbeat categorization method of claim 28 wherein the patient is in a non-sedated state and further including the step of providing interventional treatment to the patient in a sedated state based on heartbeats categorized while the patient was in the non-sedated state.

32. The automatic heartbeat categorization method of claim 28 wherein each of the template vectors has a threshold angle associated therewith, and not all such vectors have the same threshold angle associated therewith.

33. The automatic heartbeat categorization method of claim 28 wherein at least a portion of the plurality of template vectors are preset template vectors.

34. The automatic heartbeat categorization method of claim 33 wherein each of the plurality of template vectors is a preset template vector.

35. The automatic heartbeat categorization method of claim 22 further including a slot-plurality of template vector slots, the slot-plurality being greater than or equal to the plurality of template vectors and each template vector is in a corresponding template vector slot, wherein if the vector $F(t_C)$ is not within the threshold angle of any of the plurality of template vectors and an empty template vector slot is available, adding a template vector equal to the vector $F(t_C)$ to the plurality of template vectors.

36. The automatic heartbeat categorization method of claim 35 wherein if no empty template vector slot is available, replacing one of the template vectors with a new template vector equal to the vector $F(t_C)$.

37. The automatic heartbeat categorization method of claim 22 further including storing ECG signals corresponding to the categorized heartbeat.

38. The automatic heartbeat categorization method of claim 37 further including displaying information descriptive of one or more stored heartbeats.

39. The automatic heartbeat categorization method of claim 1 further including the steps of:
 storing the selected signals;
 determining a velocity $f(t)$ for each of the selected signals;
 summing the absolute values of each signal velocity $f(t)$ to generate an absolute velocity sum $G(t)$;
 finding the maximum peak of the sum and the time thereof within the detected heartbeat; and
 setting time $t_C$ as the time before and nearest to the time of the peak when the sum is substantially equal to a preset fraction of the peak.

40. The automatic heartbeat categorization method of claim 1 further including the steps of:
 storing the selected signals;
 determining a velocity $f(t)$ for each of the selected signals;
 summing the absolute values of each signal velocity $f(t)$ to generate an absolute velocity sum $G(t)$; and
 setting $t_C$ equal to the time at which sum $G(t)$ becomes greater than a threshold T.

41. The automatic heartbeat categorization method of claim 1 further including the steps of:
 storing the selected signals;
 determining the time $t_C$ as a preset time after the start of the detected heartbeat.

42. The automatic heartbeat categorization method of claim 41 further including the steps of:
    determining a velocity f(t) for each of the selected signals;
    summing the absolute values of each signal velocity f(t) to generate an absolute velocity sum G(t); and
    determining the start of the detected heartbeat as the time at which sum G(t) rises above a heartbeat-pending threshold $T_p$ and remains above $T_p$ until G(t) rises above a heartbeat-confirming threshold $T_c$.

43. The automatic heartbeat categorization method of claim 42 wherein the detected heartbeat is within a cardiac cycle and the method further includes the step of computing the median of G(t) within the cardiac cycle, $T_p$ being a multiple of the median of G(t) across the cardiac cycle.

44. The automatic heartbeat categorization method of claim 43 wherein the multiple is between 2 and 5.

45. The automatic heartbeat categorization method of claim 42 wherein $T_c$ is between 30% and 60% of the expected peak of the detected heartbeat.

46. The automatic heartbeat categorization method of claim 1 further including the steps of:
    storing the selected signals;
    determining a velocity f(t) for each of the selected signals;
    summing the absolute values of each signal velocity f(t) to generate an absolute velocity sum G(t);
    cross-correlating G(t) with a predetermined shape function; and
    deriving time $t_C$ from the cross-correlation.

47. The automatic heartbeat categorization method of claim 46 wherein the time $t_C$ is set at the time the cross-correlation becomes greater than a correlation threshold.

48. The automatic heartbeat categorization method of claim 47 wherein the correlation threshold is between about 25% and 35% of the peak value of the cross-correlation.

49. The automatic heartbeat categorization method of claim 48 wherein the correlation threshold is about 30% of the peak value of the cross-correlation.

50. The automatic heartbeat categorization method of claim 46 wherein the time $t_C$ is set at a preset correlation time interval before the time of maximum cross-correlation.

51. The automatic heartbeat categorization method of claim 46 wherein the predetermined shape function is a triangle.

52. The automatic heartbeat categorization method of claim 46 wherein the predetermined shape function is a parabola.

53. The automatic heartbeat categorization method of claim 46 wherein the width of the shape function is between about 90 and 150 milliseconds.

54. The automatic heartbeat categorization method of claim 53 wherein the width of the shape function is about 120 milliseconds.

55. The automatic heartbeat categorization method of claim 1 further including deriving the time $t_C$ from an output signal of a heartbeat detector selected from the group consisting of motion ultrasound, audio, optical detection of blood flow, pressure measurement, and ballistocardiography.

56. The automatic heartbeat categorization method of claim 1 further including deriving the time $t_C$ from an intracardiac signal from an electrode placed adjacent to the origin of the heartbeat.

* * * * *

UNITED STATES PATENT AND TRADEMARK OFFICE
CERTIFICATE OF CORRECTION

| | | |
|---|---|---|
| PATENT NO. | : 9,078,575 B2 | Page 1 of 1 |
| APPLICATION NO. | : 14/219826 | |
| DATED | : July 14, 2015 | |
| INVENTOR(S) | : Donald Brodnick | |

It is certified that error appears in the above-identified patent and that said Letters Patent is hereby corrected as shown below:

In the Specification
At column 7, line 17, delete "produced" and insert --produce--.
At column 7, line 21, delete "produced" and insert --produce--.
At column 8, line 1, insert --a-- between "is block".
At column 8, lines 52 and 53, insert --. . . ,-- in the formula after "(t),".
At column 8, line 53, insert --. . . ,-- in the second formula after "(t),".
At column 8, line 58, insert --of-- between "set coefficients".
At column 8, line 63, delete "made" and insert --may--.
At column 8, line 67, delete the "," and insert a --.-- after "50 Hz".
At column 11, line 27, delete ")cos$^2$(25°" and insert --cos$^2$(25°)--.
At column 11, line 46, delete "=)180°." and insert --=180°).--.
At column 14, line 40, delete "which" to make this a sentence.
At column 14, line 46, delete "region" and insert --regions--.
At column 14, line 56, delete "$B_{in}$," and insert --$B_{int}$--.
At column 15, line 62, delete ")cos$^2$(25°" and insert --cos$^2$(25°)--.
At column 15, line 67, delete "($\theta_g$113°)" and insert --($\theta_g$= 113°)--.
At column 16, line 10, delete "4.953" and insert --4.593--.
At column 16, line 16, delete "t," and insert --$t_D$--.
At column 16, line 51, delete "t" and insert --$t_i$--.
At column 17, line 45, delete "70" and insert --90--.
At column 17, line 55, delete "element represent" and insert --element 96 represents--.
At column 22, line 22, delete "indicates point" and insert --indicates a point--.
At column 23, line 50, delete "tC" and insert --$t_C$--.
At column 23, line 57, delete "a".
At column 25, line 14, delete "signals" and insert --signal--.

Signed and Sealed this
Second Day of February, 2016

Michelle K. Lee
*Director of the United States Patent and Trademark Office*